(12) United States Patent
Takao et al.

(10) Patent No.: US 8,017,336 B2
(45) Date of Patent: Sep. 13, 2011

(54) METHOD OF EXAMINING ZINC-DEFICIENT TASTE DISTURBANCE BY DETERMINING EXPRESSION LEVEL OF TASTE RECEPTOR GENES

(75) Inventors: Kyoichi Takao, Tokyo (JP); Minoru Ikeda, Tokyo (JP); Keiko Onoda, Tokyo (JP)

(73) Assignee: Nihon University, Tokyo (JP)

( * ) Notice: Subject to any disclaimer, the term of this patent is extended or adjusted under 35 U.S.C. 154(b) by 380 days.

(21) Appl. No.: 12/087,129

(22) PCT Filed: Dec. 27, 2006

(86) PCT No.: PCT/JP2006/326363
§ 371 (c)(1),
(2), (4) Date: Jun. 26, 2008

(87) PCT Pub. No.: WO2007/174937
PCT Pub. Date: Jul. 5, 2007

(65) Prior Publication Data
US 2009/0305245 A1    Dec. 10, 2009

(30) Foreign Application Priority Data
Dec. 27, 2005    (JP) ................. 2005-376717

(51) Int. Cl.
  *C12Q 1/68*    (2006.01)
  *C12P 19/34*    (2006.01)
(52) U.S. Cl. .................... 435/6.12; 435/91.2
(58) Field of Classification Search ............. 435/6, 91.2, 435/6.12; 536/24.33
See application file for complete search history.

(56) References Cited

U.S. PATENT DOCUMENTS
5,176,995 A * 1/1993 Sninsky et al. ............. 435/6
2008/0145842 A1  6/2008 Takao et al.

FOREIGN PATENT DOCUMENTS
| JP | 2003-510037 A | 3/2003 |
| JP | 2003-530098 A | 10/2003 |
| WO | WO 01/18050 A2 | 3/2001 |
| WO | WO 01/77676 A1 | 10/2001 |
| WO | 2004/007716 * | 1/2004 |
| WO | WO 2006/001544 A1 | 1/2006 |

OTHER PUBLICATIONS

Ikeda et al., "Diagnosis and Treatment of Smell and Taste Disorders 4: Etiological Factors of Taste Disorders", The Japanese Journal of Taste and Smell Research, 2003 Nen 4 Gatsu, vol. 10, No. 1, pp. 71-76.
Kazama et al., "Development of novel gustometry", Japan Society for Bioscience, Biotechnology, and Agrochemistry 2006 Nendo (Heisei 18 Nendo), Taikai Koen Yoshishu, Mar. 5, 2006, p. 158 (paragraph 2C34p04).
Onoda et al., "Study on taste receptor gene expression in tongues of taste disorder patients under treatment (2nd report)", Koku Inkoka, vol. 19, No. 1, Aug. 10, 2006, p. 88.
Onoda et al., "Study on taste receptor genes in tongues of taste disorder patients under treatment", The Oto-Rhino-Laryngological Society of Japan, Inc. Kaiho, vol. 109, No. 4, Apr. 20, 2006 (see #138).
Onoda et al., "Study on taste receptor genes in tongues of taste disorder patients", Koku Inkoka, vol. 18, No. 1, Aug. 10, 2005, p. 179.
Takao et al., "Applications of novel gustometry for humans", Japan Society for Bioscience, Biotechnology, and Agrochemistry 2006 Nendo (Heisei 18 Nendo) Taikai Koen Yoshishu, Mar. 5, 2006, p. 158 (paragraph 2C34p05).
Takao et al., "Taste receptors expressed in normal and taste disordered persons and changes therein", The Japanese Journal of Taste and Smell Research, 2005 Nen 12 Gatsu Jojun, vol. 12, No. 3, pp. 493-496.
Takao et al., "The Expression Pattern of Candidate Taste Receptors in the Tongue and the Oral Cavity of Normal and Taste Disordered Persons," Shoku ni Kansuru Josei Kenkyu Chosa Hokokusho, 2005 Nen 10 Gatsu, No. 18, pp. 49-55.
Extended European Search Report, dated May 15, 2009, for European Application No. 06843734.2.
Ikeda et al., The Japanese Journal of Taste and Smell Research, 2003 Nen 4 Gatsu, vol. 10, No. 1, pp. 71-76.
International Preliminary Report on Patentability, mailed Nov. 27, 2007, for International Application No. PCT/JP2006/326363, including English Translation (Forms PCT/IPEA/416 and PCT/IPEA/409).
International Search Report, mailed Feb. 6, 2007, for International Application No. PCT/JP2006/326363.
Kazama et al., Japan Society for Bioscience, Biotechnology, and Agrochemistry 2006 Nendo (Heisei 18 Nendo), Taikai Koen Yoshishu, Mar. 5, 2006, p. 158 (paragraph 2C34p04).
O'Nion et al., "Effect of Zinc Supplementation on Red Blood Cell Zinc, Serum Zinc, Taste Acuity, and Dietary Intake in Zinc Deficient Dialysis Patients," Dialysis and Transplantation, vol. 7, No. 12, pp. 1208-1210 and 1213, 1978, XP-002518611, Abstract only provided.
Onoda et al., Koku Inkoka, vol. 18, No. 1, Aug. 10, 2005, p. 179.
Onoda et al., Koku Inkoka, vol. 19, No. 1, Aug. 10, 2006, p. 88.
Onoda et al., The Oto-Rhino-Laryngological Society of Japan, Inc. Kaiho, vol. 109, No. 4, Apr. 20, 2006 (see #138).
Takao et al., "The Expression Pattern of Candidate Taste Receptors in the Tongue and the Oral Cavity of Normal and Taste Disordered Persons," Shoku ni Kansuru Josei Kenkyu Chosa Hokokusho, 2005 Nen 10 Gatsu, No. 18, pp. 49-55.
Takao et al., Japan Society for Bioscience, Biotechnology, and Agrochemistry 2006 Nendo (Heisei 18 Nendo) Taikai Koen Yoshishu, Mar. 5, 2006, p. 158 (paragraph 2C34p05).
Takao et al., The Japanese Journal of Taste and Smell Research, 2005 Nen 12 Gatsu Jojun, vol. 12, No. 3, pp. 493-496.

(Continued)

*Primary Examiner* — Kenneth R. Horlick
(74) *Attorney, Agent, or Firm* — Birch, Stewart, Kolasch & Birch, LLP

(57) ABSTRACT

The present invention provides: a method for testing zinc deficiency dysgeusia, which is characterized in that it comprises correlating the expression levels of a gene encoding a gustatory receptor belonging to the THTR family and a gene encoding a gustatory receptor belonging to the T2R family obtained from a sample derived from the oral cavity of a subject, with a serum zinc level obtained from the sample of the subject; and a kit used for the aforementioned test.

9 Claims, 2 Drawing Sheets

OTHER PUBLICATIONS

Takeda et al., "Identification of G protein-coupled receptor genes from the human genome sequence," FEBS Letters, vol. 520, 2002, pp. 97-101.

Tanaka, "Secretory Function of the Salivary Gland in Patients with Taste Disorders or Xerostomia: Correlation with Zinc Deficiency," Acta Oto-Larylgologica, Suppl. No. 546, 2002, pp. 134-141, XP009113479.

Tazaki et al., "Leukemia Case in Patient with Taste Dysfunction," The Bulletin of Tokyo Dental College, vol. 46, Nos. 1-2, May 2005, pp. 33-36, XP-002518610.

Written Reply, filed Oct. 12, 2001, for International Application No. PCT/JP2006/326363, including English translation thereof.

Yoshikawa, "Experimental Study on Drug-Induced Taste Disorders in Rats," Nihon University Journal of Medicine, vol. 39, No. 6, 1997, pp. 353-367, XP-002518612, Abstract only provided.

* cited by examiner

METHOD OF EXAMINING ZINC-DEFICIENT TASTE DISTURBANCE BY DETERMINING EXPRESSION LEVEL OF TASTE RECEPTOR GENES

TECHNICAL FIELD

The present invention relates to a method for testing zinc deficiency dysgeusia using the expression level of a taste substance-reactive composition (gustatory receptor) and a serum zinc level as indicators, and a kit for testing zinc deficiency dysgeusia.

BACKGROUND OF THE INVENTION

Gustatory sense is an important sense for life. Thus, abnormal gustatory sense gives a strong stress to patients' mentality. However, since such gustatory sense is a subjective sense, which can be recognized by only a person in question, it is difficult to objectively grasp the pathologic condition thereof. Hence, it is hard to say that an effective treatment is carried out for patients suffering from dysgeusia. Moreover, since such disorder of the sense of taste is not directly associated with the life-or-death matter of humans, it hardly becomes the object of interest for researchers. To date, dysgeusia has been tested by two main types of methods. One of them is called electrogustometry. This is a method, which comprises passing a weak current through the tongue and determining the disorder of the sense of taste based on the degree of the feeling obtained when electrical stimulation that is similar to taste is given. However, it is difficult for this method to detect abnormalities of individual qualities of tastes such as sweetness or bitterness. The other method is called a filter disk method. The filter disk method comprises placing a filter impregnated with each of taste substances in various concentrations on various sites of the tongue and hearing opinions from the subjects regarding the presence or absence of the taste. This method enables detection of the degree of feeling of 4 basic tastes such as sweetness, saltiness, sourness and bitterness, or the correctness of the feeling. However, this method is problematic in that good results cannot be obtained if subjects do not reach age when they understand the concept of this test, or if they do not have enough knowledge. Moreover, this method is also problematic when subjects do not know how to express the taste although they feel the taste. Thus, in a case where such subjects are infants and toddlers, or are elder people who are hearing-impaired, this test has almost no sense.

The aforementioned method enables detection of the presence or absence of dysgeusia, but it cannot clarify the cause of such dysgeusia.

By the way, in the case of mammals, the sense of taste is considered to be classified into 5 types of tastes such as sweetness, bitterness, delicious taste, sourness, and saltiness. Each quality of taste is considered to be transmitted via each different communication system. It is said that G protein-coupled receptors (GPCR) are involved in transmission of sweetness, bitterness, and delicious taste, and that ion channels are deeply involved in transmission of saltiness and sourness. However, the relationship between such receptors and taste substances has not yet been clarified. If such gustatory receptors (GPCR or channel proteins) selectively activate or inactivate towards chemical stimulation from the outside world, it is considered that cells on the tongue (taste cells) that express such receptors respond to such stimulation, and that information regarding a taste substance is transmitted to the central nerve.

As stated above, several gustatory receptors belong to the G protein-coupled receptors having a seven-transmembrane structure. In recent years, studies regarding G protein-coupled receptors for taste substances have vigorously been progressing. At current, T1R, T2R, and THTR families have been identified as gustatory receptors (Takeda et al. FEBS Lett. 520, 97-101, 2002) (National Publication (in Japan) of International Patent Application Nos. 2003-530098 and 2003-510037). However, the type of a substance used as a ligand (agonist) of such receptors, and in particular, of the THTR family, is still unknown.

Accordingly, it is desired to clarify such gustatory receptors, and to find a ligand acting as a taste substance. In addition, it is also desired to develop a novel method for testing dysgeusia, which does not depend on the personal view of a subject.

DISCLOSURE OF THE INVENTION

It is an object of the present invention to provide a method for detecting zinc deficiency dysgeusia and a kit for detecting dysgeusia.

As a result of intensive studies directed towards achieving the aforementioned object, the present inventor has established a method for testing zinc deficiency dysgeusia by making comparisons regarding the expression frequencies of gustatory receptor genes based on the causes of dysgeusia, thereby completing the present invention. That is to say, the present invention is as follows:

(1) A method for testing zinc deficiency dysgeusia, which is characterized in that it comprises correlating the expression levels of a gene encoding a gustatory receptor belonging to the THTR family and/or a gene encoding a gustatory receptor belonging to the T2R family obtained from a sample derived from the oral cavity of a subject, with a serum zinc level obtained from the sample of the subject.

(2) The method according to (1) above, wherein the gustatory receptor belonging to the THTR family is at least one selected from the group consisting of THTR 1, 2, 3, 4, 5, 6, 7, 9, 11, 12, and 14.

(3) The method according to (1) above, wherein the gustatory receptor belonging to the THTR family is a polypeptide described in (a) or (b) below:
(a) a polypeptide having the amino acid sequence as shown in SEQ ID NO: 2, 4, 6, 8, 10, 12, 14, 16, 18, 20, or 22; or
(b) a polypeptide having an amino acid sequence comprising a deletion, substitution, or addition of one or several amino acids with respect to the amino acid sequence as shown in SEQ ID NO: 2, 4, 6, 8, 10, 12, 14, 16, 18, 20, or 22, and functioning as a gustatory receptor.

(4) The method according to (1) above, wherein the gustatory receptor belonging to the THTR family is a polypeptide encoded by DNA described in (a) or (b) below:
(a) DNA having the nucleotide sequence as shown in SEQ ID NO: 1, 3, 5, 7, 9, 11, 13, 15, 17, 19, or 21; or
(b) DNA hybridizing with DNA having a nucleotide sequence complementary to the DNA having the nucleotide sequence as shown in SEQ ID NO: 1, 3, 5, 7, 9, 11, 13, 15, 17, 19, or 21 under stringent conditions, and encoding a polypeptide functioning as a gustatory receptor.

(5) The method according to (1) above, wherein the gustatory receptor belonging to the T2R family is at least one selected from the group consisting of T2R 1, 3, 4, 5, 7, 8, 9, 10, 13, 14, and 16.

(6) The method according to (1) above, wherein the gustatory receptor belonging to the T2R family is a polypeptide described in (a) or (b) below:

(a) a polypeptide having the amino acid sequence as shown in SEQ ID NO: 24, 26, 28, 30, 32, 34, 36, 38, 40, 42, or 44; or
(b) a polypeptide having an amino acid sequence comprising a deletion, substitution, or addition of one or several amino acids with respect to the amino acid sequence as shown in SEQ ID NO: 24, 26, 28, 30, 32, 34, 36, 38, 40, 42, or 44, and functioning as a gustatory receptor.
(7) The method according to (1) above, wherein the gustatory receptor belonging to the T2R family is a polypeptide encoded by DNA described in (a) or (b) below:
(a) DNA having the nucleotide sequence as shown in SEQ ID NO: 23, 25, 27, 29, 31, 33, 35, 37, 39, 41, or 43; or
(b) DNA hybridizing with DNA having a nucleotide sequence complementary to the DNA having the nucleotide sequence as shown in SEQ ID NO: 23, 25, 27, 29, 31, 33, 35, 37, 39, 41, or 43 under stringent conditions, and encoding a polypeptide functioning as a gustatory receptor.
(8) The method according to (1) above, wherein the sample derived from the oral cavity is a tongue tissue sample collected by a scratch method.
(9) The method according to (1) above, wherein the expression level of a gustatory receptor gene is tested by amplification, and such amplification is carried out by amplifying the entire length of the gustatory receptor by RT-PCR.
(10) A kit for testing zinc deficiency dysgeusia, which is characterized in that it comprises a primer designed from DNA described in (a) or (b) below:
(a) DNA having the nucleotide sequence as shown in SEQ ID NOS: 45 to 88; or
(b) DNA hybridizing with DNA having a nucleotide sequence that is complementary to the DNA having the nucleotide sequence as shown in SEQ ID NOS: 45 to 88 under stringent conditions.

According to the present invention, a method for testing zinc deficiency dysgeusia is provided. Differing from the conventional techniques, the method of the present invention does not rely on the feeling of human, and thus it is able to test dysgeusia more objectively. In addition, using the test method of the present invention, it is possible to make the diagnosis of zinc deficiency dysgeusia and the prognosis of such zinc deficiency dysgeusia case. Thus, the test method of the present invention is extremely useful.

BEST MODE FOR CARRYING OUT THE INVENTION

Figure 1:
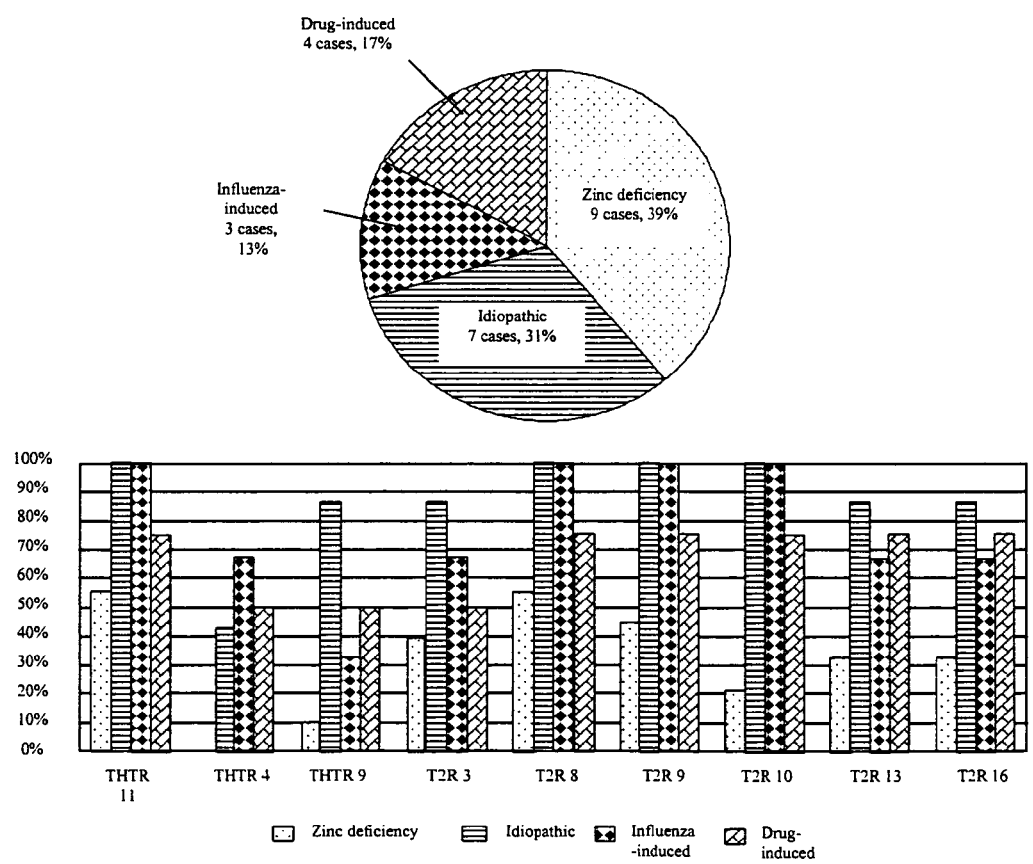
FIG. 1 is a view showing the classification results of dysgeusia based on the causes thereof, and the results obtained by making comparisons regarding the expression frequencies of gustatory receptor genes based on the causes of dysgeusia.

The present invention will be described in detail below. However, the following embodiments are provided to explain the present invention, and thus the present invention can be carried out in various embodiments unless it deviates from the gist thereof. All references and patent publications cited in the present specification are incorporated herein by reference in their entirety. In addition, the present specification includes the contents as disclosed in the specification and/or drawings of Japanese Patent Application No. 2005-376717, which is a priority document of the present application.

1. Summary

The present invention provides a method for testing dysgeusia, which is based on the correlation between a change in the expression level of multiple GPCR receptors that are considered to accept sweetness, bitterness, and delicious taste, and a serum zinc level. The method of the present invention is different from conventional methods for testing dysgeusia using the feeling of human as an indicator for determination. The present invention provides a method for testing dysgeusia, which comprises confirming the expression of multiple gustatory receptors by the RT-PCR method using a sample derived from the oral cavity and correlating the aforementioned expression level with a serum zinc level.

The present inventor has classified patients suffering from dysgeusia into those having zinc deficiency dysgeusia, idiopathic dysgeusia, influenza-induced dysgeusia, and drug-induced dysgeusia. The inventor has carried out a dysgeusia test regarding gustatory receptor genes that express in the tongue tissues of each patient. That is to say, the inventor detected by an RT-PCR method the expression level of 1-1 types of receptors (T2R 1, 3, 4, 5, 7, 8, 9, 10, 13, 14, and 16) that had already been reported as gustatory receptors and also the expression level of 11 types of receptors (THTR 1, 2, 3, 4, 5, 6, 7, 9, 11, 12, and 14) that had been considered to be candidates for gustatory receptors according to Takeda et al. (Takeda et al., FEBS Lett. 520, 97, 2002) in the tissues (human tongue tissues) of the aforementioned patients, and the inventor then analyzed to correlate such a gene expression level with a serum zinc level.

As a result, when compared with dysgeusia cases induced by other causes (e.g. idiopathic dysgeusia, influenza-induced dysgeusia, drug-induced dysgeusia, etc.), in the case of zinc deficiency dysgeusia, the expression frequency of a gustatory receptor gene on the tongue tissues tended to be low. In addition, in a case where the symptoms of zinc deficiency dysgeusia were not improved during the treatment thereof, the expression frequency of a gustatory receptor gene did not change. On the other hand, in a case where the symptoms of zinc deficiency dysgeusia were improved by continuous administration of a zinc preparation, the expression frequency of a gustatory receptor gene increased, and thus it tended to reflect the therapeutic effects.

Thus, the present invention enables testing of dysgeusia more objectively. Moreover, the present invention can be used in the diagnosis of zinc deficiency dysgeusia and it can also be used in the prognosis of zinc deficiency dysgeusia cases.

It is anticipated that a change in the expression level of a receptor that acts as a recipient of information brought by a taste substance be associated with dysgeusia. By testing such a change in the expression level of a receptor, it becomes possible to know the presence or absence of dysgeusia, the cause thereof, and a therapeutic target.

Furthermore, the present invention is useful in that a method of collecting tissues derived from the oral cavity is not carried out using a knife, but is carried out by almost painless noninvasive means (with a little burden on a subject).

2. Taste Substance-Reactive Composition (Gustatory Receptor)

The taste substance-reactive composition of the present invention (hereinafter referred to as a gustatory receptor at times) has a function to accept a taste substance and to transmit information obtained from the taste substance into the body. Among gustatory receptors, the gustatory receptor used in the present invention belongs to the THTR and T2R families included in GPCR. In particular, as such THTR family, THTR 1, 2, 3, 4, 5, 6, 7, 9, 11, 12, and 14 (amino acid sequences: SEQ ID NOS: 1 to 22 (only even numbers, namely, 2, 4, 6, 8, 10, 12, 14, 16, 18, 20, and 22)) can be used. As such T2R family, T2R 1, 3, 4, 5, 7, 8, 9, 10, 13, 14, and 16 (amino acid sequences: SEQ ID NOS: 23 to 44 (only even numbers, namely, 24, 26, 28, 30, 32, 34, 36, 38, 40, 42, and 44)) can be used. At that time, either gustatory receptors belonging to the aforementioned THTR family, or all of 22 gustatory receptors belonging to both the THTR and T2R families, may be used. Otherwise, several gustatory receptors may be used in combination, as appropriate. A list of the names of the aforementioned receptors used in the present invention, the nucleotide sequences thereof and the amino acid sequences thereof is shown in Table 1.

tion can be introduced into a polynucleotide by known means such as the Kunkel method or the Gapped duplex method, using a mutation introduction kit that utilizes the site-directed mutagenesis, such as QuickChange™ Site-Directed Mutagenesis Kit (manufactured by Stratagene), GeneTailor™ Site-Directed Mutagenesis System (manufactured by Invitrogen), or TaKaRa Site-Directed Mutagenesis System (Mutan-K, Mutan-Super Express Km, or the like; manufactured by Takara Bio).

TABLE 1

| Receptor name | SEQ ID NO. | | Receptor name | SEQ ID NO. | |
| --- | --- | --- | --- | --- | --- |
| | Nucleotide sequence | Amino acid sequence | | Nucleotide sequence | Amino acid sequence |
| THTR1/TAS2R38 | 1 | 2 | T2R1/TAS2R1 | 23 | 24 |
| THTR2/TAS2R47 | 3 | 4 | T2R3/TAS2R3 | 25 | 26 |
| THTR3/TAS2R45 | 5 | 6 | T2R4/TAS2R4 | 27 | 28 |
| THTR4-59 | 7 | 8 | T2R5TAS2R5 | 29 | 30 |
| THTR5/TAS2R40 | 9 | 10 | T2R7/TAS2R7 | 31 | 32 |
| THTR6/TAS2R39 | 11 | 12 | T2R8/TAS2R8 | 33 | 34 |
| THTR7 | 13 | 14 | T2R9/TAS2R9 | 35 | 36 |
| THTR9 | 15 | 16 | T2R10/TAS2R10 | 37 | 38 |
| THTR11/TAS2R48 | 17 | 18 | T2R13/TAS2R13 | 39 | 40 |
| THTR12/TAS2R49 | 19 | 20 | T2R14/TAS2R14 | 41 | 42 |
| THTR14/TAS2R44 | 21 | 22 | T2R16/TAS2R16 | 43 | 44 |

Regarding receptor name in Table 1, TAS2RX (wherein X represents any given number) means a registered designation in GenBank.

In the present invention, among the aforementioned receptor genes, with regard to the THTR family, THTR11, THTR4 and THTR9 are preferably used, and with regard to the T2R family, T2R3, T2R8, T2R9, T2R10, T2R13 and T2R16 are preferably used.

In addition, the aforementioned GPCR-type gustatory receptors are associated with sweetness, bitterness, and delicious taste. These receptors also include those, which are estimated as gustatory receptors based on the homology of the amino acid sequences thereof because their taste substance acting as a ligand has not been identified.

Moreover, the gustatory receptor used in the present invention may comprise a mutation such as a deletion, substitution, or addition of multiple amino acids, and preferably one or several amino acids in polypeptides having the amino acid sequences as shown in the aforementioned SEQ ID NOS: 1 to 44 (only even numbers from SEQ ID NOS: 1 to 44), as long as it functions as a gustatory receptor.

A polynucleotide encoding an amino acid sequence comprising a deletion, insertion, substitution, or addition of one or several amino acids with respect to a certain amino acid sequence, can be prepared according to the site-directed mutagenesis described in Molecular Cloning, A Laboratory Manual 2nd ed. (Cold Spring Harbor Press (1989)); Current Protocols in Molecular Biology (John Wiley & Sons (1987-1997), and particularly, Section 8.1-8.5); Kunkel (1985) Proc. Natl. Acad. Sci. USA 82: 488-92; etc. Furthermore, a muta- Examples of a "function as a gustatory receptor" may include binding activity to bind to a taste substance and taste substance-mediated signal transduction action. The expression "a function as a gustatory receptor" is used to mean that the receptor has a function that is almost equivalent to that of a protein having an amino acid sequence as shown in each sequence number, for example. Accordingly, it is preferable that a protein, which comprises a mutation such as a deletion, substitution, or addition of multiple amino acids, and preferably one or several amino acids, with respect to the amino acid sequences (only even numbers from SEQ ID NOS: 1 to 44) as shown in SEQ ID NOS: 1 to 44 (only even numbers from SEQ ID NOS: 1 to 44), has activity equivalent to or greater than (approximately 0.5 to 1.5 times) the protein having the amino acid sequence as shown in each sequence number. However, quantitative elements such as the level of such activity or the molecular weight of the protein may be different.

Furthermore, the gustatory receptor used in the present invention also includes a partial peptide of the aforementioned receptor. An example of such a partial peptide used herein is a site of a receptor molecule, which is exposed to the outside of the cell membrane and has receptor-binding activity. Specifically, such a partial peptide of the receptor is a peptide comprising a portion that has been analyzed to be an extracellular region (hydrophilic site) as a result of hydropathy plot analysis. Further, a peptide comprising a hydrophobic site as a portion thereof can also be used. A peptide comprising individual domains can also be used. A partial peptide, which comprises multiple domains simultaneously, may also be used. In the present invention, the above partial peptide may comprise the aforementioned mutation such as a deletion, substitution, or addition in its amino acid sequence.

The type of DNA encoding the gustatory receptor used in the present invention is not particularly limited, as long as it encodes a polypeptide having the amino acid sequence as shown in any one of SEQ ID NOS: 1 to 44 (only even numbers from SEQ ID NOS: 1 to 44), a mutant thereof, or a portion thereof. Examples of such DNA include DNAs having the nucleotide sequences as shown in SEQ ID NOS: 1 to 44 (only odd numbers from SEQ ID NOS: 1 to 44 (1, 3, 5, 7, 9, 11, 13, 15, 17, 19, 21, 23, 25, 27, 29, 31, 33, 35, 37, 39, 41, and 43)). In addition, DNA comprising a mutation such as a deletion, substitution, or addition of one or more nucleotides with respect to any one of the nucleotide sequences as shown in SEQ ID NOS: 1 to 44 (only odd numbers from SEQ ID NOS: 1 to 44) may also be included in the DNA of the present invention, as long as it functions as a gustatory receptor. Moreover, such DNA encoding the gustatory receptor polypeptide used in the present invention also includes DNA, which is capable of hybridizing with DNA having a nucleotide sequence that is complementary to the DNA having the nucleotide sequence as shown in any one of SEQ ID NOS: 1 to 44 (only odd numbers from SEQ ID NOS: 1 to 44) under stringent conditions, and which encodes a polypeptide functioning as a gustatory receptor. The term "stringent conditions" is used to mean conditions wherein a so-called specific hybrid is formed and a non-specific hybrid is not formed. Examples of such conditions are conditions wherein a complementary strand of DNA having high homology, that is, a complementary strand of DNA having homology of 60% or more, preferably 80% or more, more preferably 90% or more, and further more preferably 99% or more, hybridizes, and a complementary strand of DNA having homology lower than the above-described percentage does not hybridize. Specific examples of such stringent conditions may include conditions wherein a sodium concentration is set between 10 and 300 mM, and preferably between 20 and 100 mM, and wherein a temperature is set between 25° C. and 70° C., and preferably between 42° C. and 55° C.

In order to detect the amount of DNA encoding the aforementioned gustatory receptor polypeptide, the PCR method can be performed using each specific DNA.

The nucleotide sequences and amino acid sequences of the gustatory receptors used in the present invention are disclosed on the database of GenBank and the like. Using such genetic information, the primers of the present invention can be designed. Such primers should be designed such that only a receptor of interest can be amplified, when they are used in the PCR method. As DNA used to detect a change in the expression level of a gustatory receptor, the present invention includes, not only the aforementioned partial sequences (primers) capable of specifically amplifying the above gustatory receptor by the PCR method, but also DNA comprising a partial sequence (probe) specifically hybridizing with the above gustatory receptor, from among DNAs encoding gustatory receptor polypeptides. In order to examine the expression of a receptor gene with high sensitivity, it is preferable to amplify the receptor gene by the PCR method. As such a partial sequence, a sequence that amplifies the entire length of the THTR or T2R family may also be used. Moreover, such a partial sequence may be designed from each of DNA encoding the gustatory receptor polypeptide used in the present invention (e.g. SEQ ID NOS: 1 to 44 (only even numbers) and the mutants thereof) and DNA having a nucleotide sequence complementary thereto. Otherwise, such a partial sequence may also be designed from each of DNA encoding the gustatory receptor used in the present invention (e.g. SEQ ID NOS: 1 to 44 (only odd numbers) and the mutants thereof) and DNA having a nucleotide sequence complementary thereto. In the present invention, a primer preferably has a base length consisting of 18 to 27 nucleotides. In all of such cases, the partial sequence can be designed to amplify a full-length or a base length consisting of 300 to 1,000 nucleotides, preferably consisting of 500 to 900 nucleotides, and more preferably consisting of 700 to 800 nucleotides.

Furthermore, examples of the partial sequence of the present invention, and in particular, the primer of the present invention, may include primers used for amplifying the gustatory receptors shown in Table 2 set forth later, which are designed from DNA having the nucleotide sequence as shown in any one of SEQ ID NOS: 45 to 88, or DNA capable of hybridizing with DNA having a nucleotide sequence that is complementary to the DNA having the nucleotide sequence as shown in any one of SEQ ID NOS: 45 to 88 under stringent conditions. Stringent conditions are as described above.

The nucleotide sequences (SEQ ID NOS: 45, 47, . . . , 85, and 87) as shown in SEQ ID NOS: (2n+43) (wherein n represents an integer between 1 and 22) indicate the sequences consisting of $1^{st}$ to $18^{th}$-$26^{th}$ nucleotides with respect to the nucleotide sequences (SEQ ID NOS: 1, 3, . . . , 41, and 43) as shown in SEQ ID NOS: (2n−1) (wherein n represents an integer between 1 and 22). SEQ ID NOS: (2n+44) (n represents an integer between 1 and 22) (SEQ ID NOS: 46, 48, . . . , 86, and 88) indicate complementary sequences consisting of the last 18 to 26 nucleotides with respect to the nucleotide sequences as shown in SEQ ID NOS: (2n−1). Accordingly, SEQ ID NOS: (2n+43) and (2n+44) are pair primers, and such primers are able to amplify the entire length of DNA having the nucleotide sequence as shown in SEQ ID NO: (2n−1) by the PCR method.

A tag, a restriction enzyme recognition sequence, or the like, can appropriately be added to the 5'-terminal side of the primer of the present invention, as long as the above primer enables specific amplification of a receptor of interest.

DNA that is amplified with the primers of the present invention is DNA encoding the entire length or a part of a gustatory receptor polypeptide. From the view point of detection sensitivity and specificity in amplification, the length of DNA to be amplified is desirably the entire length of the gustatory receptor DNA. Further, it is also possible to add a necessary sequence to the 5'-terminal side of DNA used for amplification of the gustatory receptor used in the present invention. An example of such a sequence is a restriction enzyme recognition sequence.

The aforementioned primer or probe of the present invention can be produced according to known methods, or using a commercially available DNA synthesizer.

TABLE 2

| Primer name | Sequence | SEQ ID NOS. |
|---|---|---|
| THTR1/F | atg ttg act cta act cgc atc | 45 |
| THTR1/R | tca gca cag tgt ccg gga atc t | 46 |
| THTR2/F | atg ata act ttt ctg ccc atc a | 47 |
| THTR2/R | cta gaa gac aca caa tgc ccc tc | 48 |
| THTR3/F | atg ata act ttt ctg ccc atc | 49 |
| THTR3/R | tca gta cct cat ttg cca caa aac tg | 50 |

TABLE 2-continued

| Primer name | Sequence | SEQ ID NOS. |
|---|---|---|
| THTR4/F | atg gcc acc gaa ttg gac | 51 |
| THTR4/R | cta caa agg taa agg gtt tgg tg | 52 |
| THTR5/F | atg gca acg gtg aac aca gat g | 53 |
| THTR5/R | tca cag agt ctg ccc ttt tag gt | 54 |
| THTR6/F | atg cta ggg aga tgt ttt cct cc | 55 |
| THTR6/R | tca cag agt cca ctc ttt tgg gt | 56 |
| THTR7/F | atg cta ggg aga tgt ttt cct cc | 57 |
| THTR7/R | tca cag agt ctg ccc ttt tag gt | 58 |
| THTR9/F | atg ata act ttt cta ccc atc | 59 |
| THTR9/R | cta tgg aga tga agt ctt ctc tcc | 60 |
| THTR11/F | atg tta aag gac tca gaa caa g | 61 |
| THTR11/R2 | tca gcg tgt cat ctg cca caa a | 62 |
| THTR12/F | atg atg agt ttt cta cac att g | 63 |
| THTR12/R | cta tgg agt tga ctg gtt ctg tcc | 64 |
| THTR14/F | atg aca act ttt ata ccc atc | 65 |
| THTR14/R | cta tgg aga tga agg ctt ctc tcc | 66 |
| T2R1/F | atg cta gag tct cac ctc att atc | 67 |
| T2R1/R | tca ctg aca gca ctt act gtg gag g | 68 |
| T2R3/F | atg atg gga ctc acc gag ggg g | 69 |
| T2R3/R | cta aga gaa aat ggg tcc ctt gg | 70 |
| T2R4/F | atg ctt cgg tta ttc tat ttc | 71 |
| T2R4/R | cta ttt ttt gaa aca aag aat c | 72 |
| T2R5/F | atg ctg agc gct ggc cta gga ctg | 73 |
| T2R5/R | tca tgg gcc cca gca tct ccg agc | 74 |
| T2R7/F | atg gca gat aaa gtg cag act ac | 75 |
| T2R7/R | tca gat ttg ttt atg ttg ttg ga | 76 |
| T2R8/F | atg ttc agt cct gca gat aac | 77 |
| T2R8/R | tca tat cat gca ggc aat ttt tc | 78 |
| T2R9/F | atg cca agt gca ata gag gc | 79 |
| T2R9/R | cta tgg aac aaa agg ctt tc | 80 |
| T2R10/F | atg cta cgt gta gtg gaa ggc | 81 |
| T2R10/R | cta tgt gac tct gag att ttt cc | 82 |
| T2R13/F | atg gaa agt gcc ctg ccg ag | 83 |
| T2R13/R | tca tcg ttt agc cca tac c | 84 |
| T2R14/F | atg ctc tta cag gca atg gg | 85 |
| T2R14/R | tca aga tga ttc tct aaa ttc | 86 |
| T2R16/F | atg ata ccc atc caa ctc ac | 87 |
| T2R16/R | cta gca ctt ccc ctt tag aat cc | 88 |

3. Method of Collecting Oral Cavity-Derived Tissues

In the present invention, a change in the expression level of a gustatory receptor can be detected using RNA extracted from tissues derived from the oral cavity of a subject, such as a tongue tissue sample. As stated above, the present invention is characterized in that, in the test of dysgeusia, a knife is not used to collect tongue tissues, but the tongue tissues can be collected by almost painless noninvasive means (without bleeding).

Tongue tissues are collected by a scratch method. In this case, a sterile disposable microcentrifuge tube generally called "Eppendorf tube" can be used. Tongue tissues existing in the dorsum of tongue, fungiform papilla or foliate papilla of the tongue, or intraoral mucosal tissues existing in the backside of the cheek (Igaku Shoin, *Keito Kango-gaku Koza, Senmon Kiso* 1, *Jintai no Kozo to Kinou [1], Kaibo-seiri-gaku* (Systematic Nursing Science Seminar, Professional Base 1, Structure and Function of Human Body [1], Anatomical Physiology), written by Shigeaki Hinohara) were scratched 1 to 10 time, preferably 2 to 7 times, and more preferably 2 to 5 times, using the flange (edge) portion of a cap of the aforementioned tube, so as to obtain tissues from the tongue surface layer or the cheek. A site, from which such tissues are collected, is preferably around foliate papilla. After such tissues are collected from such a site by scratching, the site is preferably left for 2 or 3 days without collecting the tissues therefrom. The microcentrifuge tube is commercially available, and it can be purchased from companies such as Eppendorf or Assist. An unsterilized centrifugation tube may be purchased and may be then sterilized with an autoclave. Otherwise, a centrifugation tube, which has been sterilized, may be purchased. It is preferable that a centrifugation tube, which has been used once, be discarded, and that it be not reused for the purpose of collecting tongue tissues.

A tongue tissue sample is collected after the oral cavity has been fully washed with water or the like. Immediately after such a tissue sample is collected, 0.5 ml of an RNA extraction reagent such as TRIzol is added to the tube, followed by stirring and blending. Thereafter, the mixture can be conserved at −20° C. before use.

4. Method of Detecting Gustatory Receptor

Total RNA or mRNA is extracted from the tissues collected by the method described in the above "2. Method of collecting oral cavity-derived tissues" section. Thereafter, RT-PCR is performed. At the time, in order to extract RNA from the tissues, TRIzol (Invitrogen), Quick Prep Total RNA Extraction Kit (Amersham Biosciences), or RNeasy Kit (QIAGEN), can be used, for example. The obtained RNA is appropriately dissolved in DEPC-treated water (DEPC treated Water (Invitrogen), for example), and the concentration thereof is then measured. Thereafter, it can also be conserved at −80° C.

In addition, for a reverse transcription reaction, SuperScript III (Invitrogen) can be used as reverse transcriptase, and a random primer, an Oligo dT primer, a sequence-specific primer, or the like, can be used as a primer. Such a reverse transcription reaction may be carried out in accordance with a manual attached to the aforementioned enzyme.

In a PCR reaction, Ex Taq can be used as DNA polymerase. As primers used in the PCR reaction, those described in the aforementioned "1 Taste substance-reactive composition (gustatory receptor)" section (the primers as shown in Table 2, for example), can be used, for example. Conditions for PCR can be appropriately determined by persons skilled in the art in accordance with known methods. For example, PCR can be carried out under conditions wherein a reaction solution is treated at 94° C. for 3 minutes, thereafter, a cycle consisting of 94° C., 30 seconds, 59° C., 30 seconds, and 72°

C., 1 minute, is repeated 35 time, thereafter, the resultant is treated at 72° C. for 7 minutes, and thereafter, the reaction is terminated at 4° C.

The method of carrying out RT-PCR of the present invention has two features. One feature is that 35 or more cycles are performed in the PCR. The other feature is that a receptor used as an amplification target is specifically and reliably amplified and detected.

With regard to the number of cycles applied in PCR, it has been known that, concerning the relationship between the number of cycles applied in PCR and the amount of a PCR product, the PCR product is first increased in an exponential manner, but that the PCR product reaches a plateau around 35 cycles (Shujunsha Co., Ltd., *Bio Jikken Illustrated* 3, *Hontou nifueru PCR* (Bio Experiment Illustrated 3, Real Amplification in PCR), written by Hiroki Nakayama). In the present invention, if PCR is performed in 35 or more cycles, the reaction product (PCR product) reaches a plateau regardless of the initial amount of a template, and thus it has a certain value (Shujunsha Co., Ltd., *Bio Jikken Illustrated* 3, *Hontou ni fueru PCR* (Bio Experiment Illustrated 3, Real Amplification in PCR), written by Hiroki Nakayama). Accordingly, it becomes more important to examine the presence or absence of the expression of such gustatory receptor RNA, than to examine the expression level of gustatory receptor RNA in the tissues. That is to say, in the case of the expression of the gustatory receptor, quantitative is not considered so much, but qualitative detection is mainly considered. Therefore, it can be interpreted that a PCR product, which is seen as a thin band at the stage of detection of the PCR reaction product (the stage of detecting the PCR product using 2100 Bioanalyzer manufactured by Agilent, for example), is hardly expressed. That is, a characteristic of the present invention is that the expression of a gustatory receptor is qualitatively examined using a reaction product wherein the amount of a PCR product has reached a plateau. As stated above, in the present invention, the cycle number applied in the PCR is 35 to 50 cycles, preferably 35 to 40 cycles, and more preferably 35 cycles.

Subsequently, reliable, specific amplification and detection of a receptor used as a target of amplification is essential when the presence or absence of the expression of a receptor family having high homology is detected by the PCR method. In order to confirm that an amplification product is a receptor as a target but is not another non-target receptor, several methods may be applied. For example, the analysis of the nucleotide sequence of the amplification product, amplification of the entire length of a receptor as a target by the PCR method, adoption of the base length to be amplified that differs for every receptor, etc., may be applied. At least a portion of a gene encoding such a gustatory receptor may be amplified. Among others, in terms of the easiness of primer design or prevention of amplification of similar nucleotide sequences, it is desired to amplify the entire length of a gene by the PCR method.

If the entire length of a gustatory receptor as a target is amplified by PCR, it is difficult to check the amplified PCR product itself. Therefore, the entire length of a gustatory receptor as a target should be amplified by the RT-PCR method, so as to confirm that normal amplification has been conducted and that the gustatory receptor as an amplification target has been certainly amplified, using the size of the amplified PCR product as an indicator. In addition, when the entire length is amplified, unless RNA that corresponds to the entire length of a gustatory receptor as a detection target exists in sample RNA, amplification is not successfully conducted. Thus, when the entire length is amplified, check is more reliably carried out than the case of amplifying at least a portion of a gustatory receptor gene. Moreover, when a trace amount of the RNA of a gustatory receptor that is not a detection target exists in a sample, amplification of such a trace amount of receptor gene becomes more difficult than amplification of a gustatory receptor as a detection target that is expressed in a large amount. Thus, amplification of the entire length of a gustatory receptor by the PCR method is more advantageous for the qualitative measurement of a gustatory receptor on the tongue, which is an object of the present invention. Accordingly, PCR primers are preferably designed such that they can amplify the coding region of a receptor as a whole (as mentioned above).

In order to measure the size or amount of a PCR product, a method comprising electrophoresing a PCR product by agarose gel electrophoresis, separating it depending on the size thereof, and measuring it depending on the thickness of a band, a method of measuring the molecular weight of a fragment contained in a PCR product using DNA LabChip (Agilent Technologies), or other methods, may be applied. Among others, 2100 Bioanalyzer manufactured by Agilent enables precise measurement of the size of a PCR product with high sensitivity, and thus it is effective for the test of the present invention. Using the thickness of the band of the thus obtained PCR product and/or the number thereof as an indicator, in the present invention, the presence or absence of dysgeusia is examined based on the fact that a gustatory receptor is not expressed. That is to say, when the expression of 10 different receptors is examined among multiple THTR receptors and T2R receptors, for example, if a certain number of thick bands of PCR products appear, or if a certain number of thick bands do not appear, it is determined that dysgeusia, glossalgia, or a state of stress has occurred. Since PCR is conducted until the PCR reaction product reaches a plateau in the present invention, it is considered that almost no receptors are expressed in the case of a PCR product that is seen as a thin band. Accordingly, such a thin band is not counted as a number of bands appeared.

The term "thin band" is used to mean a band having a peak area value (peak area) of 10 or smaller. In the present invention, 2100 Bioanalyzer manufactured by Agilent is used to measure the base length of a PCR product and the amount of a gene product amplified. 2100 Bioanalyzer is a device for electrophoresing a gene product such as a product amplified by PCR or the like and measuring the amount and base length thereof. This measurement device is used to obtain a base length (size) based on the time required until a gene product electrophoresing in a capillary due to electrical power passes through a detector and to indicate the size of a peak area indicating the strength of a signal detected by the detector as the thickness of a band. 2100 Bioanalyzer indicates the size of the peak area of a gene product signal as a pseudo-electropherogram of the expression pattern of a gustatory receptor gene. When the value of a peak area recorded during the measurement of such pseudo-electropherogram is 20 or greater, it is shown as a thick clear band. Thus, such a band is expressed as a "thick band" in the present invention, and it is determined that a gustatory receptor gene is expressed in tongue epithelial tissues. On the other hand, when such a peak area value is 5 or smaller, it is expressed as an extremely thin band, and it shows that almost no gustatory receptor genes are expressed in the present invention. When a value between 5 and 10 is obtained, the expression "only a low level of expression" is used. However, in this case, since gustatory receptor genes are expressed but a small number of receptors are expressed in tissues, it is assumed that such receptors do not function as gustatory receptors. In the case of a small peak that is not recognized by analysis software constituting 2100

Bioanalyzer, it is determined that no gustatory receptor genes are expressed. When this case is used for a mass examination of gustatory sense, if a peak area value is 10 or smaller, it may be determined that "no gustatory receptor genes are expressed (although there is gene expression, it does not have the function of feeling taste)."

5. Relationship Between Serum Zinc Level and Gene Expression Level

The present invention relates to a method for testing zinc deficiency dysgeusia. Accordingly, in the present invention, the expression level of the aforementioned gustatory receptor gene is measured, and at the same time, the serum zinc level of a patient is also measured. Thus, whether or not the patient suffers from dysgeusia can be determined by correlating the gene expression level with the serum zinc level.

Such a serum zinc level can be measured from the serum of the patient by a known method (e.g. an atomic absorption method). The normal level of zinc in serum is 65 to 110 µg/100 ml (http://www.mbcl.co.jp/compendium/main.asp?field=01&m class=09&s_class=0015; please refer to a practical guide of characteristics to be tested, Mitsubishi Chemical BCL).

It is to be noted that the normal level of zinc in serum is found to be 64 to 111 µg/100 ml by Mitsubishi Chemical BCL. An excessive level of zinc in serum hardly occurs in clinical sites. In contrast, there are far more pathologic conditions associated with a decrease in the zinc level in serum, and such pathologic conditions are considered to be serious. Zinc deficiency provokes various types of disorders such as growth and development disorder, gonadal failure, cutaneous lesion, or dysgeusia/dysosmia. Further, the relationship between serum zinc deficiency and dysgeusia has previously been well known. In accordance with the practical guide, as clinical significance, zinc is a typical, essential, trace metal existing in serum. The aforementioned practical guide describes that such serum zinc deficiency causes dermatitis or dysgeusia, and that the measurement of such a serum zinc level is important for the diagnosis of zinc deficiency disorders associated with central venous nutrition/enteral feeding.

Hence, in the present invention, if such a serum zinc level is low and if the majority of an electrophoretic band exhibiting the expression of a gustatory receptor gene on the tongue is not observed, the patient can be determined to have zinc deficiency dysgeusia. In a case where a serum zinc level is low and where a thin band is observed in the electrophoretogram of the present case although the thickness of the band of a PCR product is unbalanced, it can be determined that the patient is likely to have zinc deficiency dysgeusia.

6. Kit

The primer of the present invention can be provided as a kit for testing zinc deficiency dysgeusia. The test kit of the present invention (hereinafter referred to as "the present kit") comprises components useful for carrying out the test method of the present invention, as well as a primer. Examples of such components may include the following (a) to (c):

(a) Instruments or Reagents Used when Total RNA is Extracted from Tissues

TRIzol solution, 1-mL disposable syringe with needle (e.g. top, disposable top plastic syringe 25 G×1" R.B.), isopropanol, 70% ethanol for rinsing, and RNase free DEPC treated Water The reagents and instruments described in (a) above are used as follows. 0.5 to 1 ml (preferably 0.5 ml) of a TRIzol solution per sample is placed in a tube that contains an oral sample, and the tube is then intensively stirred, so as to blend the oral sample attached to the cap of the tube with TRIzol. Thereafter, using the syringe, the oral sample in TRIzol is strongly sucked and discharged approximately 20 to 30 times in the tube, so as to facilitate extraction of RNA from the sample. Isopropanol is used in an amount that is half of the used TRIzol, so as to precipitate RNA. A tube used for such RNA precipitation is preferably RNase free. 70% ethanol for rinsing is used to rinse total RNA precipitated with isopropanol. RNase free DEPC treated Water is used to dissolve the obtained total RNA.

(b) Instruments and Reagents Used for Reverse Transcription of Total RNA

Reaction tube (DNase RNase free tube), dNTP, Random primer mixture, reverse transcription buffer, RNase Inhibitor, DTT, reverse transcriptase (preferably, SuperScript III (Invitrogen)), and RNase H (c) Instruments and Reagents Used to Carry Out PCR Reaction Reaction tube (DNase RNase free tube), PCR reaction buffer, dNTP solution, DNase-RNase free water, DNA polymerase (preferably, Ex Taq, Takara)

Examples of the aforementioned buffer may include a phosphate buffer and a Tris-HCl buffer (pH 4 to 10). Such buffer may comprise a surfactant such as SDS. Moreover, the present kit may also comprise a microcentrifuge tube for collecting an oral sample by the scratch method, a column for extracting RNA from the sample, a buffer, a surfactant, etc.

Using the present kit, the method for testing dysgeusia, method for testing glossalgia, and method for testing stress of the present invention can be easily carried out.

The present invention will be more specifically described in the following examples. However, the following examples are not intended to limit the technical scope of the present invention.

Example 1

Amplification of Gustatory Receptor Gene (1) Method of Collecting Tissues

The left and right foliate papillae of a subject were collected by scratching 2 or 3 times with the flange (edge) portion of the cap of an Eppendorf tube.

Immediately after the aforementioned collection of tissues, 0.5 ml of TRIzol of Invitrogen was added to such tissues, and they were fully stirred and blended. Thereafter, the obtained mixture was conserved at −20° C. before use.

(2) RNA Extraction Method

Total RNA was extracted from the collected tissues. Extraction was conducted in accordance with a manual included with TRIzol. The obtained total RNA was dissolved in 10 µl of DEPC treated water (Invitrogen), and the concentration of the obtained total RNA was then measured, followed by conservation at −80° C.

(3) RT-PCR Method 0.65 µg of the obtained total RNA and a random primer (Invitrogen) were subjected to a reverse transcription reaction using Super Script III (Invitrogen). 0.5 µl of the obtained reaction solution was used as a template, and PCR was carried out in 50 µl of a reaction system using Ex Taq (Takara).

With regard to the THTR family genes, the PCR was performed on THTR11, THTR4 and THTR9, and with regard to the T2R family genes, the PCR was performed on T2R3, T2R8, T2R9, T2R10, T2R13 and T2R16. The used primers are shown in Table 2. Both the reverse transcription reaction and the PCR reaction were carried out in accordance with a manual included therewith. For PCR, GeneAmp PCR System 9700 manufactured by Applied Biosystems was used. PCR conditions consisted of a reaction at 94° C. for 3 minutes, 35 cycles of 94° C.-30 seconds, 59° C.-30 seconds, and 72° C.-1 minute, and a treatment at 72° C. for 7 minutes. Thereafter, the reaction product was then conserved at 4° C., until the measurement was carried out using 2100 Bioanalyzer of Agilent.

(4) Examination of PCR Product

The PCR product obtained under the aforementioned conditions was examined using 2100 Bioanalyzer of Agilent.

(5) Results (5-1) Comparisons Regarding Expression Frequencies of Gustatory Receptor Genes Based on the Causes of Dysgeusia Patients suffering from dysgeusia were classified into those having zinc deficiency dysgeusia, idiopathic dysgeusia, influenza-induced dysgeusia, and drug-induced dysgeusia (FIG. 1).

The age distribution and sex of the subjects are as shown in Table 3.

TABLE 3

| Age distribution | | Sex | |
|---|---|---|---|
| 21-30 | 1 subject | Male | Female |
| 31-40 | 3 subjects | | |
| 41-50 | 3 subjects | 7 subjects | 16 subjects |
| 51-60 | 5 subjects | | |
| 61-70 | 7 subjects | | |
| 71-80 | 4 subjects | | |

The type of dysgeusia and the number of cases are as follows.

Zinc deficiency dysgeusia: 9 cases (39%)
Idiopathic dysgeusia: 7 cases (31%)
Influenza-induced dysgeusia: 3 cases (13%)
Drug-induced dysgeusia: 4 cases (17%)

Each of the aforementioned types of dysgeusia was determined as follows. It is to be noted that the type of dysgeusia was determined by a filter disk method.

Zinc deficiency dysgeusia: A type of dysgeusia determined by the filter disk method, which exhibits a low serum zinc level.

Drug-induced dysgeusia: A type of dysgeusia determined by the filter disk method, to the subject of which a drug causing dysgeusia (e.g. an antihypertensive agent exhibiting antagonism to serum calcium) has been administered.

Influenza-induced dysgeusia: A type of dysgeusia determined by the filter disk method, the subject of which has been infected with influenza.

Idiopathic dysgeusia: A type of dysgeusia determined by the filter disk method, which is not induced by the aforementioned causes.

RT-PCT was carried out regarding a gustatory receptor gene expressing in the tongue tissues of each patient. Based on the results of the electrophoresis, whether or not a clear band of the PCR product was expressed was analyzed. When only a thin band (a band like a line traced weakly with a pencil with hard lead of 3H or 4H, for example) was seen by visual observation, it was determined that the gustatory receptor gene was hardly expressed. The expression frequency (%) of thick, clear bands (bands like lines traced strongly with a pencil with soft lead of 2B or 3B, for example) is as shown in FIG. 1.

In FIG. 1, the four parts of the bar graph used for individual receptor genes or receptor candidate genes indicate the causes of dysgeusia, namely, zinc deficiency dysgeusia, idiopathic dysgeusia, influenza-induced dysgeusia, and drug-induced dysgeusia, from the left.

In FIG. 1, the THTR4 gustatory receptor candidate gene was not expressed in all the 9 cases of zinc deficiency dysgeusia patients, whereas the T2R3 gustatory receptor gene was expressed in 3 out of the 9 cases. FIG. 1 shows that, particularly in the zinc deficiency dysgeusia cases, the expression frequency of a gustatory receptor gene in the tongue tissues is likely to be lower than in other types of dysgeusia cases. These results demonstrated that the method of the present invention can be used in the diagnosis of zinc deficiency dysgeusia.

(5-2) Comparisons Regarding Expression Frequencies of Gustatory Receptor Genes During Treatment of Zinc Deficiency Dysgeusia Cases Patients suffering from zinc deficiency dysgeusia were treated by administration of a zinc preparation. Every 5 weeks, a test of gustatory sense was carried out by a filter disk method, and the expression of a gustatory receptor gene in tongue tissues was analyzed.

Figure 2:
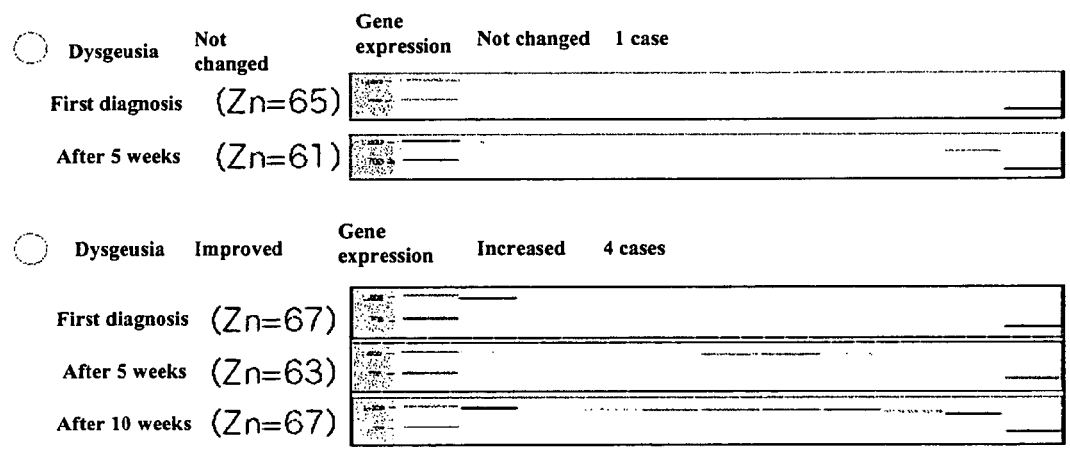
FIG. 2 is a view showing the results obtained by making comparisons regarding the expression frequencies of gustatory receptor genes during the treatment of zinc deficiency dysgeusia cases.

The results are shown in FIG. 2. FIG. 2 is a view showing the results obtained by comparing the expression frequencies of gustatory receptor genes during the treatment of the zinc deficiency dysgeusia cases (the results of electrophoresis). The number in the parentheses indicates a zinc level in serum.

The electrophoretic bands indicate the expression conditions of a DNA size marker, 3 types of gustatory receptor gene THTR family, THTR11, THTR4 and THTR9, and 6 types of T2R family, T2R3, T2R8, T2R9, T2R10, T2R13 and T2R16, from the left of the figure. The rightmost band indicates the expression of β-actin selected as a gene for checking a reverse transcription reaction.

As shown in the upper case of FIG. 2, in one case where dysgeusia was not improved, the expression frequency of a gustatory receptor gene was not changed. In contrast, in four cases where dysgeusia was improved, as shown in the lower case of FIG. 2, the expression frequency of a gustatory receptor gene was increased as a zinc preparation was continuously administered, and thus it demonstrated that the therapeutic effects were reflected.

Accordingly, it was demonstrated that the method of the present invention can be used in the prognosis of zinc deficiency dysgeusia cases.

[Sequence Listing Free Text]

SEQ ID NOS: 45 to 88: primers

The invention claimed is:

1. A method for testing zinc deficiency dysgeusia, comprising:
   testing a sample from the oral cavity of a subject to determine the expression level of at least one gene encoding a gustatory receptor belonging to the THTR family and/or at least one gene encoding a gustatory receptor belonging to the T2R family;
   testing a serum sample of the subject to determine the serum zinc level; and
   correlating the gene expression levels of said gene or genes with the serum zinc level.

2. The method according to claim 1, wherein the gustatory receptor belonging to the THTR family is selected from the group consisting of THTR 1, 2, 3, 4, 5, 6, 7, 9, 11, 12, and 14.

3. The method according to claim 1, wherein the gustatory receptor belonging to the THTR family is a polypeptide described in (a) or (b) below:
   (a) a polypeptide having the amino acid sequence as shown in SEQ ID NO: 2, 4, 6, 8, 10, 12, 14, 16, 18, 20, or 22; or
   (b) a polypeptide having an amino acid sequence comprising a deletion, substitution, or addition of one or several amino acids with respect to the amino acid sequence as shown in SEQ ID NO: 2, 4, 6, 8, 10, 12, 14, 16, 18, 20, or 22, and functioning as a gustatory receptor.

4. The method according to claim 1, wherein the gustatory receptor belonging to the THTR family is a polypeptide encoded by DNA described in (a) or (b) below:
   (a) DNA having the nucleotide sequence as shown in SEQ ID NO: 1, 3, 5, 7, 9, 11, 13, 15, 17, 19, or 21; or
   (b) DNA hybridizing with DNA having the nucleotide sequence fully complementary to the DNA having the nucleotide sequence as shown in SEQ ID NO: 1, 3, 5, 7, 9, 11, 13, 15, 17, 19, or 21 under stringent conditions, and encoding a polypeptide functioning as a gustatory receptor.

5. The method according to claim 1, wherein the gustatory receptor belonging to the T2R family is selected from the group consisting of T2R 1, 3, 4, 5, 7, 8, 9, 10, 13, 14, and 16.

6. The method according to claim 1, wherein the gustatory receptor belonging to the T2R family is a polypeptide described in (a) or (b) below:
   (a) a polypeptide having the amino acid sequence as shown in SEQ ID NO: 24, 26, 28, 30, 32, 34, 36, 38, 40, 42, or 44; or
   (b) a polypeptide having an amino acid sequence comprising a deletion, substitution, or addition of one or several amino acids with respect to the amino acid sequence as shown in SEQ ID NO: 24, 26, 28, 30, 32, 34, 36, 38, 40, 42, or 44, and functioning as a gustatory receptor.

7. The method according to claim 1, wherein the gustatory receptor belonging to the T2R family is a polypeptide encoded by DNA described in (a) or (b) below:
   (a) DNA having the nucleotide sequence as shown in SEQ ID NO: 23, 25, 27, 29, 31, 33, 35, 37, 39, 41, or 43; or
   (b) DNA hybridizing with DNA having the nucleotide sequence fully complementary to the DNA having the nucleotide sequence as shown in SEQ ID NO: 23, 25, 27, 29, 31, 33, 35, 37, 39, 41, or 43 under stringent conditions, and encoding a polypeptide functioning as a gustatory receptor.

8. The method according to claim 1, wherein the sample derived from the oral cavity is a tongue tissue sample collected by a scratch method.

9. The method according to claim 1, wherein the expression level of the at least one gustatory receptor gene is tested by amplifying the entire length of a gustatory receptor mRNA by RT-PCR.

* * * * *

SEQUENCE LISTING

```
<160> NUMBER OF SEQ ID NOS: 88

<210> SEQ ID NO 1
<211> LENGTH: 1002
<212> TYPE: DNA
<213> ORGANISM: Homo sapiens
<220> FEATURE:
<221> NAME/KEY: CDS
```

<222> LOCATION: (1)..(1002)

<400> SEQUENCE: 1

| | | | | | | | | | | | | | | | | |
|---|---|---|---|---|---|---|---|---|---|---|---|---|---|---|---|---|
| atg | ttg | act | cta | act | cgc | atc | cgc | act | gtg | tcc | tat | gaa | gtc | agg | agt | 48 |
| Met | Leu | Thr | Leu | Thr | Arg | Ile | Arg | Thr | Val | Ser | Tyr | Glu | Val | Arg | Ser | |
| 1 | | | | 5 | | | | | 10 | | | | | 15 | | |

| | | | | | | | | | | | | | | | | |
|---|---|---|---|---|---|---|---|---|---|---|---|---|---|---|---|---|
| aca | ttt | ctg | ttc | att | tca | gtc | ctg | gag | ttt | gca | gtg | ggg | ttt | ctg | acc | 96 |
| Thr | Phe | Leu | Phe | Ile | Ser | Val | Leu | Glu | Phe | Ala | Val | Gly | Phe | Leu | Thr | |
| | | | 20 | | | | | 25 | | | | | 30 | | | |

| | | | | | | | | | | | | | | | | |
|---|---|---|---|---|---|---|---|---|---|---|---|---|---|---|---|---|
| aat | gcc | ttc | gtt | ttc | ttg | gtg | aat | ttt | tgg | gat | gta | gtg | aag | agg | cag | 144 |
| Asn | Ala | Phe | Val | Phe | Leu | Val | Asn | Phe | Trp | Asp | Val | Val | Lys | Arg | Gln | |
| | | 35 | | | | | 40 | | | | | 45 | | | | |

| | | | | | | | | | | | | | | | | |
|---|---|---|---|---|---|---|---|---|---|---|---|---|---|---|---|---|
| gca | ctg | agc | aac | agt | gat | tgt | gtg | ctg | ctg | tgt | ctc | agc | atc | agc | cgg | 192 |
| Ala | Leu | Ser | Asn | Ser | Asp | Cys | Val | Leu | Leu | Cys | Leu | Ser | Ile | Ser | Arg | |
| | 50 | | | | | 55 | | | | | 60 | | | | | |

| | | | | | | | | | | | | | | | | |
|---|---|---|---|---|---|---|---|---|---|---|---|---|---|---|---|---|
| ctt | ttc | ctg | cat | gga | ctg | ctg | ttc | ctg | agt | gct | atc | cag | ctt | acc | cac | 240 |
| Leu | Phe | Leu | His | Gly | Leu | Leu | Phe | Leu | Ser | Ala | Ile | Gln | Leu | Thr | His | |
| 65 | | | | | 70 | | | | | 75 | | | | | 80 | |

| | | | | | | | | | | | | | | | | |
|---|---|---|---|---|---|---|---|---|---|---|---|---|---|---|---|---|
| ttc | cag | aag | ttg | agt | gaa | cca | ctg | aac | cac | agc | tac | caa | gcc | atc | atc | 288 |
| Phe | Gln | Lys | Leu | Ser | Glu | Pro | Leu | Asn | His | Ser | Tyr | Gln | Ala | Ile | Ile | |
| | | | | 85 | | | | | 90 | | | | | 95 | | |

| | | | | | | | | | | | | | | | | |
|---|---|---|---|---|---|---|---|---|---|---|---|---|---|---|---|---|
| atg | cta | tgg | atg | att | gca | aac | caa | gcc | aac | ctc | tgg | ctt | gct | gcc | tgc | 336 |
| Met | Leu | Trp | Met | Ile | Ala | Asn | Gln | Ala | Asn | Leu | Trp | Leu | Ala | Ala | Cys | |
| | | | 100 | | | | | 105 | | | | | 110 | | | |

| | | | | | | | | | | | | | | | | |
|---|---|---|---|---|---|---|---|---|---|---|---|---|---|---|---|---|
| ctc | agc | ctg | ctt | tac | tgc | tcc | aag | ctc | atc | cgt | ttc | tct | cac | acc | ttc | 384 |
| Leu | Ser | Leu | Leu | Tyr | Cys | Ser | Lys | Leu | Ile | Arg | Phe | Ser | His | Thr | Phe | |
| | | | 115 | | | | | 120 | | | | | 125 | | | |

| | | | | | | | | | | | | | | | | |
|---|---|---|---|---|---|---|---|---|---|---|---|---|---|---|---|---|
| ctg | atc | tgc | ttg | gca | agc | tgg | gtc | tcc | agg | aag | atc | tcc | cag | atg | ctc | 432 |
| Leu | Ile | Cys | Leu | Ala | Ser | Trp | Val | Ser | Arg | Lys | Ile | Ser | Gln | Met | Leu | |
| | | 130 | | | | | 135 | | | | | 140 | | | | |

| | | | | | | | | | | | | | | | | |
|---|---|---|---|---|---|---|---|---|---|---|---|---|---|---|---|---|
| ctg | ggt | att | att | ctt | tgc | tcc | tgc | atc | tgc | act | gtc | ctc | tgt | gtt | tgg | 480 |
| Leu | Gly | Ile | Ile | Leu | Cys | Ser | Cys | Ile | Cys | Thr | Val | Leu | Cys | Val | Trp | |
| 145 | | | | | 150 | | | | | 155 | | | | | 160 | |

| | | | | | | | | | | | | | | | | |
|---|---|---|---|---|---|---|---|---|---|---|---|---|---|---|---|---|
| tgc | ttt | ttt | agc | aga | cct | cac | ttc | aca | gtc | aca | act | gtg | cta | ttc | atg | 528 |
| Cys | Phe | Phe | Ser | Arg | Pro | His | Phe | Thr | Val | Thr | Thr | Val | Leu | Phe | Met | |
| | | | | 165 | | | | | 170 | | | | | 175 | | |

| | | | | | | | | | | | | | | | | |
|---|---|---|---|---|---|---|---|---|---|---|---|---|---|---|---|---|
| aat | aac | aat | aca | agg | ctc | aac | tgg | cag | att | aaa | gat | ctc | aat | tta | ttt | 576 |
| Asn | Asn | Asn | Thr | Arg | Leu | Asn | Trp | Gln | Ile | Lys | Asp | Leu | Asn | Leu | Phe | |
| | | | 180 | | | | | 185 | | | | | 190 | | | |

| | | | | | | | | | | | | | | | | |
|---|---|---|---|---|---|---|---|---|---|---|---|---|---|---|---|---|
| tat | tcc | ttt | ctc | ttc | tgc | tat | ctg | tgg | tct | gtg | cct | cct | ttc | cta | ttg | 624 |
| Tyr | Ser | Phe | Leu | Phe | Cys | Tyr | Leu | Trp | Ser | Val | Pro | Pro | Phe | Leu | Leu | |
| | | | | 195 | | | | | 200 | | | | | 205 | | |

| | | | | | | | | | | | | | | | | |
|---|---|---|---|---|---|---|---|---|---|---|---|---|---|---|---|---|
| ttt | ctg | gtt | tct | tct | ggg | atg | ctg | act | gtc | tcc | ctg | gga | agg | cac | atg | 672 |
| Phe | Leu | Val | Ser | Ser | Gly | Met | Leu | Thr | Val | Ser | Leu | Gly | Arg | His | Met | |
| | 210 | | | | | 215 | | | | | 220 | | | | | |

| | | | | | | | | | | | | | | | | |
|---|---|---|---|---|---|---|---|---|---|---|---|---|---|---|---|---|
| agg | aca | atg | aag | gtc | tat | acc | aga | aac | tct | cgt | gac | ccc | agc | ctg | gag | 720 |
| Arg | Thr | Met | Lys | Val | Tyr | Thr | Arg | Asn | Ser | Arg | Asp | Pro | Ser | Leu | Glu | |
| 225 | | | | | 230 | | | | | 235 | | | | | 240 | |

| | | | | | | | | | | | | | | | | |
|---|---|---|---|---|---|---|---|---|---|---|---|---|---|---|---|---|
| gcc | cac | att | aaa | gcc | ctc | aag | tct | ctt | gtc | tcc | ttt | ttc | tgc | ttc | ttt | 768 |
| Ala | His | Ile | Lys | Ala | Leu | Lys | Ser | Leu | Val | Ser | Phe | Phe | Cys | Phe | Phe | |
| | | | | 245 | | | | | 250 | | | | | 255 | | |

| | | | | | | | | | | | | | | | | |
|---|---|---|---|---|---|---|---|---|---|---|---|---|---|---|---|---|
| gtg | ata | tca | tcc | tgt | gtt | gcc | ttc | atc | tct | gtg | ccc | cta | ctg | att | ctg | 816 |
| Val | Ile | Ser | Ser | Cys | Val | Ala | Phe | Ile | Ser | Val | Pro | Leu | Leu | Ile | Leu | |
| | | | 260 | | | | | 265 | | | | | 270 | | | |

| | | | | | | | | | | | | | | | | |
|---|---|---|---|---|---|---|---|---|---|---|---|---|---|---|---|---|
| tgg | cgc | gac | aaa | ata | ggg | gtg | atg | gtt | tgt | gtt | ggg | ata | atg | gca | gct | 864 |
| Trp | Arg | Asp | Lys | Ile | Gly | Val | Met | Val | Cys | Val | Gly | Ile | Met | Ala | Ala | |
| | | 275 | | | | | 280 | | | | | 285 | | | | |

| | | | | | | | | | | | | | | | | |
|---|---|---|---|---|---|---|---|---|---|---|---|---|---|---|---|---|
| tgt | ccc | tct | ggg | cat | gca | gcc | atc | ctg | atc | tca | ggc | aat | gcc | aag | ttg | 912 |
| Cys | Pro | Ser | Gly | His | Ala | Ala | Ile | Leu | Ile | Ser | Gly | Asn | Ala | Lys | Leu | |
| | 290 | | | | | 295 | | | | | 300 | | | | | |

```
agg aga gct gtg atg acc att ctg ctc tgg gct cag agc agc ctg aag    960
Arg Arg Ala Val Met Thr Ile Leu Leu Trp Ala Gln Ser Ser Leu Lys
305                 310                 315                 320 gta aga gcc gac cac aag gca gat tcc cgg aca ctg tgc tga            1002
Val Arg Ala Asp His Lys Ala Asp Ser Arg Thr Leu Cys
                325                 330
```

<210> SEQ ID NO 2
<211> LENGTH: 333
<212> TYPE: PRT
<213> ORGANISM: Homo sapiens

<400> SEQUENCE: 2

```
Met Leu Thr Leu Thr Arg Ile Arg Thr Val Ser Tyr Glu Val Arg Ser
1               5                   10                  15

Thr Phe Leu Phe Ile Ser Val Leu Glu Phe Ala Val Gly Phe Leu Thr
            20                  25                  30

Asn Ala Phe Val Phe Leu Val Asn Phe Trp Asp Val Val Lys Arg Gln
        35                  40                  45

Ala Leu Ser Asn Ser Asp Cys Val Leu Cys Leu Ser Ile Ser Arg
    50                  55                  60

Leu Phe Leu His Gly Leu Leu Phe Leu Ser Ala Ile Gln Leu Thr His
65                  70                  75                  80

Phe Gln Lys Leu Ser Glu Pro Leu Asn His Ser Tyr Gln Ala Ile Ile
                85                  90                  95

Met Leu Trp Met Ile Ala Asn Gln Ala Asn Leu Trp Leu Ala Ala Cys
            100                 105                 110

Leu Ser Leu Leu Tyr Cys Ser Lys Leu Ile Arg Phe Ser His Thr Phe
        115                 120                 125

Leu Ile Cys Leu Ala Ser Trp Val Ser Arg Lys Ile Ser Gln Met Leu
    130                 135                 140

Leu Gly Ile Ile Leu Cys Ser Cys Ile Cys Thr Val Leu Cys Val Trp
145                 150                 155                 160

Cys Phe Phe Ser Arg Pro His Phe Thr Val Thr Thr Val Leu Phe Met
                165                 170                 175

Asn Asn Asn Thr Arg Leu Asn Trp Gln Ile Lys Asp Leu Asn Leu Phe
            180                 185                 190

Tyr Ser Phe Leu Phe Cys Tyr Leu Trp Ser Val Pro Pro Phe Leu Leu
        195                 200                 205

Phe Leu Val Ser Ser Gly Met Leu Thr Val Ser Leu Gly Arg His Met
    210                 215                 220

Arg Thr Met Lys Val Tyr Thr Arg Asn Ser Arg Asp Pro Ser Leu Glu
225                 230                 235                 240

Ala His Ile Lys Ala Leu Lys Ser Leu Val Ser Phe Phe Cys Phe Phe
                245                 250                 255

Val Ile Ser Ser Cys Val Ala Phe Ile Ser Val Pro Leu Leu Ile Leu
            260                 265                 270

Trp Arg Asp Lys Ile Gly Val Met Val Cys Val Gly Ile Met Ala Ala
        275                 280                 285

Cys Pro Ser Gly His Ala Ala Ile Leu Ile Ser Gly Asn Ala Lys Leu
    290                 295                 300

Arg Arg Ala Val Met Thr Ile Leu Leu Trp Ala Gln Ser Ser Leu Lys
305                 310                 315                 320

Val Arg Ala Asp His Lys Ala Asp Ser Arg Thr Leu Cys
                325                 330
```

-continued

```
<210> SEQ ID NO 3
<211> LENGTH: 960
<212> TYPE: DNA
<213> ORGANISM: Homo sapiens
<220> FEATURE:
<221> NAME/KEY: CDS
<222> LOCATION: (1)..(960)

<400> SEQUENCE: 3 atg ata act ttt ctg ccc atc att ttt tcc att cta ata gtg gtt ata      48
Met Ile Thr Phe Leu Pro Ile Ile Phe Ser Ile Leu Ile Val Val Ile
1               5                   10                  15 ttt gtg att gga aat ttt gct aat ggc ttc ata gca ttg gta aat tcc      96
Phe Val Ile Gly Asn Phe Ala Asn Gly Phe Ile Ala Leu Val Asn Ser
            20                  25                  30 att gag tgg gtc aag aga caa aag atc tcc ttt gtt gac caa att ctc     144
Ile Glu Trp Val Lys Arg Gln Lys Ile Ser Phe Val Asp Gln Ile Leu
        35                  40                  45 act gct ctg gcg gtc tcc aga gtt ggt ttg ctc tgg gtg tta tta cta     192
Thr Ala Leu Ala Val Ser Arg Val Gly Leu Leu Trp Val Leu Leu Leu
    50                  55                  60 cat tgg tat gca act cag ttg aat cca gct ttt tat agt gta gaa gta     240
His Trp Tyr Ala Thr Gln Leu Asn Pro Ala Phe Tyr Ser Val Glu Val
65                  70                  75                  80 aga att act gct tat aat gtc tgg gca gta acc aac cat ttc agc agc     288
Arg Ile Thr Ala Tyr Asn Val Trp Ala Val Thr Asn His Phe Ser Ser
                85                  90                  95 tgg ctt gct act agc ctc agc atg ttt tat ttg ctc agg att gcc aat     336
Trp Leu Ala Thr Ser Leu Ser Met Phe Tyr Leu Leu Arg Ile Ala Asn
            100                 105                 110 ttc tcc aac ctt att ttt ctt cgc ata aag agg aga gtt aag agt gtt     384
Phe Ser Asn Leu Ile Phe Leu Arg Ile Lys Arg Arg Val Lys Ser Val
        115                 120                 125 gtt ctg gtg ata ctg ttg ggg cct ttg cta ttt ttg gtt tgt cat ctt     432
Val Leu Val Ile Leu Leu Gly Pro Leu Leu Phe Leu Val Cys His Leu
    130                 135                 140 ttt gtg ata aac atg gat gag act gta tgg aca aaa gaa tat gaa gga     480
Phe Val Ile Asn Met Asp Glu Thr Val Trp Thr Lys Glu Tyr Glu Gly
145                 150                 155                 160 aac gtg act tgg aag atc aaa ttg agg agt gca atg tac cat tca aat     528
Asn Val Thr Trp Lys Ile Lys Leu Arg Ser Ala Met Tyr His Ser Asn
                165                 170                 175 atg act cta acc atg cta gca aac ttt gta ccc ctc act ctg acc ctg     576
Met Thr Leu Thr Met Leu Ala Asn Phe Val Pro Leu Thr Leu Thr Leu
            180                 185                 190 ata tct ttt ctg ctg tta atc tgt tct ctg tgt aaa cat ctc aag aag     624
Ile Ser Phe Leu Leu Leu Ile Cys Ser Leu Cys Lys His Leu Lys Lys
        195                 200                 205 atg cag ctc cat ggc aaa gga tct caa gat ccc agc acc aag gtc cac     672
Met Gln Leu His Gly Lys Gly Ser Gln Asp Pro Ser Thr Lys Val His
    210                 215                 220 ata aaa gct ttg caa act gtg acc tcc ttt ctt ctg tta tgt gcc att     720
Ile Lys Ala Leu Gln Thr Val Thr Ser Phe Leu Leu Leu Cys Ala Ile
225                 230                 235                 240 tac ttt ctg tcc atg atc ata tca gtt tgt aat ttg ggg agg ctg gaa     768
Tyr Phe Leu Ser Met Ile Ile Ser Val Cys Asn Leu Gly Arg Leu Glu
                245                 250                 255 aag caa cct gtc ttc atg ttc tgc caa gct att ata ttc agc tat cct     816
Lys Gln Pro Val Phe Met Phe Cys Gln Ala Ile Ile Phe Ser Tyr Pro
            260                 265                 270 tca acc cac cca ttc atc ctg att ttg gga aac aag aag cta aag cag     864
Ser Thr His Pro Phe Ile Leu Ile Leu Gly Asn Lys Lys Leu Lys Gln
```

```
                    275                 280                 285 att ttt ctt tca gtt ttg cgg cat gtg agg tac tgg gtg aaa gac aga   912
Ile Phe Leu Ser Val Leu Arg His Val Arg Tyr Trp Val Lys Asp Arg
    290                 295                 300 agc ctt cgt ctc cat aga ttc aca aga ggg gca ttg tgt gtc ttc tag   960
Ser Leu Arg Leu His Arg Phe Thr Arg Gly Ala Leu Cys Val Phe
305                 310                 315

<210> SEQ ID NO 4
<211> LENGTH: 319
<212> TYPE: PRT
<213> ORGANISM: Homo sapiens

<400> SEQUENCE: 4

Met Ile Thr Phe Leu Pro Ile Ile Phe Ser Ile Leu Ile Val Val Ile
1               5                   10                  15

Phe Val Ile Gly Asn Phe Ala Asn Gly Phe Ile Ala Leu Val Asn Ser
                20                  25                  30

Ile Glu Trp Val Lys Arg Gln Lys Ile Ser Phe Val Asp Gln Ile Leu
            35                  40                  45

Thr Ala Leu Ala Val Ser Arg Val Gly Leu Leu Trp Val Leu Leu Leu
        50                  55                  60

His Trp Tyr Ala Thr Gln Leu Asn Pro Ala Phe Tyr Ser Val Glu Val
65                  70                  75                  80

Arg Ile Thr Ala Tyr Asn Val Trp Ala Val Thr Asn His Phe Ser Ser
                85                  90                  95

Trp Leu Ala Thr Ser Leu Ser Met Phe Tyr Leu Leu Arg Ile Ala Asn
            100                 105                 110

Phe Ser Asn Leu Ile Phe Leu Arg Ile Lys Arg Arg Val Lys Ser Val
        115                 120                 125

Val Leu Val Ile Leu Leu Gly Pro Leu Leu Phe Leu Val Cys His Leu
    130                 135                 140

Phe Val Ile Asn Met Asp Glu Thr Val Trp Thr Lys Glu Tyr Glu Gly
145                 150                 155                 160

Asn Val Thr Trp Lys Ile Lys Leu Arg Ser Ala Met Tyr His Ser Asn
                165                 170                 175

Met Thr Leu Thr Met Leu Ala Asn Phe Val Pro Leu Thr Leu Thr Leu
            180                 185                 190

Ile Ser Phe Leu Leu Leu Ile Cys Ser Leu Cys Lys His Leu Lys Lys
        195                 200                 205

Met Gln Leu His Gly Lys Gly Ser Gln Asp Pro Ser Thr Lys Val His
    210                 215                 220

Ile Lys Ala Leu Gln Thr Val Thr Ser Phe Leu Leu Leu Cys Ala Ile
225                 230                 235                 240

Tyr Phe Leu Ser Met Ile Ile Ser Val Cys Asn Leu Gly Arg Leu Glu
                245                 250                 255

Lys Gln Pro Val Phe Met Phe Cys Gln Ala Ile Ile Phe Ser Tyr Pro
            260                 265                 270

Ser Thr His Pro Phe Ile Leu Ile Leu Gly Asn Lys Lys Leu Lys Gln
        275                 280                 285

Ile Phe Leu Ser Val Leu Arg His Val Arg Tyr Trp Val Lys Asp Arg
    290                 295                 300

Ser Leu Arg Leu His Arg Phe Thr Arg Gly Ala Leu Cys Val Phe
305                 310                 315

<210> SEQ ID NO 5
```

```
<211> LENGTH: 900
<212> TYPE: DNA
<213> ORGANISM: Homo sapiens
<220> FEATURE:
<221> NAME/KEY: CDS
<222> LOCATION: (1)..(900)

<400> SEQUENCE: 5 atg ata act ttt ctg ccc atc ata ttt tcc att cta gta gtg gtt aca      48
Met Ile Thr Phe Leu Pro Ile Ile Phe Ser Ile Leu Val Val Val Thr
1               5                   10                  15 ttt gtt att gga aat ttt gct aat ggc ttc ata gcg ttg gta aat tcc      96
Phe Val Ile Gly Asn Phe Ala Asn Gly Phe Ile Ala Leu Val Asn Ser
            20                  25                  30 acc gag tgg gtg aag aga caa aag atc tcc ttt gct gac caa att gtc     144
Thr Glu Trp Val Lys Arg Gln Lys Ile Ser Phe Ala Asp Gln Ile Val
        35                  40                  45 act gct ctg gcg gtc tcc aga gtt ggt ttg ctc tgg gtg tta tta tta     192
Thr Ala Leu Ala Val Ser Arg Val Gly Leu Leu Trp Val Leu Leu Leu
    50                  55                  60 aat tgg tat tca act gtg ttg aat cca gct ttt tat agt gta gaa tta     240
Asn Trp Tyr Ser Thr Val Leu Asn Pro Ala Phe Tyr Ser Val Glu Leu
65                  70                  75                  80 aga act act gct tat aat atc tgg gca gta acc ggc cat ttc agc aac     288
Arg Thr Thr Ala Tyr Asn Ile Trp Ala Val Thr Gly His Phe Ser Asn
                85                  90                  95 tgg cct gct act agc ctc agc ata ttt tat ttg ctc aag att gcc aat     336
Trp Pro Ala Thr Ser Leu Ser Ile Phe Tyr Leu Leu Lys Ile Ala Asn
            100                 105                 110 ttc tcc aac ctt att ttt ctt cgc tta aag agg aga gtt aag agt gtc     384
Phe Ser Asn Leu Ile Phe Leu Arg Leu Lys Arg Arg Val Lys Ser Val
        115                 120                 125 att ctg gtg gtg ctg ttg ggg cct ttg cta ttt ttg gct tgt cat ctt     432
Ile Leu Val Val Leu Leu Gly Pro Leu Leu Phe Leu Ala Cys His Leu
    130                 135                 140 ttt gtg gta aac atg aat cag att gta tgg aca aaa gaa tat gaa gga     480
Phe Val Val Asn Met Asn Gln Ile Val Trp Thr Lys Glu Tyr Glu Gly
145                 150                 155                 160 aac atg act tgg aag atc aaa ttg agg cgt gca atg tac ctt tca gat     528
Asn Met Thr Trp Lys Ile Lys Leu Arg Arg Ala Met Tyr Leu Ser Asp
                165                 170                 175 acg act gta acc atg cta gca aac tta gta ccc ttt act gta acc ctg     576
Thr Thr Val Thr Met Leu Ala Asn Leu Val Pro Phe Thr Val Thr Leu
            180                 185                 190 ata tct ttt ctg ctg tta gtc tgt tct ctg tgt aaa cat ctc aag aag     624
Ile Ser Phe Leu Leu Leu Val Cys Ser Leu Cys Lys His Leu Lys Lys
        195                 200                 205 atg cag ctc cat ggc aaa gga tct caa gat ccc agt acc aag gtc cac     672
Met Gln Leu His Gly Lys Gly Ser Gln Asp Pro Ser Thr Lys Val His
    210                 215                 220 ata aaa gtt ttg caa act gtg atc tcc ttc ttg tta tgt gcc att        720
Ile Lys Val Leu Gln Thr Val Ile Ser Phe Phe Leu Leu Cys Ala Ile
225                 230                 235                 240 tac ttt gtg tct gta ata ata tca gtt tgg agt ttt aag aat ctg gaa     768
Tyr Phe Val Ser Val Ile Ile Ser Val Trp Ser Phe Lys Asn Leu Glu
                245                 250                 255 aac aaa cct gtc ttc atg ttc tgc caa gct att gga ttc agc tgt tct     816
Asn Lys Pro Val Phe Met Phe Cys Gln Ala Ile Gly Phe Ser Cys Ser
            260                 265                 270 tca gcc cac ccg ttc atc ctg att tgg gga aac aag aag cta aag cag     864
Ser Ala His Pro Phe Ile Leu Ile Trp Gly Asn Lys Lys Leu Lys Gln
        275                 280                 285
```

```
act tat ctt tca gtt ttg tgg caa atg agg tac tga                    900
Thr Tyr Leu Ser Val Leu Trp Gln Met Arg Tyr
    290                 295
```

<210> SEQ ID NO 6
<211> LENGTH: 299
<212> TYPE: PRT
<213> ORGANISM: Homo sapiens

<400> SEQUENCE: 6

```
Met Ile Thr Phe Leu Pro Ile Ile Phe Ser Ile Leu Val Val Thr
1               5                   10                  15

Phe Val Ile Gly Asn Phe Ala Asn Gly Phe Ile Ala Leu Val Asn Ser
                20              25                  30

Thr Glu Trp Val Lys Arg Gln Lys Ile Ser Phe Ala Asp Gln Ile Val
            35                  40                  45

Thr Ala Leu Ala Val Ser Arg Val Gly Leu Leu Trp Val Leu Leu Leu
    50                  55                  60

Asn Trp Tyr Ser Thr Val Leu Asn Pro Ala Phe Tyr Ser Val Glu Leu
65              70                  75                  80

Arg Thr Thr Ala Tyr Asn Ile Trp Ala Val Thr Gly His Phe Ser Asn
                85                  90                  95

Trp Pro Ala Thr Ser Leu Ser Ile Phe Tyr Leu Leu Lys Ile Ala Asn
            100                 105                 110

Phe Ser Asn Leu Ile Phe Leu Arg Leu Lys Arg Arg Val Lys Ser Val
        115                 120                 125

Ile Leu Val Val Leu Leu Gly Pro Leu Leu Phe Leu Ala Cys His Leu
130                 135                 140

Phe Val Val Asn Met Asn Gln Ile Val Trp Thr Lys Glu Tyr Glu Gly
145                 150                 155                 160

Asn Met Thr Trp Lys Ile Lys Leu Arg Arg Ala Met Tyr Leu Ser Asp
                165                 170                 175

Thr Thr Val Thr Met Leu Ala Asn Leu Val Pro Phe Thr Val Thr Leu
            180                 185                 190

Ile Ser Phe Leu Leu Leu Val Cys Ser Leu Cys Lys His Leu Lys Lys
        195                 200                 205

Met Gln Leu His Gly Lys Gly Ser Gln Asp Pro Ser Thr Lys Val His
210                 215                 220

Ile Lys Val Leu Gln Thr Val Ile Ser Phe Phe Leu Leu Cys Ala Ile
225                 230                 235                 240

Tyr Phe Val Ser Val Ile Ile Ser Val Trp Ser Phe Lys Asn Leu Glu
                245                 250                 255

Asn Lys Pro Val Phe Met Phe Cys Gln Ala Ile Gly Phe Ser Cys Ser
            260                 265                 270

Ser Ala His Pro Phe Ile Leu Ile Trp Gly Asn Lys Lys Leu Lys Gln
        275                 280                 285

Thr Tyr Leu Ser Val Leu Trp Gln Met Arg Tyr
290                 295
```

<210> SEQ ID NO 7
<211> LENGTH: 945
<212> TYPE: DNA
<213> ORGANISM: Homo sapiens
<220> FEATURE:
<221> NAME/KEY: CDS
<222> LOCATION: (1)..(945)

<400> SEQUENCE: 7

```
atg gcc acc gaa ttg gac aaa atc ttt ctg att ctg gca ata gca gaa      48
Met Ala Thr Glu Leu Asp Lys Ile Phe Leu Ile Leu Ala Ile Ala Glu
1               5                   10                  15 ttc atc atc agc atg ctg ggg aat gtg ttc att gga ctg gta aac tgc      96
Phe Ile Ile Ser Met Leu Gly Asn Val Phe Ile Gly Leu Val Asn Cys
            20                  25                  30 tct gaa ggg atc aag aac caa aag gtc ttc tca gct gac ttc atc ctc     144
Ser Glu Gly Ile Lys Asn Gln Lys Val Phe Ser Ala Asp Phe Ile Leu
        35                  40                  45 acc tgc ttg gct atc tcc aca att gga caa ctg ttg gtg ata ctg ttt     192
Thr Cys Leu Ala Ile Ser Thr Ile Gly Gln Leu Leu Val Ile Leu Phe
    50                  55                  60 gat tca ttt cta gtg gga ctt gct tca cat tta tat acc aca tat aga     240
Asp Ser Phe Leu Val Gly Leu Ala Ser His Leu Tyr Thr Thr Tyr Arg
65                  70                  75                  80 cta gga aaa act gtt att atg ctt tgg cac atg act aat cac ttg aca     288
Leu Gly Lys Thr Val Ile Met Leu Trp His Met Thr Asn His Leu Thr
                85                  90                  95 acc tgg ctt gcc acc tgc cta agc att ttc tat ttc ttt aag ata gcc     336
Thr Trp Leu Ala Thr Cys Leu Ser Ile Phe Tyr Phe Phe Lys Ile Ala
            100                 105                 110 cac ttc ccc cac tcc ctt ttc ctc tgg ctg agg tgg agg atg aac gga     384
His Phe Pro His Ser Leu Phe Leu Trp Leu Arg Trp Arg Met Asn Gly
        115                 120                 125 atg att gtt atg ctt ctt ata ttg tct ttg ttc tta ctg att ttt gac     432
Met Ile Val Met Leu Leu Ile Leu Ser Leu Phe Leu Leu Ile Phe Asp
    130                 135                 140 agt tta gtg cta gaa ata ttt att gat atc tca ctc aat ata ata gat     480
Ser Leu Val Leu Glu Ile Phe Ile Asp Ile Ser Leu Asn Ile Ile Asp
145                 150                 155                 160 aaa agt aat ctg act tta tat tta gat gaa agt aaa act ctc ttt gat     528
Lys Ser Asn Leu Thr Leu Tyr Leu Asp Glu Ser Lys Thr Leu Phe Asp
                165                 170                 175 aaa ctc tct att tta aaa act ctt ctc agc ttg acc agt ttt atc ccc     576
Lys Leu Ser Ile Leu Lys Thr Leu Leu Ser Leu Thr Ser Phe Ile Pro
            180                 185                 190 ttt tct ctg tcc ctg acc tcc ttg ctt ttt tta ttt ctg tcc ttg gtg     624
Phe Ser Leu Ser Leu Thr Ser Leu Leu Phe Leu Phe Leu Ser Leu Val
        195                 200                 205 aga cat act aga aat ttg aag ctc agt tcc ttg ggc tct aga gac tcc     672
Arg His Thr Arg Asn Leu Lys Leu Ser Ser Leu Gly Ser Arg Asp Ser
    210                 215                 220 agc aca gag gcc cat agg agg gcc atg aaa atg gtg atg tct ttc ctt     720
Ser Thr Glu Ala His Arg Arg Ala Met Lys Met Val Met Ser Phe Leu
225                 230                 235                 240 ttc ctc ttc ata gtt cat ttt ttt tcc tta caa gtg gcc aat tgg ata     768
Phe Leu Phe Ile Val His Phe Phe Ser Leu Gln Val Ala Asn Trp Ile
                245                 250                 255 ttt ttt atg ttg tgg aac aac aag tac ata aag ttt gtc atg tta gcc     816
Phe Phe Met Leu Trp Asn Asn Lys Tyr Ile Lys Phe Val Met Leu Ala
            260                 265                 270 tta aat gcc ttt ccc tcg tgc cac tca ttt att ctc att ctg gga aac     864
Leu Asn Ala Phe Pro Ser Cys His Ser Phe Ile Leu Ile Leu Gly Asn
        275                 280                 285 agc aag ctg cga cag aca gct gtg agg cta ctg tgg cat ctt agg aac     912
Ser Lys Leu Arg Gln Thr Ala Val Arg Leu Leu Trp His Leu Arg Asn
    290                 295                 300 tat aca aaa aca cca aac cct tta cct ttg tag                         945
Tyr Thr Lys Thr Pro Asn Pro Leu Pro Leu
305                 310
```

<210> SEQ ID NO 8
<211> LENGTH: 314
<212> TYPE: PRT
<213> ORGANISM: Homo sapiens

<400> SEQUENCE: 8

Met Ala Thr Glu Leu Asp Lys Ile Phe Leu Ile Leu Ala Ile Ala Glu
1               5                   10                  15

Phe Ile Ile Ser Met Leu Gly Asn Val Phe Ile Gly Leu Val Asn Cys
            20                  25                  30

Ser Glu Gly Ile Lys Asn Gln Lys Val Phe Ser Ala Asp Phe Ile Leu
        35                  40                  45

Thr Cys Leu Ala Ile Ser Thr Ile Gly Gln Leu Leu Val Ile Leu Phe
    50                  55                  60

Asp Ser Phe Leu Val Gly Leu Ala Ser His Leu Tyr Thr Thr Tyr Arg
65                  70                  75                  80

Leu Gly Lys Thr Val Ile Met Leu Trp His Met Thr Asn His Leu Thr
                85                  90                  95

Thr Trp Leu Ala Thr Cys Leu Ser Ile Phe Tyr Phe Phe Lys Ile Ala
            100                 105                 110

His Phe Pro His Ser Leu Phe Leu Trp Leu Arg Trp Arg Met Asn Gly
        115                 120                 125

Met Ile Val Met Leu Leu Ile Leu Ser Leu Phe Leu Leu Ile Phe Asp
    130                 135                 140

Ser Leu Val Leu Glu Ile Phe Ile Asp Ile Ser Leu Asn Ile Ile Asp
145                 150                 155                 160

Lys Ser Asn Leu Thr Leu Tyr Leu Asp Glu Ser Lys Thr Leu Phe Asp
                165                 170                 175

Lys Leu Ser Ile Leu Lys Thr Leu Leu Ser Leu Thr Ser Phe Ile Pro
            180                 185                 190

Phe Ser Leu Ser Leu Thr Ser Leu Leu Phe Leu Phe Leu Ser Leu Val
        195                 200                 205

Arg His Thr Arg Asn Leu Lys Leu Ser Ser Leu Gly Ser Arg Asp Ser
    210                 215                 220

Ser Thr Glu Ala His Arg Arg Ala Met Lys Met Val Met Ser Phe Leu
225                 230                 235                 240

Phe Leu Phe Ile Val His Phe Phe Ser Leu Gln Val Ala Asn Trp Ile
                245                 250                 255

Phe Phe Met Leu Trp Asn Asn Lys Tyr Ile Lys Phe Val Met Leu Ala
            260                 265                 270

Leu Asn Ala Phe Pro Ser Cys His Ser Phe Ile Leu Ile Leu Gly Asn
        275                 280                 285

Ser Lys Leu Arg Gln Thr Ala Val Arg Leu Leu Trp His Leu Arg Asn
    290                 295                 300

Tyr Thr Lys Thr Pro Asn Pro Leu Pro Leu
305                 310

<210> SEQ ID NO 9
<211> LENGTH: 972
<212> TYPE: DNA
<213> ORGANISM: Homo sapiens
<220> FEATURE:
<221> NAME/KEY: CDS
<222> LOCATION: (1)..(972)

<400> SEQUENCE: 9

```
atg gca acg gtg aac aca gat gcc aca gat aaa gac ata tcc aag ttc         48
Met Ala Thr Val Asn Thr Asp Ala Thr Asp Lys Asp Ile Ser Lys Phe
1               5                   10                  15 aag gtc acc ttc act ttg gtg gtc tcc gga ata gag tgc atc act ggc         96
Lys Val Thr Phe Thr Leu Val Val Ser Gly Ile Glu Cys Ile Thr Gly
                20                  25                  30 atc ctt ggg agt ggc ttc atc acg gcc atc tat ggg gct gag tgg gcc        144
Ile Leu Gly Ser Gly Phe Ile Thr Ala Ile Tyr Gly Ala Glu Trp Ala
            35                  40                  45 agg ggc aaa aca ctc ccc act ggt gac cgc att atg ttg atg ctg agc        192
Arg Gly Lys Thr Leu Pro Thr Gly Asp Arg Ile Met Leu Met Leu Ser
        50                  55                  60 ttt tcc agg ctc ttg cta cag att tgg atg atg ctg gag aac att ttc        240
Phe Ser Arg Leu Leu Leu Gln Ile Trp Met Met Leu Glu Asn Ile Phe
65                  70                  75                  80 agt ctg cta ttc cga att gtt tat aac caa aac tca gtg tat atc ctc        288
Ser Leu Leu Phe Arg Ile Val Tyr Asn Gln Asn Ser Val Tyr Ile Leu
                85                  90                  95 ttc aaa gtc atc act gtc ttt ctg aac cat tcc aat ctc tgg ttt gct        336
Phe Lys Val Ile Thr Val Phe Leu Asn His Ser Asn Leu Trp Phe Ala
            100                 105                 110 gcc tgg ctc aaa gtc ttc tat tgt ctt aga att gca aac ttc aat cat        384
Ala Trp Leu Lys Val Phe Tyr Cys Leu Arg Ile Ala Asn Phe Asn His
        115                 120                 125 cct ttg ttc ttc ctg atg aag agg aaa atc ata gtg ctg atg cct tgg        432
Pro Leu Phe Phe Leu Met Lys Arg Lys Ile Ile Val Leu Met Pro Trp
130                 135                 140 ctt ctc agg ctg tca gtg ttg gtt tcc tta agc ttc agc ttt cct ctc        480
Leu Leu Arg Leu Ser Val Leu Val Ser Leu Ser Phe Ser Phe Pro Leu
145                 150                 155                 160 tcg aga gat gtc ttc aat gtg tat gtg aat agc tcc att cct atc ccc        528
Ser Arg Asp Val Phe Asn Val Tyr Val Asn Ser Ser Ile Pro Ile Pro
                165                 170                 175 tcc tcc aac tcc acg gag aag aag tac ttc tct gag acc aat atg gtc        576
Ser Ser Asn Ser Thr Glu Lys Lys Tyr Phe Ser Glu Thr Asn Met Val
            180                 185                 190 aac ctg gta ttt ttc tat aac atg ggg atc ttc gtt cct ctg atc atg        624
Asn Leu Val Phe Phe Tyr Asn Met Gly Ile Phe Val Pro Leu Ile Met
        195                 200                 205 ttc atc ctg gca gcc acc ctg ctg atc ctc tct ctc aag aga cac acc        672
Phe Ile Leu Ala Ala Thr Leu Leu Ile Leu Ser Leu Lys Arg His Thr
210                 215                 220 cta cac atg gga agc aat gcc aca ggg tcc agg gac ccc agc atg aag        720
Leu His Met Gly Ser Asn Ala Thr Gly Ser Arg Asp Pro Ser Met Lys
225                 230                 235                 240 gct cac ata ggg gcc atc aaa gcc acc agc tac ttt ctc atc ctc tac        768
Ala His Ile Gly Ala Ile Lys Ala Thr Ser Tyr Phe Leu Ile Leu Tyr
                245                 250                 255 att ttc aat gca att gct cta ttt ctt tcc acg tcc aac atc ttt gac        816
Ile Phe Asn Ala Ile Ala Leu Phe Leu Ser Thr Ser Asn Ile Phe Asp
            260                 265                 270 act tac agt tcc tgg aat att ttg tgc aag atc atc atg gct gcc tac        864
Thr Tyr Ser Ser Trp Asn Ile Leu Cys Lys Ile Ile Met Ala Ala Tyr
        275                 280                 285 cct gcc ggc cac tca gta caa ctg atc ttg ggc aac cct ggg ctg aga        912
Pro Ala Gly His Ser Val Gln Leu Ile Leu Gly Asn Pro Gly Leu Arg
290                 295                 300 aga gcc tgg aag cgg ttt cag cac caa gtt cct ctt tac cta aaa ggg        960
Arg Ala Trp Lys Arg Phe Gln His Gln Val Pro Leu Tyr Leu Lys Gly
305                 310                 315                 320
```

```
cag act ctg tga                                                    972
Gln Thr Leu
```

<210> SEQ ID NO 10
<211> LENGTH: 323
<212> TYPE: PRT
<213> ORGANISM: Homo sapiens

<400> SEQUENCE: 10

```
Met Ala Thr Val Asn Thr Asp Ala Thr Asp Lys Asp Ile Ser Lys Phe
1               5                   10                  15

Lys Val Thr Phe Thr Leu Val Val Ser Gly Ile Glu Cys Ile Thr Gly
            20                  25                  30

Ile Leu Gly Ser Gly Phe Ile Thr Ala Ile Tyr Gly Ala Glu Trp Ala
        35                  40                  45

Arg Gly Lys Thr Leu Pro Thr Gly Asp Arg Ile Met Leu Met Leu Ser
    50                  55                  60

Phe Ser Arg Leu Leu Leu Gln Ile Trp Met Met Leu Glu Asn Ile Phe
65                  70                  75                  80

Ser Leu Leu Phe Arg Ile Val Tyr Asn Gln Asn Ser Val Tyr Ile Leu
                85                  90                  95

Phe Lys Val Ile Thr Val Phe Leu Asn His Ser Asn Leu Trp Phe Ala
            100                 105                 110

Ala Trp Leu Lys Val Phe Tyr Cys Leu Arg Ile Ala Asn Phe Asn His
        115                 120                 125

Pro Leu Phe Phe Leu Met Lys Arg Lys Ile Ile Val Leu Met Pro Trp
    130                 135                 140

Leu Leu Arg Leu Ser Val Leu Val Ser Leu Ser Phe Ser Phe Pro Leu
145                 150                 155                 160

Ser Arg Asp Val Phe Asn Val Tyr Val Asn Ser Ser Ile Pro Ile Pro
                165                 170                 175

Ser Ser Asn Ser Thr Glu Lys Lys Tyr Phe Ser Glu Thr Asn Met Val
            180                 185                 190

Asn Leu Val Phe Phe Tyr Asn Met Gly Ile Phe Val Pro Leu Ile Met
        195                 200                 205

Phe Ile Leu Ala Ala Thr Leu Leu Ile Leu Ser Leu Lys Arg His Thr
    210                 215                 220

Leu His Met Gly Ser Asn Ala Thr Gly Ser Arg Asp Pro Ser Met Lys
225                 230                 235                 240

Ala His Ile Gly Ala Ile Lys Ala Thr Ser Tyr Phe Leu Ile Leu Tyr
                245                 250                 255

Ile Phe Asn Ala Ile Ala Leu Phe Leu Ser Thr Ser Asn Ile Phe Asp
            260                 265                 270

Thr Tyr Ser Ser Trp Asn Ile Leu Cys Lys Ile Ile Met Ala Ala Tyr
        275                 280                 285

Pro Ala Gly His Ser Val Gln Leu Ile Leu Gly Asn Pro Gly Leu Arg
    290                 295                 300

Arg Ala Trp Lys Arg Phe Gln His Gln Val Pro Leu Tyr Leu Lys Gly
305                 310                 315                 320

Gln Thr Leu
```

<210> SEQ ID NO 11
<211> LENGTH: 1017
<212> TYPE: DNA
<213> ORGANISM: Homo sapiens
<220> FEATURE:
<221> NAME/KEY: CDS

<222> LOCATION: (1)..(1017)

<400> SEQUENCE: 11

```
atg cta ggg aga tgt ttt cct cca gac acc aaa gag aag caa cag ctc      48
Met Leu Gly Arg Cys Phe Pro Pro Asp Thr Lys Glu Lys Gln Gln Leu
1               5                   10                  15 aga atg act aaa ctc tgc gat cct gca gaa agt gaa ttg tcg cca ttt      96
Arg Met Thr Lys Leu Cys Asp Pro Ala Glu Ser Glu Leu Ser Pro Phe
            20                  25                  30 ctc atc acc tta att tta gca gtt tta ctt gct gaa tac ctc att ggt     144
Leu Ile Thr Leu Ile Leu Ala Val Leu Leu Ala Glu Tyr Leu Ile Gly
        35                  40                  45 atc att gca aat ggt ttc atc atg gct ata cat gca gct gaa tgg gtt     192
Ile Ile Ala Asn Gly Phe Ile Met Ala Ile His Ala Ala Glu Trp Val
    50                  55                  60 caa aat aag gca gtt tcc aca agt ggc agg atc ctg gtt ttc ctg agt     240
Gln Asn Lys Ala Val Ser Thr Ser Gly Arg Ile Leu Val Phe Leu Ser
65                  70                  75                  80 gta tcc aga ata gct ctc caa agc ctc atg atg tta gaa att acc atc     288
Val Ser Arg Ile Ala Leu Gln Ser Leu Met Met Leu Glu Ile Thr Ile
                85                  90                  95 agc tca acc tcc cta agt ttt tat tct gaa gac gct gta tat tat gca     336
Ser Ser Thr Ser Leu Ser Phe Tyr Ser Glu Asp Ala Val Tyr Tyr Ala
            100                 105                 110 ttc aaa ata agt ttt ata ttc tta aat ttt tgt agc ctg tgg ttt gct     384
Phe Lys Ile Ser Phe Ile Phe Leu Asn Phe Cys Ser Leu Trp Phe Ala
        115                 120                 125 gcc tgg ctc agt ttc ttc tac ttt gtg aag att gcc aat ttc tcc tac     432
Ala Trp Leu Ser Phe Phe Tyr Phe Val Lys Ile Ala Asn Phe Ser Tyr
    130                 135                 140 ccc ctt ttc ctc aaa ctg agg tgg aga att act gga ttg ata ccc tgg     480
Pro Leu Phe Leu Lys Leu Arg Trp Arg Ile Thr Gly Leu Ile Pro Trp
145                 150                 155                 160 ctt ctg tgg ctg tcc gtg ttt att tcc ttc agt cac agc atg ttc tgc     528
Leu Leu Trp Leu Ser Val Phe Ile Ser Phe Ser His Ser Met Phe Cys
                165                 170                 175 atc aac atc tgc act gtg tat tgt aac aat tct ttc cct atc cac tcc     576
Ile Asn Ile Cys Thr Val Tyr Cys Asn Asn Ser Phe Pro Ile His Ser
            180                 185                 190 tcc aac tcc act aag aaa aca tac ttg tct gag atc aat gtg gtc ggt     624
Ser Asn Ser Thr Lys Lys Thr Tyr Leu Ser Glu Ile Asn Val Val Gly
        195                 200                 205 ctg gct ttt ttc ttt aac ctg ggg att gtg act cct ctg atc atg ttc     672
Leu Ala Phe Phe Phe Asn Leu Gly Ile Val Thr Pro Leu Ile Met Phe
    210                 215                 220 atc ctg aca gcc acc ctg ctg atc ctc tct ctc aag aga cac acc cta     720
Ile Leu Thr Ala Thr Leu Leu Ile Leu Ser Leu Lys Arg His Thr Leu
225                 230                 235                 240 cac atg gga agc aat gcc aca ggg tcc aac gac ccc agc atg gag gct     768
His Met Gly Ser Asn Ala Thr Gly Ser Asn Asp Pro Ser Met Glu Ala
                245                 250                 255 cac atg ggg gcc atc aaa gct atc agc tac ttt ctc att ctc tac att     816
His Met Gly Ala Ile Lys Ala Ile Ser Tyr Phe Leu Ile Leu Tyr Ile
            260                 265                 270 ttc aat gca gtt gct ctg ttt atc tac ctg tcc aac atg ttt gac atc     864
Phe Asn Ala Val Ala Leu Phe Ile Tyr Leu Ser Asn Met Phe Asp Ile
        275                 280                 285 aac agt ctg tgg aat aat ttg tgc cag atc atc atg gct gcc tac cct     912
Asn Ser Leu Trp Asn Asn Leu Cys Gln Ile Ile Met Ala Ala Tyr Pro
    290                 295                 300
```

-continued

```
gcc agc cac tca att cta ctg att caa gat aac cct ggg ctg aga aga    960
Ala Ser His Ser Ile Leu Leu Ile Gln Asp Asn Pro Gly Leu Arg Arg
305                 310                 315                 320 gcc tgg aag cgg ctt cag ctt cga ctt cat ctt tac cca aaa gag tgg   1008
Ala Trp Lys Arg Leu Gln Leu Arg Leu His Leu Tyr Pro Lys Glu Trp
            325                 330                 335 act ctg tga                                                        1017
Thr Leu

<210> SEQ ID NO 12
<211> LENGTH: 338
<212> TYPE: PRT
<213> ORGANISM: Homo sapiens

<400> SEQUENCE: 12

Met Leu Gly Arg Cys Phe Pro Pro Asp Thr Lys Glu Lys Gln Gln Leu
1               5                   10                  15

Arg Met Thr Lys Leu Cys Asp Pro Ala Glu Ser Glu Leu Ser Pro Phe
            20                  25                  30

Leu Ile Thr Leu Ile Leu Ala Val Leu Leu Ala Glu Tyr Leu Ile Gly
        35                  40                  45

Ile Ile Ala Asn Gly Phe Ile Met Ala Ile His Ala Ala Glu Trp Val
    50                  55                  60

Gln Asn Lys Ala Val Ser Thr Ser Gly Arg Ile Leu Val Phe Leu Ser
65                  70                  75                  80

Val Ser Arg Ile Ala Leu Gln Ser Leu Met Met Leu Glu Ile Thr Ile
                85                  90                  95

Ser Ser Thr Ser Leu Ser Phe Tyr Ser Glu Asp Ala Val Tyr Tyr Ala
            100                 105                 110

Phe Lys Ile Ser Phe Ile Phe Leu Asn Phe Cys Ser Leu Trp Phe Ala
        115                 120                 125

Ala Trp Leu Ser Phe Phe Tyr Phe Val Lys Ile Ala Asn Phe Ser Tyr
    130                 135                 140

Pro Leu Phe Leu Lys Leu Arg Trp Arg Ile Thr Gly Leu Ile Pro Trp
145                 150                 155                 160

Leu Leu Trp Leu Ser Val Phe Ile Ser Phe Ser His Ser Met Phe Cys
                165                 170                 175

Ile Asn Ile Cys Thr Val Tyr Cys Asn Asn Ser Phe Pro Ile His Ser
            180                 185                 190

Ser Asn Ser Thr Lys Lys Thr Tyr Leu Ser Glu Ile Asn Val Val Gly
        195                 200                 205

Leu Ala Phe Phe Phe Asn Leu Gly Ile Val Thr Pro Leu Ile Met Phe
    210                 215                 220

Ile Leu Thr Ala Thr Leu Leu Ile Leu Ser Leu Lys Arg His Thr Leu
225                 230                 235                 240

His Met Gly Ser Asn Ala Thr Gly Ser Asn Asp Pro Ser Met Glu Ala
                245                 250                 255

His Met Gly Ala Ile Lys Ala Ile Ser Tyr Phe Leu Ile Leu Tyr Ile
            260                 265                 270

Phe Asn Ala Val Ala Leu Phe Ile Tyr Leu Ser Asn Met Phe Asp Ile
        275                 280                 285

Asn Ser Leu Trp Asn Asn Leu Cys Gln Ile Ile Met Ala Ala Tyr Pro
    290                 295                 300

Ala Ser His Ser Ile Leu Leu Ile Gln Asp Asn Pro Gly Leu Arg Arg
305                 310                 315                 320

Ala Trp Lys Arg Leu Gln Leu Arg Leu His Leu Tyr Pro Lys Glu Trp
```

```
                    325                 330                 335

Thr Leu

<210> SEQ ID NO 13
<211> LENGTH: 1017
<212> TYPE: DNA
<213> ORGANISM: Homo sapiens
<220> FEATURE:
<221> NAME/KEY: CDS
<222> LOCATION: (1)..(1017)

<400> SEQUENCE: 13 atg cta ggg aga tgt ttt cct cca gac acc aaa gag aag caa cag ctc        48
Met Leu Gly Arg Cys Phe Pro Pro Asp Thr Lys Glu Lys Gln Gln Leu
1               5                   10                  15 aga atg act aaa ctc tgc gat cct gca gaa agt gaa ttg tcg cca ttt        96
Arg Met Thr Lys Leu Cys Asp Pro Ala Glu Ser Glu Leu Ser Pro Phe
            20                  25                  30 ctc atc acc tta att tta gca gtt tta ctt gct gaa tac ctc att ggt       144
Leu Ile Thr Leu Ile Leu Ala Val Leu Leu Ala Glu Tyr Leu Ile Gly
        35                  40                  45 atc att gca aat ggt ttc atc atg gct ata cat gca gct gaa tgg gtt       192
Ile Ile Ala Asn Gly Phe Ile Met Ala Ile His Ala Ala Glu Trp Val
    50                  55                  60 caa aat aag gca gtt tcc aca agt ggc agg atc ctg gtt ttc ctg agt       240
Gln Asn Lys Ala Val Ser Thr Ser Gly Arg Ile Leu Val Phe Leu Ser
65                  70                  75                  80 gta tcc aga ata gct ctc caa agc ctc atg atg tta gaa att acc atc       288
Val Ser Arg Ile Ala Leu Gln Ser Leu Met Met Leu Glu Ile Thr Ile
                85                  90                  95 agc tca acc tcc cta agt ttt tat tct gaa gac gct gta tat tat gca       336
Ser Ser Thr Ser Leu Ser Phe Tyr Ser Glu Asp Ala Val Tyr Tyr Ala
            100                 105                 110 ttc aaa ata agt ttt ata ttc tta aat ttt tgt agc ctg tgg ttt gct       384
Phe Lys Ile Ser Phe Ile Phe Leu Asn Phe Cys Ser Leu Trp Phe Ala
        115                 120                 125 gcc tgg ctc agt ttc ttc tac ttt gtg aag att gcc aat ttc tcc tac       432
Ala Trp Leu Ser Phe Phe Tyr Phe Val Lys Ile Ala Asn Phe Ser Tyr
    130                 135                 140 ccc ctt ttc ctc aaa ctg agg tgg aga att act gga ttg ata ccc tgg       480
Pro Leu Phe Leu Lys Leu Arg Trp Arg Ile Thr Gly Leu Ile Pro Trp
145                 150                 155                 160 ctt ctg tgg ctg tcc gtg ttt att tcc ttc agt cac agc atg ttc tgc       528
Leu Leu Trp Leu Ser Val Phe Ile Ser Phe Ser His Ser Met Phe Cys
                165                 170                 175 atc aac atc tgc act gtg tat tgt aac aat tct ttc cct atc cac tcc       576
Ile Asn Ile Cys Thr Val Tyr Cys Asn Asn Ser Phe Pro Ile His Ser
            180                 185                 190 tcc aac tcc act aag aaa aca tac ttg tct gag atc aat gtg gtc ggt       624
Ser Asn Ser Thr Lys Lys Thr Tyr Leu Ser Glu Ile Asn Val Val Gly
        195                 200                 205 ctg gct ttt ttc ttt aac ctg ggg att gtg act cct ctg atc atg ttc       672
Leu Ala Phe Phe Phe Asn Leu Gly Ile Val Thr Pro Leu Ile Met Phe
    210                 215                 220 atc ctg aca gcc acc ctg ctg atc ctc tct ctc aag aga cac acc cta       720
Ile Leu Thr Ala Thr Leu Leu Ile Leu Ser Leu Lys Arg His Thr Leu
225                 230                 235                 240 cac atg gga agc aat gcc aca ggg tcc aac gac ccc agc atg gag gct       768
His Met Gly Ser Asn Ala Thr Gly Ser Asn Asp Pro Ser Met Glu Ala
                245                 250                 255 cac atg ggg gcc atc aaa gct atc agc tac ttt ctc att ctc tac att       816
His Met Gly Ala Ile Lys Ala Ile Ser Tyr Phe Leu Ile Leu Tyr Ile
```

```
His Met Gly Ala Ile Lys Ala Ile Ser Tyr Phe Leu Ile Leu Tyr Ile
            260                 265                 270 ttc aat gca gtt gct ctg ttt atc tac ctg tcc aac atg ttt gac atc      864
Phe Asn Ala Val Ala Leu Phe Ile Tyr Leu Ser Asn Met Phe Asp Ile
            275                 280                 285 aac agt ctg tgg aat aat ttg tgc cag atc gtc atg gct gcc tac cct      912
Asn Ser Leu Trp Asn Asn Leu Cys Gln Ile Val Met Ala Ala Tyr Pro
            290                 295                 300 gcc agc cac tca att cta ctg att caa gat aac cct ggg ctg aga aga      960
Ala Ser His Ser Ile Leu Leu Ile Gln Asp Asn Pro Gly Leu Arg Arg
305             310                 315                 320 gcc tgg aag cgg ctt cag ctt cga ctt cat ctt tac cta aaa ggg cag     1008
Ala Trp Lys Arg Leu Gln Leu Arg Leu His Leu Tyr Leu Lys Gly Gln
                325                 330                 335 act ctg tga                                                         1017
Thr Leu <210> SEQ ID NO 14
<211> LENGTH: 338
<212> TYPE: PRT
<213> ORGANISM: Homo sapiens

<400> SEQUENCE: 14

Met Leu Gly Arg Cys Phe Pro Pro Asp Thr Lys Glu Lys Gln Gln Leu
1               5                   10                  15

Arg Met Thr Lys Leu Cys Asp Pro Ala Glu Ser Glu Leu Ser Pro Phe
            20                  25                  30

Leu Ile Thr Leu Ile Leu Ala Val Leu Leu Ala Glu Tyr Leu Ile Gly
        35                  40                  45

Ile Ile Ala Asn Gly Phe Ile Met Ala Ile His Ala Ala Glu Trp Val
    50                  55                  60

Gln Asn Lys Ala Val Ser Thr Ser Gly Arg Ile Leu Val Phe Leu Ser
65                  70                  75                  80

Val Ser Arg Ile Ala Leu Gln Ser Leu Met Met Leu Glu Ile Thr Ile
                85                  90                  95

Ser Ser Thr Ser Leu Ser Phe Tyr Ser Glu Asp Ala Val Tyr Tyr Ala
            100                 105                 110

Phe Lys Ile Ser Phe Ile Phe Leu Asn Phe Cys Ser Leu Trp Phe Ala
        115                 120                 125

Ala Trp Leu Ser Phe Phe Tyr Phe Val Lys Ile Ala Asn Phe Ser Tyr
    130                 135                 140

Pro Leu Phe Leu Lys Leu Arg Trp Arg Ile Thr Gly Leu Ile Pro Trp
145                 150                 155                 160

Leu Leu Trp Leu Ser Val Phe Ile Ser Phe Ser His Ser Met Phe Cys
                165                 170                 175

Ile Asn Ile Cys Thr Val Tyr Cys Asn Asn Ser Phe Pro Ile His Ser
            180                 185                 190

Ser Asn Ser Thr Lys Lys Thr Tyr Leu Ser Glu Ile Asn Val Val Gly
        195                 200                 205

Leu Ala Phe Phe Phe Asn Leu Gly Ile Val Thr Pro Leu Ile Met Phe
    210                 215                 220

Ile Leu Thr Ala Thr Leu Leu Ile Leu Ser Leu Lys Arg His Thr Leu
225                 230                 235                 240

His Met Gly Ser Asn Ala Thr Gly Ser Asn Asp Pro Ser Met Glu Ala
                245                 250                 255

His Met Gly Ala Ile Lys Ala Ile Ser Tyr Phe Leu Ile Leu Tyr Ile
            260                 265                 270
```

-continued

```
Phe Asn Ala Val Ala Leu Phe Ile Tyr Leu Ser Asn Met Phe Asp Ile
            275                 280                 285

Asn Ser Leu Trp Asn Asn Leu Cys Gln Ile Val Met Ala Ala Tyr Pro
        290                 295                 300

Ala Ser His Ser Ile Leu Leu Ile Gln Asp Asn Pro Gly Leu Arg Arg
305                 310                 315                 320

Ala Trp Lys Arg Leu Gln Leu Arg Leu His Leu Tyr Leu Lys Gly Gln
                325                 330                 335

Thr Leu

<210> SEQ ID NO 15
<211> LENGTH: 930
<212> TYPE: DNA
<213> ORGANISM: Homo sapiens
<220> FEATURE:
<221> NAME/KEY: CDS
<222> LOCATION: (1)..(930)

<400> SEQUENCE: 15 atg ata act ttt cta ccc atc att ttt tcc agt ctg gta gtg gtt aca      48
Met Ile Thr Phe Leu Pro Ile Ile Phe Ser Ser Leu Val Val Val Thr
1               5                   10                  15 ttt gtt att gga aat ttt gct aat ggc ttc ata gca ctg gta aat tcc      96
Phe Val Ile Gly Asn Phe Ala Asn Gly Phe Ile Ala Leu Val Asn Ser
                20                  25                  30 att gag tgg ttc aag aga caa aag atc tcc ttt gct gac caa att ctc     144
Ile Glu Trp Phe Lys Arg Gln Lys Ile Ser Phe Ala Asp Gln Ile Leu
            35                  40                  45 act gct ctg gcg gtc tcc aga gtt ggt ttg ctc tgg gta tta tta tta     192
Thr Ala Leu Ala Val Ser Arg Val Gly Leu Leu Trp Val Leu Leu Leu
        50                  55                  60 aac tgg tat tca act gtg ttg aat cca gct ttt aat agt gta gaa gta     240
Asn Trp Tyr Ser Thr Val Leu Asn Pro Ala Phe Asn Ser Val Glu Val
65                  70                  75                  80 aga act act gct tat aat atc tgg gca gtg atc aac cat ttc agc aac     288
Arg Thr Thr Ala Tyr Asn Ile Trp Ala Val Ile Asn His Phe Ser Asn
                85                  90                  95 tgg ctt gct act acc ctc agc ata ttt tat ttg ctc aag att gcc aat     336
Trp Leu Ala Thr Thr Leu Ser Ile Phe Tyr Leu Leu Lys Ile Ala Asn
            100                 105                 110 ttc tcc aac ttt att ttt ctt cac tta aag agg aga gtt aag agt gtc     384
Phe Ser Asn Phe Ile Phe Leu His Leu Lys Arg Arg Val Lys Ser Val
        115                 120                 125 att ctg gtg atg ttg ttg ggg cct ttg cta ttt ttg gct tgt cat ctt     432
Ile Leu Val Met Leu Leu Gly Pro Leu Leu Phe Leu Ala Cys His Leu
130                 135                 140 ttt gtg ata aac atg aat gag att gtg cgg aca aaa gaa ttt gaa gga     480
Phe Val Ile Asn Met Asn Glu Ile Val Arg Thr Lys Glu Phe Glu Gly
145                 150                 155                 160 aac atg act tgg aag atc aaa ttg aag agt gca atg tac ttt tca aat     528
Asn Met Thr Trp Lys Ile Lys Leu Lys Ser Ala Met Tyr Phe Ser Asn
                165                 170                 175 atg act gta acc atg gta gca aac tta gta ccc ttc act ctg acc cta     576
Met Thr Val Thr Met Val Ala Asn Leu Val Pro Phe Thr Leu Thr Leu
            180                 185                 190 cta tct ttt atg ctg tta atc tgt tct ttg tgt aaa cat ctc aag aag     624
Leu Ser Phe Met Leu Leu Ile Cys Ser Leu Cys Lys His Leu Lys Lys
        195                 200                 205 atg cag ctc cat ggt aaa gga tct caa gat ccc agc acc aag gtc cac     672
Met Gln Leu His Gly Lys Gly Ser Gln Asp Pro Ser Thr Lys Val His
```

```
                        210                 215                 220
ata aaa gct ttg caa act gtg atc tcc ttc ctc ttg tta tgt gcc att        720
Ile Lys Ala Leu Gln Thr Val Ile Ser Phe Leu Leu Leu Cys Ala Ile
225                 230                 235                 240 tac ttt ctg tcc ata atg ata tca gtt tgg agt ttt gga agt ctg gaa        768
Tyr Phe Leu Ser Ile Met Ile Ser Val Trp Ser Phe Gly Ser Leu Glu
                        245                 250                 255 aac aaa cct gtc ttc atg ttc tgc aaa gct att aga ttc agc tat cct        816
Asn Lys Pro Val Phe Met Phe Cys Lys Ala Ile Arg Phe Ser Tyr Pro
                260                 265                 270 tca atc cac cca ttc atc ctg att tgg gga aac aag aag cta aag cag        864
Ser Ile His Pro Phe Ile Leu Ile Trp Gly Asn Lys Lys Leu Lys Gln
            275                 280                 285 act ttt ctt tca gtt ttt tgg caa atg agg tac tgg gtg aaa gga gag        912
Thr Phe Leu Ser Val Phe Trp Gln Met Arg Tyr Trp Val Lys Gly Glu
        290                 295                 300 aag act tca tct cca tag                                                930
Lys Thr Ser Ser Pro
305

<210> SEQ ID NO 16
<211> LENGTH: 309
<212> TYPE: PRT
<213> ORGANISM: Homo sapiens

<400> SEQUENCE: 16

Met Ile Thr Phe Leu Pro Ile Ile Phe Ser Ser Leu Val Val Thr
1               5                   10                  15

Phe Val Ile Gly Asn Phe Ala Asn Gly Phe Ile Ala Leu Val Asn Ser
                20                  25                  30

Ile Glu Trp Phe Lys Arg Gln Lys Ile Ser Phe Ala Asp Gln Ile Leu
            35                  40                  45

Thr Ala Leu Ala Val Ser Arg Val Gly Leu Leu Trp Val Leu Leu Leu
        50                  55                  60

Asn Trp Tyr Ser Thr Val Leu Asn Pro Ala Phe Asn Ser Val Glu Val
65                  70                  75                  80

Arg Thr Thr Ala Tyr Asn Ile Trp Ala Val Ile Asn His Phe Ser Asn
                85                  90                  95

Trp Leu Ala Thr Thr Leu Ser Ile Phe Tyr Leu Leu Lys Ile Ala Asn
            100                 105                 110

Phe Ser Asn Phe Ile Phe Leu His Leu Lys Arg Arg Val Lys Ser Val
        115                 120                 125

Ile Leu Val Met Leu Leu Gly Pro Leu Leu Phe Leu Ala Cys His Leu
    130                 135                 140

Phe Val Ile Asn Met Asn Glu Ile Val Arg Thr Lys Glu Phe Glu Gly
145                 150                 155                 160

Asn Met Thr Trp Lys Ile Lys Leu Lys Ser Ala Met Tyr Phe Ser Asn
                165                 170                 175

Met Thr Val Thr Met Val Ala Asn Leu Val Pro Phe Thr Leu Thr Leu
            180                 185                 190

Leu Ser Phe Met Leu Leu Ile Cys Ser Leu Cys Lys His Leu Lys Lys
        195                 200                 205

Met Gln Leu His Gly Lys Gly Ser Gln Asp Pro Ser Thr Lys Val His
    210                 215                 220

Ile Lys Ala Leu Gln Thr Val Ile Ser Phe Leu Leu Leu Cys Ala Ile
225                 230                 235                 240

Tyr Phe Leu Ser Ile Met Ile Ser Val Trp Ser Phe Gly Ser Leu Glu
```

| | | | | | | 245 | | | | | 250 | | | | | 255 | | | |
|---|---|---|---|---|---|---|---|---|---|---|---|---|---|---|---|---|---|---|---|
Asn Lys Pro Val Phe Met Phe Cys Lys Ala Ile Arg Phe Ser Tyr Pro
            260                265            270

Ser Ile His Pro Phe Ile Leu Ile Trp Gly Asn Lys Lys Leu Lys Gln
      275              280              285

Thr Phe Leu Ser Val Phe Trp Gln Met Arg Tyr Trp Val Lys Gly Glu
  290              295              300

Lys Thr Ser Ser Pro
305

<210> SEQ ID NO 17
<211> LENGTH: 957
<212> TYPE: DNA
<213> ORGANISM: Homo sapiens
<220> FEATURE:
<221> NAME/KEY: CDS
<222> LOCATION: (1)..(957)

<400> SEQUENCE: 17

```
atg tta aag gac tca gaa caa gtg tta cta agc ctg cat ttt ttt atc        48
Met Leu Lys Asp Ser Glu Gln Val Leu Leu Ser Leu His Phe Phe Ile
1               5                   10                  15 tgt tca aac atg atg tgt ttt ctg ctc atc att tca tca att ctg gta        96
Cys Ser Asn Met Met Cys Phe Leu Leu Ile Ile Ser Ser Ile Leu Val
            20                  25                  30 gtg ttt gca ttt gtt ctt gga aat gtt gcc aat ggc ttc ata gcc cta       144
Val Phe Ala Phe Val Leu Gly Asn Val Ala Asn Gly Phe Ile Ala Leu
        35                  40                  45 gta aat gtc att gac tgg gtt aac aca cga aag atc tcc tca gct gag       192
Val Asn Val Ile Asp Trp Val Asn Thr Arg Lys Ile Ser Ser Ala Glu
    50                  55                  60 caa att ctc act gct ctg gtg gtc tcc aga att ggt tta ctc tgg gtc       240
Gln Ile Leu Thr Ala Leu Val Val Ser Arg Ile Gly Leu Leu Trp Val
65                  70                  75                  80 atg tta ttc ctt tgg tat gca act gtg ttt aat tct gct tta tat ggt       288
Met Leu Phe Leu Trp Tyr Ala Thr Val Phe Asn Ser Ala Leu Tyr Gly
                85                  90                  95 tta gaa gta aga att gtt gct tct aat gcc tgg gct gta acg aac cat       336
Leu Glu Val Arg Ile Val Ala Ser Asn Ala Trp Ala Val Thr Asn His
            100                 105                 110 ttc agc atg tgg ctt gct gct agc ctc agc ata ttt tgt ttg ctc aag       384
Phe Ser Met Trp Leu Ala Ala Ser Leu Ser Ile Phe Cys Leu Leu Lys
        115                 120                 125 att gcc aat ttc tcc aac ctt att tct ctc cac cta aag aag aga att       432
Ile Ala Asn Phe Ser Asn Leu Ile Ser Leu His Leu Lys Lys Arg Ile
    130                 135                 140 aag agt gtt gtt ctg gtg ata ctg ttg ggg ccc ttg gta ttt ctg att       480
Lys Ser Val Val Leu Val Ile Leu Leu Gly Pro Leu Val Phe Leu Ile
145                 150                 155                 160 tgt aat ctt gct gtg ata acc atg gat gag aga gtg tgg aca aaa gaa       528
Cys Asn Leu Ala Val Ile Thr Met Asp Glu Arg Val Trp Thr Lys Glu
                165                 170                 175 tat gaa gga aat gtg act tgg aag atc aaa ttg agg aat gca ata cac       576
Tyr Glu Gly Asn Val Thr Trp Lys Ile Lys Leu Arg Asn Ala Ile His
            180                 185                 190 ctt tca agc ttg act gta act act cta gca aac ctc ata ccc ttt act       624
Leu Ser Ser Leu Thr Val Thr Thr Leu Ala Asn Leu Ile Pro Phe Thr
        195                 200                 205 ctg agc cta ata tgt ttt ctg ctg tta atc tgt tct ctt tgt aaa cat       672
Leu Ser Leu Ile Cys Phe Leu Leu Leu Ile Cys Ser Leu Cys Lys His
    210                 215                 220
```

```
ctc aag aag atg cgg ctc cat agc aaa gga tct caa gat ccc agc acc       720
Leu Lys Lys Met Arg Leu His Ser Lys Gly Ser Gln Asp Pro Ser Thr
225                 230                 235                 240 aag gtc cat ata aaa gct ttg caa act gtg acc tcc ttc ctc atg tta       768
Lys Val His Ile Lys Ala Leu Gln Thr Val Thr Ser Phe Leu Met Leu
            245                 250                 255 ttt gcc att tac ttt ctg tgt ata atc aca tca act tgg aat ctt agg       816
Phe Ala Ile Tyr Phe Leu Cys Ile Ile Thr Ser Thr Trp Asn Leu Arg
        260                 265                 270 aca cag cag agc aaa ctt gta ctc ctg ctt tgc caa act gtt gca atc       864
Thr Gln Gln Ser Lys Leu Val Leu Leu Leu Cys Gln Thr Val Ala Ile
    275                 280                 285 atg tat cct tca ttc cac tca ttc atc ctg att atg gga agt agg aag       912
Met Tyr Pro Ser Phe His Ser Phe Ile Leu Ile Met Gly Ser Arg Lys
290                 295                 300 cta aaa cag acc ttt ctt tca gtt ttg tgg cag atg aca cgc tga           957
Leu Lys Gln Thr Phe Leu Ser Val Leu Trp Gln Met Thr Arg
305                 310                 315

<210> SEQ ID NO 18
<211> LENGTH: 318
<212> TYPE: PRT
<213> ORGANISM: Homo sapiens

<400> SEQUENCE: 18

Met Leu Lys Asp Ser Glu Gln Val Leu Leu Ser Leu His Phe Phe Ile
1               5                   10                  15

Cys Ser Asn Met Met Cys Phe Leu Leu Ile Ile Ser Ser Ile Leu Val
            20                  25                  30

Val Phe Ala Phe Val Leu Gly Asn Val Ala Asn Gly Phe Ile Ala Leu
        35                  40                  45

Val Asn Val Ile Asp Trp Val Asn Thr Arg Lys Ile Ser Ser Ala Glu
    50                  55                  60

Gln Ile Leu Thr Ala Leu Val Val Ser Arg Ile Gly Leu Leu Trp Val
65                  70                  75                  80

Met Leu Phe Leu Trp Tyr Ala Thr Val Phe Asn Ser Ala Leu Tyr Gly
                85                  90                  95

Leu Glu Val Arg Ile Val Ala Ser Asn Ala Trp Ala Val Thr Asn His
            100                 105                 110

Phe Ser Met Trp Leu Ala Ala Ser Leu Ser Ile Phe Cys Leu Leu Lys
        115                 120                 125

Ile Ala Asn Phe Ser Asn Leu Ile Ser Leu His Leu Lys Lys Arg Ile
    130                 135                 140

Lys Ser Val Val Leu Val Ile Leu Leu Gly Pro Leu Val Phe Leu Ile
145                 150                 155                 160

Cys Asn Leu Ala Val Ile Thr Met Asp Glu Arg Val Trp Thr Lys Glu
                165                 170                 175

Tyr Glu Gly Asn Val Thr Trp Lys Ile Lys Leu Arg Asn Ala Ile His
            180                 185                 190

Leu Ser Ser Leu Thr Val Thr Thr Leu Ala Asn Leu Ile Pro Phe Thr
        195                 200                 205

Leu Ser Leu Ile Cys Phe Leu Leu Ile Cys Ser Leu Cys Lys His
    210                 215                 220

Leu Lys Lys Met Arg Leu His Ser Lys Gly Ser Gln Asp Pro Ser Thr
225                 230                 235                 240

Lys Val His Ile Lys Ala Leu Gln Thr Val Thr Ser Phe Leu Met Leu
                245                 250                 255
```

```
Phe Ala Ile Tyr Phe Leu Cys Ile Ile Thr Ser Thr Trp Asn Leu Arg
            260                 265                 270

Thr Gln Gln Ser Lys Leu Val Leu Leu Cys Gln Thr Val Ala Ile
        275                 280                 285

Met Tyr Pro Ser Phe His Ser Phe Ile Leu Ile Met Gly Ser Arg Lys
290                 295                 300

Leu Lys Gln Thr Phe Leu Ser Val Leu Trp Gln Met Thr Arg
305                 310                 315

<210> SEQ ID NO 19
<211> LENGTH: 930
<212> TYPE: DNA
<213> ORGANISM: Homo sapiens
<220> FEATURE:
<221> NAME/KEY: CDS
<222> LOCATION: (1)..(930)

<400> SEQUENCE: 19 atg atg agt ttt cta cac att gtt ttt tcc att cta gta gtg gtt gca      48
Met Met Ser Phe Leu His Ile Val Phe Ser Ile Leu Val Val Val Ala
1               5                   10                  15 ttt att ctt gga aat ttt gcc aat ggc ttt ata gca ctg ata aat ttc      96
Phe Ile Leu Gly Asn Phe Ala Asn Gly Phe Ile Ala Leu Ile Asn Phe
            20                  25                  30 att gcc tgg gtc aag aga caa aag atc tcc tca gct gat caa att att     144
Ile Ala Trp Val Lys Arg Gln Lys Ile Ser Ser Ala Asp Gln Ile Ile
        35                  40                  45 gct gct ctg gca gtc tcc aga gtt ggt ttg ctc tgg gta ata tta tta     192
Ala Ala Leu Ala Val Ser Arg Val Gly Leu Leu Trp Val Ile Leu Leu
    50                  55                  60 cat tgg tat tca act gtg ttg aat cca act tca tct aat tta aaa gta     240
His Trp Tyr Ser Thr Val Leu Asn Pro Thr Ser Ser Asn Leu Lys Val
65                  70                  75                  80 ata att ttt att tct aat gcc tgg gca gta acc aat cat ttc agc atc     288
Ile Ile Phe Ile Ser Asn Ala Trp Ala Val Thr Asn His Phe Ser Ile
                85                  90                  95 tgg ctt gct act agc ctc agc ata ttt tat ttg ctc aag atc gtc aat     336
Trp Leu Ala Thr Ser Leu Ser Ile Phe Tyr Leu Leu Lys Ile Val Asn
            100                 105                 110 ttc tcc aga ctt att ttt cat cac tta aaa agg aag gct aag agt gta     384
Phe Ser Arg Leu Ile Phe His His Leu Lys Arg Lys Ala Lys Ser Val
        115                 120                 125 gtt ctg gtg ata gtg ttg ggg tct ttg ttc ttt ttg gtt tgt cac ctt     432
Val Leu Val Ile Val Leu Gly Ser Leu Phe Phe Leu Val Cys His Leu
    130                 135                 140 gtg atg aaa cac acg tat ata aat gtg tgg aca gaa gaa tgt gaa gga     480
Val Met Lys His Thr Tyr Ile Asn Val Trp Thr Glu Glu Cys Glu Gly
145                 150                 155                 160 aac gta act tgg aag atc aaa ctg agg aat gca atg cac ctt tcc aac     528
Asn Val Thr Trp Lys Ile Lys Leu Arg Asn Ala Met His Leu Ser Asn
                165                 170                 175 ttg act gta gcc atg cta gca aac ttg ata cca ttc act ctg acc ctg     576
Leu Thr Val Ala Met Leu Ala Asn Leu Ile Pro Phe Thr Leu Thr Leu
            180                 185                 190 ata tct ttt ctg ctg tta atc tac tct ctg tgt aaa cat ctg aag aag     624
Ile Ser Phe Leu Leu Leu Ile Tyr Ser Leu Cys Lys His Leu Lys Lys
        195                 200                 205 atg cag ctc cat ggc aaa gga tct caa gat ccc agc acc aag atc cac     672
Met Gln Leu His Gly Lys Gly Ser Gln Asp Pro Ser Thr Lys Ile His
    210                 215                 220
```

-continued

```
ata aaa gct ctg caa act gtg acc tcc ttc ctc ata tta ctt gcc att    720
Ile Lys Ala Leu Gln Thr Val Thr Ser Phe Leu Ile Leu Leu Ala Ile
225                 230                 235                 240 tac ttt ctg tgt cta atc ata tcg ttt tgg aat ttt aag atg cga cca    768
Tyr Phe Leu Cys Leu Ile Ile Ser Phe Trp Asn Phe Lys Met Arg Pro
                245                 250                 255 aaa gaa att gtc tta atg ctt tgc caa gct ttt gga atc ata tat cca    816
Lys Glu Ile Val Leu Met Leu Cys Gln Ala Phe Gly Ile Ile Tyr Pro
            260                 265                 270 tca ttc cac tca ttc att ctg att tgg ggg aac aag acg cta aag cag    864
Ser Phe His Ser Phe Ile Leu Ile Trp Gly Asn Lys Thr Leu Lys Gln
        275                 280                 285 acc ttt ctt tca gtt ttg tgg cag gtg act tgc tgg gca aaa gga cag    912
Thr Phe Leu Ser Val Leu Trp Gln Val Thr Cys Trp Ala Lys Gly Gln
    290                 295                 300 aac cag tca act cca tag                                            930
Asn Gln Ser Thr Pro
305
```

<210> SEQ ID NO 20
<211> LENGTH: 309
<212> TYPE: PRT
<213> ORGANISM: Homo sapiens

<400> SEQUENCE: 20

```
Met Met Ser Phe Leu His Ile Val Phe Ser Ile Leu Val Val Val Ala
1               5                   10                  15

Phe Ile Leu Gly Asn Phe Ala Asn Gly Phe Ile Ala Leu Ile Asn Phe
                20                  25                  30

Ile Ala Trp Val Lys Arg Gln Lys Ile Ser Ser Ala Asp Gln Ile Ile
            35                  40                  45

Ala Ala Leu Ala Val Ser Arg Val Gly Leu Leu Trp Val Ile Leu Leu
        50                  55                  60

His Trp Tyr Ser Thr Val Leu Asn Pro Thr Ser Ser Asn Leu Lys Val
65                  70                  75                  80

Ile Ile Phe Ile Ser Asn Ala Trp Ala Val Thr Asn His Phe Ser Ile
                85                  90                  95

Trp Leu Ala Thr Ser Leu Ser Ile Phe Tyr Leu Leu Lys Ile Val Asn
            100                 105                 110

Phe Ser Arg Leu Ile Phe His His Leu Lys Arg Lys Ala Lys Ser Val
        115                 120                 125

Val Leu Val Ile Val Leu Gly Ser Leu Phe Phe Leu Val Cys His Leu
    130                 135                 140

Val Met Lys His Thr Tyr Ile Asn Val Trp Thr Glu Glu Cys Glu Gly
145                 150                 155                 160

Asn Val Thr Trp Lys Ile Lys Leu Arg Asn Ala Met His Leu Ser Asn
                165                 170                 175

Leu Thr Val Ala Met Leu Ala Asn Leu Ile Pro Phe Thr Leu Thr Leu
            180                 185                 190

Ile Ser Phe Leu Leu Leu Ile Tyr Ser Leu Cys Lys His Leu Lys Lys
        195                 200                 205

Met Gln Leu His Gly Lys Gly Ser Gln Asp Pro Ser Thr Lys Ile His
    210                 215                 220

Ile Lys Ala Leu Gln Thr Val Thr Ser Phe Leu Ile Leu Leu Ala Ile
225                 230                 235                 240

Tyr Phe Leu Cys Leu Ile Ile Ser Phe Trp Asn Phe Lys Met Arg Pro
                245                 250                 255
```

```
                    Lys Glu Ile Val Leu Met Leu Cys Gln Ala Phe Gly Ile Ile Tyr Pro
                                    260                 265                 270

Ser Phe His Ser Phe Ile Leu Ile Trp Gly Asn Lys Thr Leu Lys Gln
                                275                 280                 285

Thr Phe Leu Ser Val Leu Trp Gln Val Thr Cys Trp Ala Lys Gly Gln
                            290                 295                 300

Asn Gln Ser Thr Pro
                    305

<210> SEQ ID NO 21
<211> LENGTH: 930
<212> TYPE: DNA
<213> ORGANISM: Homo sapiens
<220> FEATURE:
<221> NAME/KEY: CDS
<222> LOCATION: (1)..(930)

<400> SEQUENCE: 21 atg aca act ttt ata ccc atc att ttt tcc agt gtg gta gtg gtt cta       48
Met Thr Thr Phe Ile Pro Ile Ile Phe Ser Ser Val Val Val Val Leu
1               5                   10                  15 ttt gtt att gga aat ttt gct aat ggc ttc ata gca ttg gta aat tcc       96
Phe Val Ile Gly Asn Phe Ala Asn Gly Phe Ile Ala Leu Val Asn Ser
            20                  25                  30 att gag cgg gtc aag aga caa aag atc tct ttt gct gac cag att ctc      144
Ile Glu Arg Val Lys Arg Gln Lys Ile Ser Phe Ala Asp Gln Ile Leu
        35                  40                  45 act gct ctg gcg gtc tcc aga gtt ggt ttg ctc tgg gta tta tta tta      192
Thr Ala Leu Ala Val Ser Arg Val Gly Leu Leu Trp Val Leu Leu Leu
 50                  55                  60 aat tgg tat tca act gtg ttt aat cca gct ttt tat agt gta gaa gta      240
Asn Trp Tyr Ser Thr Val Phe Asn Pro Ala Phe Tyr Ser Val Glu Val
65                  70                  75                  80 aga act act gct tat aat gtc tgg gca gta acc ggc cat ttc agc aac      288
Arg Thr Thr Ala Tyr Asn Val Trp Ala Val Thr Gly His Phe Ser Asn
                85                  90                  95 tgg ctt gct act agc ctc agc ata ttt tat ttg ctc aag att gcc aat      336
Trp Leu Ala Thr Ser Leu Ser Ile Phe Tyr Leu Leu Lys Ile Ala Asn
            100                 105                 110 ttc tcc aac ctt att ttt ctt cac tta aag agg aga gtt aag agt gtc      384
Phe Ser Asn Leu Ile Phe Leu His Leu Lys Arg Arg Val Lys Ser Val
        115                 120                 125 att ctg gtg atg ctg ttg ggg cct tta cta ttt ttg gct tgt caa ctt      432
Ile Leu Val Met Leu Leu Gly Pro Leu Leu Phe Leu Ala Cys Gln Leu
    130                 135                 140 ttt gtg ata aac atg aaa gag att gta cgg aca aaa gaa tat gaa gga      480
Phe Val Ile Asn Met Lys Glu Ile Val Arg Thr Lys Glu Tyr Glu Gly
145                 150                 155                 160 aac ttg act tgg aag atc aaa ttg agg agt gca gtg tac ctt tca gat      528
Asn Leu Thr Trp Lys Ile Lys Leu Arg Ser Ala Val Tyr Leu Ser Asp
                165                 170                 175 gcg act gta acc acg cta gga aac tta gtg ccc ttc act ctg acc ctg      576
Ala Thr Val Thr Thr Leu Gly Asn Leu Val Pro Phe Thr Leu Thr Leu
            180                 185                 190 cta tgt ttt ttg ctg tta atc tgt tct ctg tgt aaa cat ctc aag aag      624
Leu Cys Phe Leu Leu Leu Ile Cys Ser Leu Cys Lys His Leu Lys Lys
        195                 200                 205 atg cag ctc cat ggt aaa gga tct caa gat ccc agc acc aag gtc cac      672
Met Gln Leu His Gly Lys Gly Ser Gln Asp Pro Ser Thr Lys Val His
    210                 215                 220 ata aaa gct ttg caa act gtg atc ttt ttc ctc ttg tta tgt gcc gtt      720
```

```
Ile Lys Ala Leu Gln Thr Val Ile Phe Phe Leu Leu Leu Cys Ala Val
225                 230                 235                 240 tac ttt ctg tcc ata atg ata tca gtt tgg agt ttt ggg agt ctg gaa      768
Tyr Phe Leu Ser Ile Met Ile Ser Val Trp Ser Phe Gly Ser Leu Glu
                245                 250                 255 aac aaa cct gtc ttc atg ttc tgc aaa gct att aga ttc agc tat cct      816
Asn Lys Pro Val Phe Met Phe Cys Lys Ala Ile Arg Phe Ser Tyr Pro
            260                 265                 270 tca atc cac cca ttc atc ctg att tgg gga aac aag aag cta aag cag      864
Ser Ile His Pro Phe Ile Leu Ile Trp Gly Asn Lys Lys Leu Lys Gln
        275                 280                 285 act ttt ctt tca gtt ttg cgg caa gtg agg tac tgg gtg aaa gga gag      912
Thr Phe Leu Ser Val Leu Arg Gln Val Arg Tyr Trp Val Lys Gly Glu
    290                 295                 300 aag cct tca tct cca tag                                              930
Lys Pro Ser Ser Pro
305

<210> SEQ ID NO 22
<211> LENGTH: 309
<212> TYPE: PRT
<213> ORGANISM: Homo sapiens

<400> SEQUENCE: 22

Met Thr Thr Phe Ile Pro Ile Ile Phe Ser Ser Val Val Val Val Leu
1               5                   10                  15

Phe Val Ile Gly Asn Phe Ala Asn Gly Phe Ile Ala Leu Val Asn Ser
            20                  25                  30

Ile Glu Arg Val Lys Arg Gln Lys Ile Ser Phe Ala Asp Gln Ile Leu
        35                  40                  45

Thr Ala Leu Ala Val Ser Arg Val Gly Leu Leu Trp Val Leu Leu Leu
    50                  55                  60

Asn Trp Tyr Ser Thr Val Phe Asn Pro Ala Phe Tyr Ser Val Glu Val
65                  70                  75                  80

Arg Thr Thr Ala Tyr Asn Val Trp Ala Val Thr Gly His Phe Ser Asn
                85                  90                  95

Trp Leu Ala Thr Ser Leu Ser Ile Phe Tyr Leu Leu Lys Ile Ala Asn
            100                 105                 110

Phe Ser Asn Leu Ile Phe Leu His Leu Lys Arg Arg Val Lys Ser Val
        115                 120                 125

Ile Leu Val Met Leu Leu Gly Pro Leu Leu Phe Leu Ala Cys Gln Leu
    130                 135                 140

Phe Val Ile Asn Met Lys Glu Ile Val Arg Thr Lys Glu Tyr Glu Gly
145                 150                 155                 160

Asn Leu Thr Trp Lys Ile Lys Leu Arg Ser Ala Val Tyr Leu Ser Asp
                165                 170                 175

Ala Thr Val Thr Thr Leu Gly Asn Leu Val Pro Phe Thr Leu Thr Leu
            180                 185                 190

Leu Cys Phe Leu Leu Leu Ile Cys Ser Leu Cys Lys His Leu Lys Lys
        195                 200                 205

Met Gln Leu His Gly Lys Gly Ser Gln Asp Pro Ser Thr Lys Val His
    210                 215                 220

Ile Lys Ala Leu Gln Thr Val Ile Phe Leu Leu Leu Cys Ala Val
225                 230                 235                 240

Tyr Phe Leu Ser Ile Met Ile Ser Val Trp Ser Phe Gly Ser Leu Glu
                245                 250                 255

Asn Lys Pro Val Phe Met Phe Cys Lys Ala Ile Arg Phe Ser Tyr Pro
```

```
                260                 265                 270
Ser Ile His Pro Phe Ile Leu Ile Trp Gly Asn Lys Lys Leu Lys Gln
            275                 280                 285

Thr Phe Leu Ser Val Leu Arg Gln Val Arg Tyr Trp Val Lys Gly Glu
            290                 295                 300

Lys Pro Ser Ser Pro
305

<210> SEQ ID NO 23
<211> LENGTH: 900
<212> TYPE: DNA
<213> ORGANISM: Homo sapiens
<220> FEATURE:
<221> NAME/KEY: CDS
<222> LOCATION: (1)..(900)

<400> SEQUENCE: 23 atg cta gag tct cac ctc att atc tat ttt ctt ctt gca gtg ata caa     48
Met Leu Glu Ser His Leu Ile Ile Tyr Phe Leu Leu Ala Val Ile Gln
1               5                   10                  15 ttt ctt ctt ggg att ttc aca aat ggc atc att gtg gtg gtg aat ggc     96
Phe Leu Leu Gly Ile Phe Thr Asn Gly Ile Ile Val Val Val Asn Gly
            20                  25                  30 att gac ttg atc aag cac aga aaa atg gct ccg ctg gat ctc ctt ctt    144
Ile Asp Leu Ile Lys His Arg Lys Met Ala Pro Leu Asp Leu Leu Leu
        35                  40                  45 tct tgt ctg gca gtt tct aga att ttt ctg cag ttg ttc atc ttc tac    192
Ser Cys Leu Ala Val Ser Arg Ile Phe Leu Gln Leu Phe Ile Phe Tyr
    50                  55                  60 gtt aat gtg att gtt atc ttc ttc ata gaa ttc atc atg tgt tct gcg    240
Val Asn Val Ile Val Ile Phe Phe Ile Glu Phe Ile Met Cys Ser Ala
65                  70                  75                  80 aat tgt gca att ctc tta ttt ata aat gaa ttg gaa ctt tgg ctt gcc    288
Asn Cys Ala Ile Leu Leu Phe Ile Asn Glu Leu Glu Leu Trp Leu Ala
                85                  90                  95 aca tgg ctc ggc gtt ttc tat tgt gcc aag gtt gcc agc gtc cgt cac    336
Thr Trp Leu Gly Val Phe Tyr Cys Ala Lys Val Ala Ser Val Arg His
            100                 105                 110 cca ctc ttc atc tgg ttg aag atg agg ata tcc aag ctg gtc cca tgg    384
Pro Leu Phe Ile Trp Leu Lys Met Arg Ile Ser Lys Leu Val Pro Trp
        115                 120                 125 atg atc ctg ggg tct ctg cta tat gta tct atg att tgt gtt ttc cat    432
Met Ile Leu Gly Ser Leu Leu Tyr Val Ser Met Ile Cys Val Phe His
    130                 135                 140 agc aaa tat gca ggg ttt atg gtc cca tac ttc cta agg aaa ttt ttc    480
Ser Lys Tyr Ala Gly Phe Met Val Pro Tyr Phe Leu Arg Lys Phe Phe
145                 150                 155                 160 tcc caa aat gcc aca att caa aaa gaa gat aca ctg gct ata cag att    528
Ser Gln Asn Ala Thr Ile Gln Lys Glu Asp Thr Leu Ala Ile Gln Ile
                165                 170                 175 ttc tct ttt gtt gct gag ttc tca gtg cca ttg ctt atc ttc ctt ttt    576
Phe Ser Phe Val Ala Glu Phe Ser Val Pro Leu Leu Ile Phe Leu Phe
            180                 185                 190 gct gtt ttg ctc ttg att ttc tct ctg ggg agg cac acc cgg caa atg    624
Ala Val Leu Leu Leu Ile Phe Ser Leu Gly Arg His Thr Arg Gln Met
        195                 200                 205 aga aac aca gtg gcc ggc agc agg gtt cct ggc agg ggt gca ccc atc    672
Arg Asn Thr Val Ala Gly Ser Arg Val Pro Gly Arg Gly Ala Pro Ile
    210                 215                 220 agc gcg ttg ctg tct atc ctg tcc ttc ctg atc ctc tac ttc tcc cac    720
Ser Ala Leu Leu Ser Ile Leu Ser Phe Leu Ile Leu Tyr Phe Ser His
```

```
                      225                 230                 235                 240
tgc atg ata aaa gtt ttt ctc tct tct cta aag ttt cac atc aga agg        768
Cys Met Ile Lys Val Phe Leu Ser Ser Leu Lys Phe His Ile Arg Arg
            245                 250                 255 ttc atc ttt ctg ttc ttc atc ctt gtg att ggt ata tac cct tct gga        816
Phe Ile Phe Leu Phe Phe Ile Leu Val Ile Gly Ile Tyr Pro Ser Gly
        260                 265                 270 cac tct ctc atc tta att tta gga aat cct aaa ttg aaa caa aat gca        864
His Ser Leu Ile Leu Ile Leu Gly Asn Pro Lys Leu Lys Gln Asn Ala
    275                 280                 285 aaa aag ttc ctc ctc cac agt aag tgc tgt cag tga                        900
Lys Lys Phe Leu Leu His Ser Lys Cys Cys Gln
290                 295

<210> SEQ ID NO 24
<211> LENGTH: 299
<212> TYPE: PRT
<213> ORGANISM: Homo sapiens

<400> SEQUENCE: 24

Met Leu Glu Ser His Leu Ile Ile Tyr Phe Leu Leu Ala Val Ile Gln
1               5                   10                  15

Phe Leu Leu Gly Ile Phe Thr Asn Gly Ile Ile Val Val Asn Gly
            20                  25                  30

Ile Asp Leu Ile Lys His Arg Lys Met Ala Pro Leu Asp Leu Leu
        35                  40                  45

Ser Cys Leu Ala Val Ser Arg Ile Phe Leu Gln Leu Phe Ile Phe Tyr
    50                  55                  60

Val Asn Val Ile Val Ile Phe Phe Ile Glu Phe Ile Met Cys Ser Ala
65                  70                  75                  80

Asn Cys Ala Ile Leu Leu Phe Ile Asn Glu Leu Gly Leu Trp Leu Ala
                85                  90                  95

Thr Trp Leu Gly Val Phe Tyr Cys Ala Lys Val Ala Ser Val Arg His
            100                 105                 110

Pro Leu Phe Ile Trp Leu Lys Met Arg Ile Ser Lys Leu Val Pro Trp
        115                 120                 125

Met Ile Leu Gly Ser Leu Leu Tyr Val Ser Met Ile Cys Val Phe His
    130                 135                 140

Ser Lys Tyr Ala Gly Phe Met Val Pro Tyr Phe Leu Arg Lys Phe
145                 150                 155                 160

Ser Gln Asn Ala Thr Ile Gln Lys Glu Asp Thr Leu Ala Ile Gln Ile
                165                 170                 175

Phe Ser Phe Val Ala Glu Phe Ser Val Pro Leu Leu Ile Phe Leu Phe
            180                 185                 190

Ala Val Leu Leu Leu Ile Phe Ser Leu Gly Arg His Thr Arg Gln Met
        195                 200                 205

Arg Asn Thr Val Ala Gly Ser Arg Val Pro Gly Arg Gly Ala Pro Ile
    210                 215                 220

Ser Ala Leu Leu Ser Ile Leu Ser Phe Leu Ile Leu Tyr Phe Ser His
225                 230                 235                 240

Cys Met Ile Lys Val Phe Leu Ser Ser Leu Lys Phe His Ile Arg Arg
                245                 250                 255

Phe Ile Phe Leu Phe Phe Ile Leu Val Ile Gly Ile Tyr Pro Ser Gly
            260                 265                 270

His Ser Leu Ile Leu Ile Leu Gly Asn Pro Lys Leu Lys Gln Asn Ala
        275                 280                 285
```

```
               Lys Lys Phe Leu Leu His Ser Lys Cys Cys Gln
                         290                 295

<210> SEQ ID NO 25
<211> LENGTH: 951
<212> TYPE: DNA
<213> ORGANISM: Homo sapiens
<220> FEATURE:
<221> NAME/KEY: CDS
<222> LOCATION: (1)..(951)

<400> SEQUENCE: 25 atg atg gga ctc acc gag ggg gtg ttc ctg att ctg tct ggc act cag       48
Met Met Gly Leu Thr Glu Gly Val Phe Leu Ile Leu Ser Gly Thr Gln
 1               5                  10                  15 ttc aca ctg gga att ctg gtc aat tgt ttc att gag ttg gtc aat ggt       96
Phe Thr Leu Gly Ile Leu Val Asn Cys Phe Ile Glu Leu Val Asn Gly
                20                  25                  30 agc agc tgg ttc aag acc aag aga atg tct ttg tct gac ttc atc atc      144
Ser Ser Trp Phe Lys Thr Lys Arg Met Ser Leu Ser Asp Phe Ile Ile
            35                  40                  45 acc acc ctg gca ctc ttg agg atc att ctg ctg tgt att atc ttg act      192
Thr Thr Leu Ala Leu Leu Arg Ile Ile Leu Leu Cys Ile Ile Leu Thr
        50                  55                  60 gat agt ttt tta ata gaa ttc tct ccc aac aca cat gat tca ggg ata      240
Asp Ser Phe Leu Ile Glu Phe Ser Pro Asn Thr His Asp Ser Gly Ile
 65                  70                  75                  80 ata atg caa att att gat gtt tcc tgg aca ttt aca aac cat ctg agc      288
Ile Met Gln Ile Ile Asp Val Ser Trp Thr Phe Thr Asn His Leu Ser
                85                  90                  95 att tgg ctt gcc acc tgt ctt ggt gtc ctc tac tgc ctg aaa atc gcc      336
Ile Trp Leu Ala Thr Cys Leu Gly Val Leu Tyr Cys Leu Lys Ile Ala
            100                 105                 110 agt ttc tct cac ccc aca ttc ctc tgg ctc aag tgg aga gtt tct agg      384
Ser Phe Ser His Pro Thr Phe Leu Trp Leu Lys Trp Arg Val Ser Arg
        115                 120                 125 gtg atg gta tgg atg ctg ttg ggt gca ctg ctc tta tcc tgt ggt agt      432
Val Met Val Trp Met Leu Leu Gly Ala Leu Leu Leu Ser Cys Gly Ser
    130                 135                 140 acc gca tct ctg atc aat gag ttt aag ctc tat tct gtc ttt agg gga      480
Thr Ala Ser Leu Ile Asn Glu Phe Lys Leu Tyr Ser Val Phe Arg Gly
145                 150                 155                 160 att gag gcc acc agg aat gtg act gaa cac ttc aga aag aag agg agt      528
Ile Glu Ala Thr Arg Asn Val Thr Glu His Phe Arg Lys Lys Arg Ser
                165                 170                 175 gag tat tat ctg atc cat gtt ctt ggg act ctg tgg tac ctg cct ccc      576
Glu Tyr Tyr Leu Ile His Val Leu Gly Thr Leu Trp Tyr Leu Pro Pro
            180                 185                 190 tta att gtg tcc ctg gcc tcc tac tct ttg ctc atc ttc tcc ctg ggg      624
Leu Ile Val Ser Leu Ala Ser Tyr Ser Leu Leu Ile Phe Ser Leu Gly
        195                 200                 205 agg cac aca cgg cag atg ctg caa aat ggg aca agc tcc aga gat cca      672
Arg His Thr Arg Gln Met Leu Gln Asn Gly Thr Ser Ser Arg Asp Pro
    210                 215                 220 acc act gag gcc cac aag agg gcc atc aga atc atc ctt tcc ttc ttc      720
Thr Thr Glu Ala His Lys Arg Ala Ile Arg Ile Ile Leu Ser Phe Phe
225                 230                 235                 240 ttt ctc ttc tta ctt tac ttt ctt gct ttc tta att gca tca ttt ggt      768
Phe Leu Phe Leu Leu Tyr Phe Leu Ala Phe Leu Ile Ala Ser Phe Gly
                245                 250                 255 aat ttc cta cca aaa acc aag atg gct aag atg att ggc gaa gta atg      816
Asn Phe Leu Pro Lys Thr Lys Met Ala Lys Met Ile Gly Glu Val Met
```

```
                    260                 265                 270
aca atg ttt tat cct gct ggc cac tca ttt att ctc att ctg ggg aac       864
Thr Met Phe Tyr Pro Ala Gly His Ser Phe Ile Leu Ile Leu Gly Asn
            275                 280                 285 agt aag ctg aag cag aca ttt gta gtg atg ctc cgg tgt gag tct ggt       912
Ser Lys Leu Lys Gln Thr Phe Val Val Met Leu Arg Cys Glu Ser Gly
    290                 295                 300 cat ctg aag cct gga tcc aag gga ccc att ttc tct tag                   951
His Leu Lys Pro Gly Ser Lys Gly Pro Ile Phe Ser
305                 310                 315

<210> SEQ ID NO 26
<211> LENGTH: 316
<212> TYPE: PRT
<213> ORGANISM: Homo sapiens

<400> SEQUENCE: 26

Met Met Gly Leu Thr Glu Gly Val Phe Leu Ile Leu Ser Gly Thr Gln
1               5                   10                  15

Phe Thr Leu Gly Ile Leu Val Asn Cys Phe Ile Glu Leu Val Asn Gly
            20                  25                  30

Ser Ser Trp Phe Lys Thr Lys Arg Met Ser Leu Ser Asp Phe Ile Ile
        35                  40                  45

Thr Thr Leu Ala Leu Leu Arg Ile Ile Leu Leu Cys Ile Ile Leu Thr
    50                  55                  60

Asp Ser Phe Leu Ile Glu Phe Ser Pro Asn Thr His Asp Ser Gly Ile
65                  70                  75                  80

Ile Met Gln Ile Ile Asp Val Ser Trp Thr Phe Thr Asn His Leu Ser
                85                  90                  95

Ile Trp Leu Ala Thr Cys Leu Gly Val Leu Tyr Cys Leu Lys Ile Ala
            100                 105                 110

Ser Phe Ser His Pro Thr Phe Leu Trp Leu Lys Trp Arg Val Ser Arg
        115                 120                 125

Val Met Val Trp Met Leu Leu Gly Ala Leu Leu Leu Ser Cys Gly Ser
    130                 135                 140

Thr Ala Ser Leu Ile Asn Glu Phe Lys Leu Tyr Ser Val Phe Arg Gly
145                 150                 155                 160

Ile Glu Ala Thr Arg Asn Val Thr Glu His Phe Arg Lys Lys Arg Ser
                165                 170                 175

Glu Tyr Tyr Leu Ile His Val Leu Gly Thr Leu Trp Tyr Leu Pro Pro
            180                 185                 190

Leu Ile Val Ser Leu Ala Ser Tyr Ser Leu Leu Ile Phe Ser Leu Gly
        195                 200                 205

Arg His Thr Arg Gln Met Leu Gln Asn Gly Thr Ser Ser Arg Asp Pro
    210                 215                 220

Thr Thr Glu Ala His Lys Arg Ala Ile Arg Ile Ile Leu Ser Phe Phe
225                 230                 235                 240

Phe Leu Phe Leu Leu Tyr Phe Leu Ala Phe Leu Ile Ala Ser Phe Gly
                245                 250                 255

Asn Phe Leu Pro Lys Thr Lys Met Ala Lys Met Ile Gly Glu Val Met
            260                 265                 270

Thr Met Phe Tyr Pro Ala Gly His Ser Phe Ile Leu Ile Leu Gly Asn
        275                 280                 285

Ser Lys Leu Lys Gln Thr Phe Val Val Met Leu Arg Cys Glu Ser Gly
    290                 295                 300

His Leu Lys Pro Gly Ser Lys Gly Pro Ile Phe Ser
```

<210> SEQ ID NO 27
<211> LENGTH: 900
<212> TYPE: DNA
<213> ORGANISM: Homo sapiens
<220> FEATURE:
<221> NAME/KEY: CDS
<222> LOCATION: (1)..(900)

<400> SEQUENCE: 27

| | | | | | | | | | | | | | | | | |
|---|---|---|---|---|---|---|---|---|---|---|---|---|---|---|---|---|
| atg | ctt | cgg | tta | ttc | tat | ttc | tct | gct | att | att | gcc | tca | gtt | att | tta | 48 |
| Met | Leu | Arg | Leu | Phe | Tyr | Phe | Ser | Ala | Ile | Ile | Ala | Ser | Val | Ile | Leu | |
| 1 | | | | 5 | | | | | 10 | | | | | 15 | | |
| aat | ttt | gta | gga | atc | att | atg | aat | ctg | ttt | att | aca | gtg | gtc | aat | tgc | 96 |
| Asn | Phe | Val | Gly | Ile | Ile | Met | Asn | Leu | Phe | Ile | Thr | Val | Val | Asn | Cys | |
| | | | 20 | | | | | 25 | | | | | 30 | | | |
| aaa | act | tgg | gtc | aaa | agc | cat | aga | atc | tcc | tct | tct | gat | agg | att | ctg | 144 |
| Lys | Thr | Trp | Val | Lys | Ser | His | Arg | Ile | Ser | Ser | Ser | Asp | Arg | Ile | Leu | |
| | | 35 | | | | | 40 | | | | | 45 | | | | |
| ttc | agc | ctg | ggc | atc | acc | agg | ttt | ctt | atg | ctg | gga | cta | ttt | ctg | gtg | 192 |
| Phe | Ser | Leu | Gly | Ile | Thr | Arg | Phe | Leu | Met | Leu | Gly | Leu | Phe | Leu | Val | |
| 50 | | | | | 55 | | | | | 60 | | | | | | |
| aac | acc | atc | tac | ttc | gtc | tct | tca | aat | acg | gaa | agg | tca | gtc | tac | ctg | 240 |
| Asn | Thr | Ile | Tyr | Phe | Val | Ser | Ser | Asn | Thr | Glu | Arg | Ser | Val | Tyr | Leu | |
| 65 | | | | | 70 | | | | | 75 | | | | | 80 | |
| tct | gct | ttt | ttt | gtg | ttg | tgt | ttc | atg | ttt | ttg | gac | tcg | agc | agt | gtc | 288 |
| Ser | Ala | Phe | Phe | Val | Leu | Cys | Phe | Met | Phe | Leu | Asp | Ser | Ser | Ser | Val | |
| | | | | 85 | | | | | 90 | | | | | 95 | | |
| tgg | ttt | gtg | acc | ttg | ctc | aat | atc | ttg | tac | tgt | gtg | aag | att | act | aac | 336 |
| Trp | Phe | Val | Thr | Leu | Leu | Asn | Ile | Leu | Tyr | Cys | Val | Lys | Ile | Thr | Asn | |
| | | | 100 | | | | | 105 | | | | | 110 | | | |
| ttc | caa | cac | tca | gtg | ttt | ctc | ctg | ctg | aag | cgg | aat | atc | tcc | cca | aag | 384 |
| Phe | Gln | His | Ser | Val | Phe | Leu | Leu | Leu | Lys | Arg | Asn | Ile | Ser | Pro | Lys | |
| | | 115 | | | | | 120 | | | | | 125 | | | | |
| atc | ccc | agg | ctg | ctg | ctg | gcc | tgt | gtg | ctg | att | tct | gct | ttc | acc | act | 432 |
| Ile | Pro | Arg | Leu | Leu | Leu | Ala | Cys | Val | Leu | Ile | Ser | Ala | Phe | Thr | Thr | |
| 130 | | | | | 135 | | | | | 140 | | | | | | |
| tgc | ctg | tac | atc | acg | ctt | agc | cag | gca | tca | cct | ttt | cct | gaa | ctt | gtg | 480 |
| Cys | Leu | Tyr | Ile | Thr | Leu | Ser | Gln | Ala | Ser | Pro | Phe | Pro | Glu | Leu | Val | |
| 145 | | | | | 150 | | | | | 155 | | | | | 160 | |
| act | acg | aga | aat | aac | aca | tca | ttt | aat | atc | agt | gag | ggc | atc | ttg | tct | 528 |
| Thr | Thr | Arg | Asn | Asn | Thr | Ser | Phe | Asn | Ile | Ser | Glu | Gly | Ile | Leu | Ser | |
| | | | | 165 | | | | | 170 | | | | | 175 | | |
| tta | gtg | gtt | tct | ttg | gtc | ttg | agc | tca | tct | ctc | cag | ttc | atc | att | aat | 576 |
| Leu | Val | Val | Ser | Leu | Val | Leu | Ser | Ser | Ser | Leu | Gln | Phe | Ile | Ile | Asn | |
| | | | | 180 | | | | | 185 | | | | | 190 | | |
| gtg | act | tct | gct | tcc | ttg | cta | ata | cac | tcc | ttg | agg | aga | cat | ata | cag | 624 |
| Val | Thr | Ser | Ala | Ser | Leu | Leu | Ile | His | Ser | Leu | Arg | Arg | His | Ile | Gln | |
| | | | 195 | | | | | 200 | | | | | 205 | | | |
| aag | atg | cag | aaa | aat | gcc | act | ggt | ttc | tgg | aat | ccc | cag | acg | gaa | gct | 672 |
| Lys | Met | Gln | Lys | Asn | Ala | Thr | Gly | Phe | Trp | Asn | Pro | Gln | Thr | Glu | Ala | |
| | 210 | | | | | 215 | | | | | 220 | | | | | |
| cat | gta | ggt | gct | atg | aag | ctg | atg | gtc | tat | ttc | ctc | atc | ctc | tac | att | 720 |
| His | Val | Gly | Ala | Met | Lys | Leu | Met | Val | Tyr | Phe | Leu | Ile | Leu | Tyr | Ile | |
| 225 | | | | | 230 | | | | | 235 | | | | | 240 | |
| cca | tat | tca | gtt | gct | acc | ctg | gtc | cag | tat | ctc | ccc | ttt | tat | gca | ggg | 768 |
| Pro | Tyr | Ser | Val | Ala | Thr | Leu | Val | Gln | Tyr | Leu | Pro | Phe | Tyr | Ala | Gly | |
| | | | | 245 | | | | | 250 | | | | | 255 | | |
| atg | gat | atg | ggg | acc | aaa | tcc | att | tgt | ctg | att | ttt | gcc | acc | ctt | tac | 816 |
| Met | Asp | Met | Gly | Thr | Lys | Ser | Ile | Cys | Leu | Ile | Phe | Ala | Thr | Leu | Tyr | |
| | | | 260 | | | | | 265 | | | | | 270 | | | |

```
tct cca gga cat tct gtt ctc att att atc aca cat cct aaa ctg aaa     864
Ser Pro Gly His Ser Val Leu Ile Ile Ile Thr His Pro Lys Leu Lys
    275                 280                 285 aca aca gca aag aag att ctt tgt ttc aaa aaa tag                     900
Thr Thr Ala Lys Lys Ile Leu Cys Phe Lys Lys
    290                 295
```

<210> SEQ ID NO 28
<211> LENGTH: 299
<212> TYPE: PRT
<213> ORGANISM: Homo sapiens

<400> SEQUENCE: 28

```
Met Leu Arg Leu Phe Tyr Phe Ser Ala Ile Ala Ser Val Ile Leu
1               5                   10                  15

Asn Phe Val Gly Ile Ile Met Asn Leu Phe Ile Thr Val Val Asn Cys
                20                  25                  30

Lys Thr Trp Val Lys Ser His Arg Ile Ser Ser Asp Arg Ile Leu
            35                  40                  45

Phe Ser Leu Gly Ile Thr Arg Phe Leu Met Leu Gly Leu Phe Leu Val
50                  55                  60

Asn Thr Ile Tyr Phe Val Ser Ser Asn Thr Glu Arg Ser Val Tyr Leu
65                  70                  75                  80

Ser Ala Phe Phe Val Leu Cys Phe Met Phe Leu Asp Ser Ser Ser Val
                85                  90                  95

Trp Phe Val Thr Leu Leu Asn Ile Leu Tyr Cys Val Lys Ile Thr Asn
                100                 105                 110

Phe Gln His Ser Val Phe Leu Leu Lys Arg Asn Ile Ser Pro Lys
            115                 120                 125

Ile Pro Arg Leu Leu Leu Ala Cys Val Leu Ile Ser Ala Phe Thr Thr
130                 135                 140

Cys Leu Tyr Ile Thr Leu Ser Gln Ala Ser Pro Phe Pro Glu Leu Val
145                 150                 155                 160

Thr Thr Arg Asn Asn Thr Ser Phe Asn Ile Ser Glu Gly Ile Leu Ser
                165                 170                 175

Leu Val Val Ser Leu Val Leu Ser Ser Ser Leu Gln Phe Ile Ile Asn
                180                 185                 190

Val Thr Ser Ala Ser Leu Leu Ile His Ser Leu Arg Arg His Ile Gln
                195                 200                 205

Lys Met Gln Lys Asn Ala Thr Gly Phe Trp Asn Pro Gln Thr Glu Ala
210                 215                 220

His Val Gly Ala Met Lys Leu Met Val Tyr Phe Leu Ile Leu Tyr Ile
225                 230                 235                 240

Pro Tyr Ser Val Ala Thr Leu Val Gln Tyr Leu Pro Phe Tyr Ala Gly
                245                 250                 255

Met Asp Met Gly Thr Lys Ser Ile Cys Leu Ile Phe Ala Thr Leu Tyr
                260                 265                 270

Ser Pro Gly His Ser Val Leu Ile Ile Ile Thr His Pro Lys Leu Lys
                275                 280                 285

Thr Thr Ala Lys Lys Ile Leu Cys Phe Lys Lys
                290                 295
```

<210> SEQ ID NO 29
<211> LENGTH: 900
<212> TYPE: DNA
<213> ORGANISM: Homo sapiens
<220> FEATURE:

<221> NAME/KEY: CDS
<222> LOCATION: (1)..(900)

<400> SEQUENCE: 29

```
atg ctg agc gct ggc cta gga ctg ctg atg ctg gtg gca gtg gtt gaa        48
Met Leu Ser Ala Gly Leu Gly Leu Leu Met Leu Val Ala Val Val Glu
1               5                   10                  15 ttt ctc atc ggt tta att gga aat gga agc ctg gtg gtc tgg agt ttt        96
Phe Leu Ile Gly Leu Ile Gly Asn Gly Ser Leu Val Val Trp Ser Phe
            20                  25                  30 aga gaa tgg atc aga aaa ttc aac tgg tcc tca tat aac ctc att atc       144
Arg Glu Trp Ile Arg Lys Phe Asn Trp Ser Ser Tyr Asn Leu Ile Ile
        35                  40                  45 ctg ggc ctg gct ggc tgc cga ttt ctc ctg cag tgg ctg atc att ttg       192
Leu Gly Leu Ala Gly Cys Arg Phe Leu Leu Gln Trp Leu Ile Ile Leu
    50                  55                  60 gac tta agc ttg ttt cca ctt ttc cag agc agc cgt tgg ctt cgc tat       240
Asp Leu Ser Leu Phe Pro Leu Phe Gln Ser Ser Arg Trp Leu Arg Tyr
65                  70                  75                  80 ctt agt atc ttc tgg gtc ctg gta agc cag gcc agc tta tgg ttt gcc       288
Leu Ser Ile Phe Trp Val Leu Val Ser Gln Ala Ser Leu Trp Phe Ala
                85                  90                  95 acc ttc ctc agt gtc ttc tat tgc aag aag atc acg acc ttc gat cgc       336
Thr Phe Leu Ser Val Phe Tyr Cys Lys Lys Ile Thr Thr Phe Asp Arg
            100                 105                 110 ccg gcc tac ttg tgg ctg aag cag agg gcc tat aac ctg agt ctc tgg       384
Pro Ala Tyr Leu Trp Leu Lys Gln Arg Ala Tyr Asn Leu Ser Leu Trp
        115                 120                 125 tgc ctt ctg ggc tac ttt ata atc aat ttg tta ctt aca gtc caa att       432
Cys Leu Leu Gly Tyr Phe Ile Ile Asn Leu Leu Leu Thr Val Gln Ile
    130                 135                 140 ggc tta aca ttc tat cat cct ccc caa gga aac agc agc att cgg tat       480
Gly Leu Thr Phe Tyr His Pro Pro Gln Gly Asn Ser Ser Ile Arg Tyr
145                 150                 155                 160 ccc ttt gaa agc tgg cag tac ctg tat gca ttt cag ctc aat tca gga       528
Pro Phe Glu Ser Trp Gln Tyr Leu Tyr Ala Phe Gln Leu Asn Ser Gly
                165                 170                 175 agt tat ttg cct tta gtg gtg ttt ctt gtt tcc tct ggg atg ctg att       576
Ser Tyr Leu Pro Leu Val Val Phe Leu Val Ser Ser Gly Met Leu Ile
            180                 185                 190 gtc tct ttg tat aca cac cac aag aag atg aag gtc cat tca gct ggt       624
Val Ser Leu Tyr Thr His His Lys Lys Met Lys Val His Ser Ala Gly
        195                 200                 205 agg agg gat gtc cgg gcc aag gct cac atc act gcg ctg aag tcc ttg       672
Arg Arg Asp Val Arg Ala Lys Ala His Ile Thr Ala Leu Lys Ser Leu
    210                 215                 220 ggc tgc ttc ctc tta ctt cac ctg gtt tat atc atg gcc agc ccc ttc       720
Gly Cys Phe Leu Leu Leu His Leu Val Tyr Ile Met Ala Ser Pro Phe
225                 230                 235                 240 tcc atc acc tcc aag act tat cct cct gat ctc acc agt gtc ttc atc       768
Ser Ile Thr Ser Lys Thr Tyr Pro Pro Asp Leu Thr Ser Val Phe Ile
                245                 250                 255 tgg gag aca ctc atg gca gcc tat cct tct ctt cat tct ctc ata ttg       816
Trp Glu Thr Leu Met Ala Ala Tyr Pro Ser Leu His Ser Leu Ile Leu
            260                 265                 270 atc atg ggg att cct agg gtg aag cag act tgt cag aag atc ctg tgg       864
Ile Met Gly Ile Pro Arg Val Lys Gln Thr Cys Gln Lys Ile Leu Trp
        275                 280                 285 aag aca gtg tgt gct cgg aga tgc tgg ggc cca tga                       900
Lys Thr Val Cys Ala Arg Arg Cys Trp Gly Pro
    290                 295
```

<210> SEQ ID NO 30
<211> LENGTH: 299
<212> TYPE: PRT
<213> ORGANISM: Homo sapiens

<400> SEQUENCE: 30

Met Leu Ser Ala Gly Leu Gly Leu Leu Met Leu Val Ala Val Val Glu
1               5                   10                  15

Phe Leu Ile Gly Leu Ile Gly Asn Gly Ser Leu Val Val Trp Ser Phe
            20                  25                  30

Arg Glu Trp Ile Arg Lys Phe Asn Trp Ser Ser Tyr Asn Leu Ile Ile
        35                  40                  45

Leu Gly Leu Ala Gly Cys Arg Phe Leu Leu Gln Trp Leu Ile Ile Leu
    50                  55                  60

Asp Leu Ser Leu Phe Pro Leu Phe Gln Ser Ser Arg Trp Leu Arg Tyr
65                  70                  75                  80

Leu Ser Ile Phe Trp Val Leu Val Ser Gln Ala Ser Leu Trp Phe Ala
                85                  90                  95

Thr Phe Leu Ser Val Phe Tyr Cys Lys Lys Ile Thr Thr Phe Asp Arg
            100                 105                 110

Pro Ala Tyr Leu Trp Leu Lys Gln Arg Ala Tyr Asn Leu Ser Leu Trp
        115                 120                 125

Cys Leu Leu Gly Tyr Phe Ile Ile Asn Leu Leu Leu Thr Val Gln Ile
    130                 135                 140

Gly Leu Thr Phe Tyr His Pro Pro Gln Gly Asn Ser Ser Ile Arg Tyr
145                 150                 155                 160

Pro Phe Glu Ser Trp Gln Tyr Leu Tyr Ala Phe Gln Leu Asn Ser Gly
                165                 170                 175

Ser Tyr Leu Pro Leu Val Val Phe Leu Val Ser Ser Gly Met Leu Ile
            180                 185                 190

Val Ser Leu Tyr Thr His His Lys Lys Met Lys Val His Ser Ala Gly
        195                 200                 205

Arg Arg Asp Val Arg Ala Lys Ala His Ile Thr Ala Leu Lys Ser Leu
    210                 215                 220

Gly Cys Phe Leu Leu Leu His Leu Val Tyr Ile Met Ala Ser Pro Phe
225                 230                 235                 240

Ser Ile Thr Ser Lys Thr Tyr Pro Pro Asp Leu Thr Ser Val Phe Ile
                245                 250                 255

Trp Glu Thr Leu Met Ala Ala Tyr Pro Ser Leu His Ser Leu Ile Leu
            260                 265                 270

Ile Met Gly Ile Pro Arg Val Lys Gln Thr Cys Gln Lys Ile Leu Trp
        275                 280                 285

Lys Thr Val Cys Ala Arg Arg Cys Trp Gly Pro
    290                 295

<210> SEQ ID NO 31
<211> LENGTH: 957
<212> TYPE: DNA
<213> ORGANISM: Homo sapiens
<220> FEATURE:
<221> NAME/KEY: CDS
<222> LOCATION: (1)..(957)

<400> SEQUENCE: 31 atg gca gat aaa gtg cag act act tta ttg ttc tta gca gtt gga gag    48
Met Ala Asp Lys Val Gln Thr Thr Leu Leu Phe Leu Ala Val Gly Glu
1               5                   10                  15

| | | | | | | | | | | | | | | | | |
|---|---|---|---|---|---|---|---|---|---|---|---|---|---|---|---|---|
| ttt | tca | gtg | ggg | atc | tta | ggg | aat | gca | ttc | att | gga | ttg | gta | aac | tgc | 96 |
| Phe | Ser | Val | Gly | Ile | Leu | Gly | Asn | Ala | Phe | Ile | Gly | Leu | Val | Asn | Cys | |
| | | 20 | | | | | 25 | | | | | 30 | | | | |
| atg | gac | tgg | gtc | aag | aag | agg | aaa | att | gcc | tcc | att | gat | tta | atc | ctc | 144 |
| Met | Asp | Trp | Val | Lys | Lys | Arg | Lys | Ile | Ala | Ser | Ile | Asp | Leu | Ile | Leu | |
| | | | 35 | | | | | 40 | | | | | 45 | | | |
| aca | agt | ctg | gcc | ata | tcc | aga | att | tgt | cta | ttg | tgt | gta | ata | cta | tta | 192 |
| Thr | Ser | Leu | Ala | Ile | Ser | Arg | Ile | Cys | Leu | Leu | Cys | Val | Ile | Leu | Leu | |
| | 50 | | | | | 55 | | | | | 60 | | | | | |
| gat | tgt | ttt | ata | ttg | gtg | cta | tat | cca | gat | gtc | tat | gcc | act | ggt | aaa | 240 |
| Asp | Cys | Phe | Ile | Leu | Val | Leu | Tyr | Pro | Asp | Val | Tyr | Ala | Thr | Gly | Lys | |
| 65 | | | | | 70 | | | | | 75 | | | | | 80 | |
| gaa | atg | aga | atc | att | gac | ttc | ttc | tgg | aca | cta | acc | aat | cat | tta | agt | 288 |
| Glu | Met | Arg | Ile | Ile | Asp | Phe | Phe | Trp | Thr | Leu | Thr | Asn | His | Leu | Ser | |
| | | | | 85 | | | | | 90 | | | | | 95 | | |
| atc | tgg | ttt | gca | acc | tgc | ctc | agc | att | tac | tat | ttc | ttc | aag | ata | ggt | 336 |
| Ile | Trp | Phe | Ala | Thr | Cys | Leu | Ser | Ile | Tyr | Tyr | Phe | Phe | Lys | Ile | Gly | |
| | | | 100 | | | | | 105 | | | | | 110 | | | |
| aat | ttc | ttt | cac | cca | ctt | ttc | ctc | tgg | atg | aag | tgg | aga | att | gac | agg | 384 |
| Asn | Phe | Phe | His | Pro | Leu | Phe | Leu | Trp | Met | Lys | Trp | Arg | Ile | Asp | Arg | |
| | | 115 | | | | | 120 | | | | | 125 | | | | |
| gtg | att | tcc | tgg | att | cta | ctg | ggg | tgc | gtg | gtt | ctc | tct | gtg | ttt | att | 432 |
| Val | Ile | Ser | Trp | Ile | Leu | Leu | Gly | Cys | Val | Val | Leu | Ser | Val | Phe | Ile | |
| | 130 | | | | | 135 | | | | | 140 | | | | | |
| agc | ctt | cca | gcc | act | gag | aat | ttg | aac | gct | gat | ttc | agg | ttt | tgt | gtg | 480 |
| Ser | Leu | Pro | Ala | Thr | Glu | Asn | Leu | Asn | Ala | Asp | Phe | Arg | Phe | Cys | Val | |
| 145 | | | | | 150 | | | | | 155 | | | | | 160 | |
| aag | gca | aag | agg | aaa | aca | aac | tta | act | tgg | agt | tgc | aga | gta | aat | aaa | 528 |
| Lys | Ala | Lys | Arg | Lys | Thr | Asn | Leu | Thr | Trp | Ser | Cys | Arg | Val | Asn | Lys | |
| | | | | 165 | | | | | 170 | | | | | 175 | | |
| act | caa | cat | gct | tct | acc | aag | tta | ttt | ctc | aac | ctg | gca | acg | ctg | ctc | 576 |
| Thr | Gln | His | Ala | Ser | Thr | Lys | Leu | Phe | Leu | Asn | Leu | Ala | Thr | Leu | Leu | |
| | | | 180 | | | | | 185 | | | | | 190 | | | |
| ccc | ttt | tgt | gtg | tgc | cta | atg | tcc | ttt | ttc | ctc | ttg | atc | ctc | tcc | ctg | 624 |
| Pro | Phe | Cys | Val | Cys | Leu | Met | Ser | Phe | Phe | Leu | Leu | Ile | Leu | Ser | Leu | |
| | | 195 | | | | | 200 | | | | | 205 | | | | |
| cgg | aga | cat | atc | agg | cga | atg | cag | ctc | agt | gcc | aca | ggg | tgc | aga | gac | 672 |
| Arg | Arg | His | Ile | Arg | Arg | Met | Gln | Leu | Ser | Ala | Thr | Gly | Cys | Arg | Asp | |
| | 210 | | | | | 215 | | | | | 220 | | | | | |
| ccc | agc | aca | gaa | gcc | cat | gtg | aga | gcc | ctg | aaa | gct | gtc | att | tcc | ttc | 720 |
| Pro | Ser | Thr | Glu | Ala | His | Val | Arg | Ala | Leu | Lys | Ala | Val | Ile | Ser | Phe | |
| 225 | | | | | 230 | | | | | 235 | | | | | 240 | |
| ctt | ctc | ctc | ttt | att | gcc | tac | tat | ttg | tcc | ttt | ctc | att | gcc | acc | tcc | 768 |
| Leu | Leu | Leu | Phe | Ile | Ala | Tyr | Tyr | Leu | Ser | Phe | Leu | Ile | Ala | Thr | Ser | |
| | | | | 245 | | | | | 250 | | | | | 255 | | |
| agc | tac | ttt | atg | cca | gag | acg | gaa | tta | gct | gtg | att | ttt | ggt | gag | tcc | 816 |
| Ser | Tyr | Phe | Met | Pro | Glu | Thr | Glu | Leu | Ala | Val | Ile | Phe | Gly | Glu | Ser | |
| | | | 260 | | | | | 265 | | | | | 270 | | | |
| ata | gct | cta | atc | tac | ccc | tca | agt | cat | tca | ttt | atc | cta | ata | ctg | ggg | 864 |
| Ile | Ala | Leu | Ile | Tyr | Pro | Ser | Ser | His | Ser | Phe | Ile | Leu | Ile | Leu | Gly | |
| | | 275 | | | | | 280 | | | | | 285 | | | | |
| aac | aat | aaa | tta | aga | cat | gca | tct | cta | aag | gtg | att | tgg | aaa | gta | atg | 912 |
| Asn | Asn | Lys | Leu | Arg | His | Ala | Ser | Leu | Lys | Val | Ile | Trp | Lys | Val | Met | |
| | 290 | | | | | 295 | | | | | 300 | | | | | |
| tct | att | cta | aaa | gga | aga | aaa | ttc | caa | caa | cat | aaa | caa | atc | tga | | 957 |
| Ser | Ile | Leu | Lys | Gly | Arg | Lys | Phe | Gln | Gln | His | Lys | Gln | Ile | | | |
| 305 | | | | | 310 | | | | | 315 | | | | | | |

<210> SEQ ID NO 32
<211> LENGTH: 318

<212> TYPE: PRT
<213> ORGANISM: Homo sapiens

<400> SEQUENCE: 32

```
Met Ala Asp Lys Val Gln Thr Thr Leu Leu Phe Leu Ala Val Gly Glu
1               5                   10                  15

Phe Ser Val Gly Ile Leu Gly Asn Ala Phe Ile Gly Leu Val Asn Cys
            20                  25                  30

Met Asp Trp Val Lys Arg Lys Ile Ala Ser Ile Asp Leu Ile Leu
        35                  40                  45

Thr Ser Leu Ala Ile Ser Arg Ile Cys Leu Leu Cys Val Ile Leu Leu
    50                  55                  60

Asp Cys Phe Ile Leu Val Leu Tyr Pro Asp Val Tyr Ala Thr Gly Lys
65                  70                  75                  80

Glu Met Arg Ile Ile Asp Phe Phe Trp Thr Leu Thr Asn His Leu Ser
                85                  90                  95

Ile Trp Phe Ala Thr Cys Leu Ser Ile Tyr Tyr Phe Phe Lys Ile Gly
            100                 105                 110

Asn Phe Phe His Pro Leu Phe Leu Trp Met Lys Trp Arg Ile Asp Arg
        115                 120                 125

Val Ile Ser Trp Ile Leu Leu Gly Cys Val Val Leu Ser Val Phe Ile
    130                 135                 140

Ser Leu Pro Ala Thr Glu Asn Leu Asn Ala Asp Phe Arg Phe Cys Val
145                 150                 155                 160

Lys Ala Lys Arg Lys Thr Asn Leu Thr Trp Ser Cys Arg Val Asn Lys
                165                 170                 175

Thr Gln His Ala Ser Thr Lys Leu Phe Leu Asn Leu Ala Thr Leu Leu
            180                 185                 190

Pro Phe Cys Val Cys Leu Met Ser Phe Phe Leu Leu Ile Leu Ser Leu
        195                 200                 205

Arg Arg His Ile Arg Arg Met Gln Leu Ser Ala Thr Gly Cys Arg Asp
    210                 215                 220

Pro Ser Thr Glu Ala His Val Arg Ala Leu Lys Ala Val Ile Ser Phe
225                 230                 235                 240

Leu Leu Leu Phe Ile Ala Tyr Tyr Leu Ser Phe Leu Ile Ala Thr Ser
                245                 250                 255

Ser Tyr Phe Met Pro Glu Thr Glu Leu Ala Val Ile Phe Gly Glu Ser
            260                 265                 270

Ile Ala Leu Ile Tyr Pro Ser Ser His Ser Phe Ile Leu Ile Leu Gly
        275                 280                 285

Asn Asn Lys Leu Arg His Ala Ser Leu Lys Val Ile Trp Lys Val Met
    290                 295                 300

Ser Ile Leu Lys Gly Arg Lys Phe Gln Gln His Lys Gln Ile
305                 310                 315
```

<210> SEQ ID NO 33
<211> LENGTH: 930
<212> TYPE: DNA
<213> ORGANISM: Homo sapiens
<220> FEATURE:
<221> NAME/KEY: CDS
<222> LOCATION: (1)..(930)

<400> SEQUENCE: 33

```
atg ttc agt cct gca gat aac atc ttt ata atc cta ata act gga gaa     48
Met Phe Ser Pro Ala Asp Asn Ile Phe Ile Ile Leu Ile Thr Gly Glu
1               5                   10                  15
```

| | | |
|---|---|---|
| ttc ata cta gga ata ttg ggg aat gga tac att gca cta gtc aac tgg<br>Phe Ile Leu Gly Ile Leu Gly Asn Gly Tyr Ile Ala Leu Val Asn Trp<br>20       25        30 | 96 | |
| att gac tgg att aag aag aaa aag att tcc aca gtt gac tac atc ctt<br>Ile Asp Trp Ile Lys Lys Lys Lys Ile Ser Thr Val Asp Tyr Ile Leu<br>35         40          45 | 144 | |
| acc aat tta gtt atc gcc aga att tgt ttg atc agt gta atg gtt gta<br>Thr Asn Leu Val Ile Ala Arg Ile Cys Leu Ile Ser Val Met Val Val<br>50        55            60 | 192 | |
| aat ggc att gta ata gta ctg aac cca gat gtt tat aca aaa aat aaa<br>Asn Gly Ile Val Ile Val Leu Asn Pro Asp Val Tyr Thr Lys Asn Lys<br>65        70           75           80 | 240 | |
| caa cag ata gtc att ttt acc ttc tgg aca ttt gcc aac tac tta aat<br>Gln Gln Ile Val Ile Phe Thr Phe Trp Thr Phe Ala Asn Tyr Leu Asn<br>85           90           95 | 288 | |
| atg tgg att acc acc tgc ctt aat gtc ttc tat ttt ctg aag ata gcc<br>Met Trp Ile Thr Thr Cys Leu Asn Val Phe Tyr Phe Leu Lys Ile Ala<br>100        105         110 | 336 | |
| agt tcc tct cat cca ctt ttt ctc tgg ctg aag tgg aaa att gat atg<br>Ser Ser Ser His Pro Leu Phe Leu Trp Leu Lys Trp Lys Ile Asp Met<br>115        120          125 | 384 | |
| gtg gtg cac tgg atc ctg ctg gga tgc ttt gcc att tcc ttg ttg gtc<br>Val Val His Trp Ile Leu Leu Gly Cys Phe Ala Ile Ser Leu Leu Val<br>130        135         140 | 432 | |
| agc ctt ata gca gca ata gta ctg agt tgt gat tat agg ttt cat gca<br>Ser Leu Ile Ala Ala Ile Val Leu Ser Cys Asp Tyr Arg Phe His Ala<br>145       150             155           160 | 480 | |
| att gcc aaa cat aaa aga aac att act gaa atg ttc cat gtg agt aaa<br>Ile Ala Lys His Lys Arg Asn Ile Thr Glu Met Phe His Val Ser Lys<br>165         170          175 | 528 | |
| ata cca tac ttt gaa ccc ttg act ctc ttt aac ctg ttt gca att gtc<br>Ile Pro Tyr Phe Glu Pro Leu Thr Leu Phe Asn Leu Phe Ala Ile Val<br>180         185          190 | 576 | |
| cca ttt att gtg tca ctg ata tca ttt ttc ctt tta gta aga tct tta<br>Pro Phe Ile Val Ser Leu Ile Ser Phe Phe Leu Leu Val Arg Ser Leu<br>195         200          205 | 624 | |
| tgg aga cat acc aag caa ata aaa ctc tat gct acc ggc agt aga gac<br>Trp Arg His Thr Lys Gln Ile Lys Leu Tyr Ala Thr Gly Ser Arg Asp<br>210        215           220 | 672 | |
| ccc agc aca gaa gtt cat gtg aga gcc att aaa act atg act tca ttt<br>Pro Ser Thr Glu Val His Val Arg Ala Ile Lys Thr Met Thr Ser Phe<br>225        230           235           240 | 720 | |
| atc ttc ttt ttc cta tac tat att tct tct att ttg atg acc ttt<br>Ile Phe Phe Phe Phe Leu Tyr Tyr Ile Ser Ser Ile Leu Met Thr Phe<br>245         250          255 | 768 | |
| agc tat ctt atg aca aaa tac aag tta gct gtg gag ttt gga gag att<br>Ser Tyr Leu Met Thr Lys Tyr Lys Leu Ala Val Glu Phe Gly Glu Ile<br>260          265           270 | 816 | |
| gca gca att ctc tac ccc ttg ggt cac tca ctt att tta att gtt tta<br>Ala Ala Ile Leu Tyr Pro Leu Gly His Ser Leu Ile Leu Ile Val Leu<br>275         280          285 | 864 | |
| aat aat aaa ctg agg cag aca ttt gtc aga atg ctg aca tgt aga aaa<br>Asn Asn Lys Leu Arg Gln Thr Phe Val Arg Met Leu Thr Cys Arg Lys<br>290         295          300 | 912 | |
| att gcc tgc atg ata tga<br>Ile Ala Cys Met Ile<br>305 | 930 | |

<210> SEQ ID NO 34
<211> LENGTH: 309
<212> TYPE: PRT

<213> ORGANISM: Homo sapiens

<400> SEQUENCE: 34

```
Met Phe Ser Pro Ala Asp Asn Ile Phe Ile Ile Leu Ile Thr Gly Glu
1               5                   10                  15
Phe Ile Leu Gly Ile Leu Gly Asn Gly Tyr Ile Ala Leu Val Asn Trp
            20                  25                  30
Ile Asp Trp Ile Lys Lys Lys Ile Ser Thr Val Asp Tyr Ile Leu
        35                  40                  45
Thr Asn Leu Val Ile Ala Arg Ile Cys Leu Ile Ser Val Met Val Val
50                  55                  60
Asn Gly Ile Val Ile Val Leu Asn Pro Asp Val Tyr Thr Lys Asn Lys
65                  70                  75                  80
Gln Gln Ile Val Ile Phe Thr Phe Trp Thr Phe Ala Asn Tyr Leu Asn
                85                  90                  95
Met Trp Ile Thr Thr Cys Leu Asn Val Phe Tyr Phe Leu Lys Ile Ala
            100                 105                 110
Ser Ser Ser His Pro Leu Phe Leu Trp Leu Lys Trp Lys Ile Asp Met
        115                 120                 125
Val Val His Trp Ile Leu Leu Gly Cys Phe Ala Ile Ser Leu Leu Val
130                 135                 140
Ser Leu Ile Ala Ala Ile Val Leu Ser Cys Asp Tyr Arg Phe His Ala
145                 150                 155                 160
Ile Ala Lys His Lys Arg Asn Ile Thr Glu Met Phe His Val Ser Lys
                165                 170                 175
Ile Pro Tyr Phe Glu Pro Leu Thr Leu Phe Asn Leu Phe Ala Ile Val
            180                 185                 190
Pro Phe Ile Val Ser Leu Ile Ser Phe Phe Leu Leu Val Arg Ser Leu
        195                 200                 205
Trp Arg His Thr Lys Gln Ile Lys Leu Tyr Ala Thr Gly Ser Arg Asp
210                 215                 220
Pro Ser Thr Glu Val His Val Arg Ala Ile Lys Thr Met Thr Ser Phe
225                 230                 235                 240
Ile Phe Phe Phe Phe Leu Tyr Tyr Ile Ser Ser Ile Leu Met Thr Phe
                245                 250                 255
Ser Tyr Leu Met Thr Lys Tyr Lys Leu Ala Val Glu Phe Gly Glu Ile
            260                 265                 270
Ala Ala Ile Leu Tyr Pro Leu Gly His Ser Leu Ile Leu Ile Val Leu
        275                 280                 285
Asn Asn Lys Leu Arg Gln Thr Phe Val Arg Met Leu Thr Cys Arg Lys
290                 295                 300
Ile Ala Cys Met Ile
305
```

<210> SEQ ID NO 35
<211> LENGTH: 939
<212> TYPE: DNA
<213> ORGANISM: Homo sapiens
<220> FEATURE:
<221> NAME/KEY: CDS
<222> LOCATION: (1)..(939)

<400> SEQUENCE: 35

```
atg cca agt gca ata gag gca ata tat att att tta att gct ggt gaa    48
Met Pro Ser Ala Ile Glu Ala Ile Tyr Ile Ile Leu Ile Ala Gly Glu
1               5                   10                  15 ttg acc ata ggg att tgg gga aat gga ttc att gta cta gtt aac tgc    96
```

```
                    Leu Thr Ile Gly Ile Trp Gly Asn Gly Phe Ile Val Leu Val Asn Cys
                            20                  25                  30 att gac tgg ctc aaa aga aga gat att tcc ttg att gac atc atc ctg            144
Ile Asp Trp Leu Lys Arg Arg Asp Ile Ser Leu Ile Asp Ile Ile Leu
        35                  40                  45 atc agc ttg gcc atc tcc aga atc tgt ctg ctg tgt gta ata tca tta            192
Ile Ser Leu Ala Ile Ser Arg Ile Cys Leu Leu Cys Val Ile Ser Leu
 50                  55                  60 gat ggc ttc ttt atg ctg ctc ttt cca ggt aca tat ggc aat agc gtg            240
Asp Gly Phe Phe Met Leu Leu Phe Pro Gly Thr Tyr Gly Asn Ser Val
 65                  70                  75                  80 cta gta agc att gtg aat gtt gtc tgg aca ttt gcc aat aat tca agt            288
Leu Val Ser Ile Val Asn Val Val Trp Thr Phe Ala Asn Asn Ser Ser
                85                  90                  95 ctc tgg ttt act tct tgc ctc agt atc ttc tat tta ctc aag ata gcc            336
Leu Trp Phe Thr Ser Cys Leu Ser Ile Phe Tyr Leu Leu Lys Ile Ala
            100                 105                 110 aat ata tcg cac cca ttt ttc ttc tgg ctg aag cta aag atc aac aag            384
Asn Ile Ser His Pro Phe Phe Phe Trp Leu Lys Leu Lys Ile Asn Lys
        115                 120                 125 gtc atg ctt gcg att ctt ctg ggg tcc ttt ctt atc tct tta att att            432
Val Met Leu Ala Ile Leu Leu Gly Ser Phe Leu Ile Ser Leu Ile Ile
    130                 135                 140 agt gtt cca aag aat gat gat atg tgg tat cac ctt ttc aaa gtc agt            480
Ser Val Pro Lys Asn Asp Asp Met Trp Tyr His Leu Phe Lys Val Ser
145                 150                 155                 160 cat gaa gaa aac att act tgg aaa ttc aaa gtg agt aaa att cca ggt            528
His Glu Glu Asn Ile Thr Trp Lys Phe Lys Val Ser Lys Ile Pro Gly
                165                 170                 175 act ttc aaa cag tta acc ctg aac ctg ggg gtg atg gtt ccc ttt atc            576
Thr Phe Lys Gln Leu Thr Leu Asn Leu Gly Val Met Val Pro Phe Ile
            180                 185                 190 ctt tgc ctg atc tca ttt ttc ttg tta ctt ttc tcc cta gtt aga cac            624
Leu Cys Leu Ile Ser Phe Phe Leu Leu Leu Phe Ser Leu Val Arg His
        195                 200                 205 acc aag cag att cga ctg cat gct aca ggg ttc aga gac ccc agt aca            672
Thr Lys Gln Ile Arg Leu His Ala Thr Gly Phe Arg Asp Pro Ser Thr
    210                 215                 220 gag gcc cac atg agg gcc ata aag gca gtg atc atc ttt ctg ctc ctc            720
Glu Ala His Met Arg Ala Ile Lys Ala Val Ile Ile Phe Leu Leu Leu
225                 230                 235                 240 ctc atc gtg tac tac cca gtc ttt ctt gtt atg acc tct agc gct ctg            768
Leu Ile Val Tyr Tyr Pro Val Phe Leu Val Met Thr Ser Ser Ala Leu
                245                 250                 255 att cct cag gga aaa tta gtg ttg atg att ggt gac ata gta act gtc            816
Ile Pro Gln Gly Lys Leu Val Leu Met Ile Gly Asp Ile Val Thr Val
            260                 265                 270 att ttc cca tca agc cat tca ttc att cta att atg gga aat agc aag            864
Ile Phe Pro Ser Ser His Ser Phe Ile Leu Ile Met Gly Asn Ser Lys
        275                 280                 285 ttg agg gaa gct ttt ctg aag atg tta aga ttt gtg aag tgt ttc ctt            912
Leu Arg Glu Ala Phe Leu Lys Met Leu Arg Phe Val Lys Cys Phe Leu
    290                 295                 300 aga aga aga aag cct ttt gtt cca tag                                        939
Arg Arg Arg Lys Pro Phe Val Pro
305                 310

<210> SEQ ID NO 36
<211> LENGTH: 312
<212> TYPE: PRT
<213> ORGANISM: Homo sapiens
```

<400> SEQUENCE: 36

Met Pro Ser Ala Ile Glu Ala Ile Tyr Ile Leu Ile Ala Gly Glu
1               5                   10                  15

Leu Thr Ile Gly Ile Trp Gly Asn Gly Phe Ile Val Leu Val Asn Cys
            20                  25                  30

Ile Asp Trp Leu Lys Arg Arg Asp Ile Ser Leu Ile Asp Ile Ile Leu
            35                  40                  45

Ile Ser Leu Ala Ile Ser Arg Ile Cys Leu Leu Cys Val Ile Ser Leu
50                  55                  60

Asp Gly Phe Phe Met Leu Leu Phe Pro Gly Thr Tyr Gly Asn Ser Val
65                  70                  75                  80

Leu Val Ser Ile Val Asn Val Val Trp Thr Phe Ala Asn Asn Ser Ser
                85                  90                  95

Leu Trp Phe Thr Ser Cys Leu Ser Ile Phe Tyr Leu Leu Lys Ile Ala
            100                 105                 110

Asn Ile Ser His Pro Phe Phe Phe Trp Leu Lys Leu Lys Ile Asn Lys
            115                 120                 125

Val Met Leu Ala Ile Leu Leu Gly Ser Phe Leu Ile Ser Leu Ile Ile
130                 135                 140

Ser Val Pro Lys Asn Asp Asp Met Trp Tyr His Leu Phe Lys Val Ser
145                 150                 155                 160

His Glu Glu Asn Ile Thr Trp Lys Phe Lys Val Ser Lys Ile Pro Gly
                165                 170                 175

Thr Phe Lys Gln Leu Thr Leu Asn Leu Gly Val Met Val Pro Phe Ile
            180                 185                 190

Leu Cys Leu Ile Ser Phe Phe Leu Leu Phe Ser Leu Val Arg His
            195                 200                 205

Thr Lys Gln Ile Arg Leu His Ala Thr Gly Phe Arg Asp Pro Ser Thr
            210                 215                 220

Glu Ala His Met Arg Ala Ile Lys Ala Val Ile Ile Phe Leu Leu Leu
225                 230                 235                 240

Leu Ile Val Tyr Tyr Pro Val Phe Leu Val Met Thr Ser Ser Ala Leu
                245                 250                 255

Ile Pro Gln Gly Lys Leu Val Leu Met Ile Gly Asp Ile Val Thr Val
            260                 265                 270

Ile Phe Pro Ser Ser His Ser Phe Ile Leu Ile Met Gly Asn Ser Lys
            275                 280                 285

Leu Arg Glu Ala Phe Leu Lys Met Leu Arg Phe Val Lys Cys Phe Leu
290                 295                 300

Arg Arg Arg Lys Pro Phe Val Pro
305                 310

<210> SEQ ID NO 37
<211> LENGTH: 924
<212> TYPE: DNA
<213> ORGANISM: Homo sapiens
<220> FEATURE:
<221> NAME/KEY: CDS
<222> LOCATION: (1)..(924)

<400> SEQUENCE: 37 atg cta cgt gta gtg gaa ggc atc ttc att ttt gtt gta gtt agt gag    48
Met Leu Arg Val Val Glu Gly Ile Phe Ile Phe Val Val Val Ser Glu
1               5                   10                  15 tca gtg ttt ggg gtt ttg ggg aat gga ttt att gga ctt gta aac tgc    96
Ser Val Phe Gly Val Leu Gly Asn Gly Phe Ile Gly Leu Val Asn Cys
            20                  25                  30

```
                    20                  25                  30
att gac tgt gcc aag aat aag tta tct acg att ggc ttt att ctc acc    144
Ile Asp Cys Ala Lys Asn Lys Leu Ser Thr Ile Gly Phe Ile Leu Thr
         35                  40                  45 ggc tta gct att tca aga att ttt ctg ata tgg ata ata att aca gat    192
Gly Leu Ala Ile Ser Arg Ile Phe Leu Ile Trp Ile Ile Ile Thr Asp
 50                  55                  60 gga ttt ata cag ata ttc tct cca aat ata tat gcc tcc ggt aac cta    240
Gly Phe Ile Gln Ile Phe Ser Pro Asn Ile Tyr Ala Ser Gly Asn Leu
 65                  70                  75                  80 att gaa tat att agt tac ttt tgg gta att ggt aat caa tca agt atg    288
Ile Glu Tyr Ile Ser Tyr Phe Trp Val Ile Gly Asn Gln Ser Ser Met
             85                  90                  95 tgg ttt gcc acc agc ctc agc atc ttc tat ttc ctg aag ata gca aat    336
Trp Phe Ala Thr Ser Leu Ser Ile Phe Tyr Phe Leu Lys Ile Ala Asn
                100                 105                 110 ttt tcc aac tac ata ttt ctc tgg ttg aag agc aga aca aat atg gtt    384
Phe Ser Asn Tyr Ile Phe Leu Trp Leu Lys Ser Arg Thr Asn Met Val
            115                 120                 125 ctt ccc ttc atg ata gta ttc tta ctt att tca tcg tta ctt aat ttt    432
Leu Pro Phe Met Ile Val Phe Leu Leu Ile Ser Ser Leu Leu Asn Phe
130                 135                 140 gca tac att gcg aag att ctt aat gat tat aaa acg aag aat gac aca    480
Ala Tyr Ile Ala Lys Ile Leu Asn Asp Tyr Lys Thr Lys Asn Asp Thr
145                 150                 155                 160 gtc tgg gat ctc aac atg tat aaa agt gaa tac ttt att aaa cag att    528
Val Trp Asp Leu Asn Met Tyr Lys Ser Glu Tyr Phe Ile Lys Gln Ile
                165                 170                 175 ttg cta aat ctg gga gtc att ttc ttc ttt aca cta tcc cta att aca    576
Leu Leu Asn Leu Gly Val Ile Phe Phe Phe Thr Leu Ser Leu Ile Thr
            180                 185                 190 tgt att ttt tta atc att tcc ctt tgg aga cac aac agg cag atg caa    624
Cys Ile Phe Leu Ile Ile Ser Leu Trp Arg His Asn Arg Gln Met Gln
        195                 200                 205 tcg aat gtg aca gga ttg aga gac tcc aac aca gaa gct cat gtg aag    672
Ser Asn Val Thr Gly Leu Arg Asp Ser Asn Thr Glu Ala His Val Lys
    210                 215                 220 gca atg aaa gtt tgt ata tct ttc atc atc ctc ttt atc ttg tat ttt    720
Ala Met Lys Val Leu Ile Ser Phe Ile Ile Leu Phe Ile Leu Tyr Phe
225                 230                 235                 240 ata ggc atg gcc ata gaa ata tca tgt ttt act gtg cga gaa aac aaa    768
Ile Gly Met Ala Ile Glu Ile Ser Cys Phe Thr Val Arg Glu Asn Lys
                245                 250                 255 ctg ctg ctt atg ttt gga atg aca acc aca gcc atc tat ccc tgg ggt    816
Leu Leu Leu Met Phe Gly Met Thr Thr Thr Ala Ile Tyr Pro Trp Gly
            260                 265                 270 cac tca ttt atc tta att cta gga aac agc aag cta aag caa gcc tct    864
His Ser Phe Ile Leu Ile Leu Gly Asn Ser Lys Leu Lys Gln Ala Ser
        275                 280                 285 ttg agg gta ctg cag caa ttg aag tgc tgt gag aaa agg aaa aat ctc    912
Leu Arg Val Leu Gln Gln Leu Lys Cys Cys Glu Lys Arg Lys Asn Leu
    290                 295                 300 aga gtc aca tag                                                    924
Arg Val Thr
305

<210> SEQ ID NO 38
<211> LENGTH: 307
<212> TYPE: PRT
<213> ORGANISM: Homo sapiens
```

<400> SEQUENCE: 38

Met Leu Arg Val Val Glu Gly Ile Phe Ile Phe Val Val Ser Glu
1               5                   10                  15

Ser Val Phe Gly Val Leu Gly Asn Gly Phe Ile Gly Leu Val Asn Cys
            20                  25                  30

Ile Asp Cys Ala Lys Asn Lys Leu Ser Thr Ile Gly Phe Ile Leu Thr
        35                  40                  45

Gly Leu Ala Ile Ser Arg Ile Phe Leu Ile Trp Ile Ile Thr Asp
    50                  55                  60

Gly Phe Ile Gln Ile Phe Ser Pro Asn Ile Tyr Ala Ser Gly Asn Leu
65                  70                  75                  80

Ile Glu Tyr Ile Ser Tyr Phe Trp Val Ile Gly Asn Gln Ser Ser Met
                85                  90                  95

Trp Phe Ala Thr Ser Leu Ser Ile Phe Tyr Phe Leu Lys Ile Ala Asn
            100                 105                 110

Phe Ser Asn Tyr Ile Phe Leu Trp Leu Lys Ser Arg Thr Asn Met Val
        115                 120                 125

Leu Pro Phe Met Ile Val Phe Leu Leu Ile Ser Ser Leu Leu Asn Phe
    130                 135                 140

Ala Tyr Ile Ala Lys Ile Leu Asn Asp Tyr Lys Thr Lys Asn Asp Thr
145                 150                 155                 160

Val Trp Asp Leu Asn Met Tyr Lys Ser Glu Tyr Phe Ile Lys Gln Ile
                165                 170                 175

Leu Leu Asn Leu Gly Val Ile Phe Phe Phe Thr Leu Ser Leu Ile Thr
            180                 185                 190

Cys Ile Phe Leu Ile Ile Ser Leu Trp Arg His Asn Arg Gln Met Gln
        195                 200                 205

Ser Asn Val Thr Gly Leu Arg Asp Ser Asn Thr Glu Ala His Val Lys
    210                 215                 220

Ala Met Lys Val Leu Ile Ser Phe Ile Ile Leu Phe Ile Leu Tyr Phe
225                 230                 235                 240

Ile Gly Met Ala Ile Glu Ile Ser Cys Phe Thr Val Arg Glu Asn Lys
                245                 250                 255

Leu Leu Leu Met Phe Gly Met Thr Thr Thr Ala Ile Tyr Pro Trp Gly
            260                 265                 270

His Ser Phe Ile Leu Ile Leu Gly Asn Ser Lys Leu Lys Gln Ala Ser
        275                 280                 285

Leu Arg Val Leu Gln Leu Lys Cys Cys Glu Lys Arg Lys Asn Leu
    290                 295                 300

Arg Val Thr
305

<210> SEQ ID NO 39
<211> LENGTH: 912
<212> TYPE: DNA
<213> ORGANISM: Homo sapiens
<220> FEATURE:
<221> NAME/KEY: CDS
<222> LOCATION: (1)..(912)

<400> SEQUENCE: 39 atg gaa agt gcc ctg ccg agt atc ttc act ctt gta ata att gca gaa     48
Met Glu Ser Ala Leu Pro Ser Ile Phe Thr Leu Val Ile Ile Ala Glu
1               5                   10                  15 ttc ata att ggg aat ttg agc aat gga ttt ata gta ctg atc aac tgc     96
Phe Ile Ile Gly Asn Leu Ser Asn Gly Phe Ile Val Leu Ile Asn Cys
            20                  25                  30

```
att gac tgg gtc agt aaa aga gag ctg tcc tca gtc gat aaa ctc ctc      144
Ile Asp Trp Val Ser Lys Arg Glu Leu Ser Ser Val Asp Lys Leu Leu
        35                  40                  45 att atc ttg gca atc tcc aga att ggg ctg atc tgg gaa ata tta gta      192
Ile Ile Leu Ala Ile Ser Arg Ile Gly Leu Ile Trp Glu Ile Leu Val
 50                  55                  60 agt tgg ttt tta gct ctg cat tat cta gcc ata ttt gtg tct gga aca      240
Ser Trp Phe Leu Ala Leu His Tyr Leu Ala Ile Phe Val Ser Gly Thr
 65                  70                  75                  80 gga tta aga att atg att ttt agc tgg ata gtt tct aat cac ttc aat      288
Gly Leu Arg Ile Met Ile Phe Ser Trp Ile Val Ser Asn His Phe Asn
                 85                  90                  95 ctc tgg ctt gct aca atc ttc agc atc ttt tat ttg ctc aaa ata gcg      336
Leu Trp Leu Ala Thr Ile Phe Ser Ile Phe Tyr Leu Leu Lys Ile Ala
            100                 105                 110 agt ttc tct agc cct gct ttt ctc tat ttg aag tgg aga gta aac aaa      384
Ser Phe Ser Ser Pro Ala Phe Leu Tyr Leu Lys Trp Arg Val Asn Lys
        115                 120                 125 gtg att ctg atg ata ctg cta gga acc ttg gtc ttc tta ttt tta aat      432
Val Ile Leu Met Ile Leu Leu Gly Thr Leu Val Phe Leu Phe Leu Asn
130                 135                 140 ctg ata caa ata aac atg cat ata aaa gac tgg ctg gac cga tat gaa      480
Leu Ile Gln Ile Asn Met His Ile Lys Asp Trp Leu Asp Arg Tyr Glu
145                 150                 155                 160 aga aac aca act tgg aat ttc agt atg agt gac ttt gaa aca ttt tca      528
Arg Asn Thr Thr Trp Asn Phe Ser Met Ser Asp Phe Glu Thr Phe Ser
                165                 170                 175 gtg tcg gtc aaa ttc act atg act atg ttc agt cta aca cca ttt act      576
Val Ser Val Lys Phe Thr Met Thr Met Phe Ser Leu Thr Pro Phe Thr
            180                 185                 190 gtg gcc ttc atc tct ttt ctc ctg tta att ttc tcc ctg cag aaa cat      624
Val Ala Phe Ile Ser Phe Leu Leu Leu Ile Phe Ser Leu Gln Lys His
        195                 200                 205 ctc cag aaa atg caa ctc aat tac aaa gga cac aga gac ccc agg acc      672
Leu Gln Lys Met Gln Leu Asn Tyr Lys Gly His Arg Asp Pro Arg Thr
    210                 215                 220 aag gtc cat aca aat gcc ttg aaa att gtg atc tca ttc ctt tta ttc      720
Lys Val His Thr Asn Ala Leu Lys Ile Val Ile Ser Phe Leu Leu Phe
225                 230                 235                 240 tat gct agt ttc ttt cta tgt gtt ctc ata tca tgg att tct gag ctg      768
Tyr Ala Ser Phe Phe Leu Cys Val Leu Ile Ser Trp Ile Ser Glu Leu
                245                 250                 255 tat cag aac aca gtg atc tac atg ctt tgt gag acg att gga gtc ttc      816
Tyr Gln Asn Thr Val Ile Tyr Met Leu Cys Glu Thr Ile Gly Val Phe
            260                 265                 270 tct cct tca agc cac tcc ttt ctt ctg att cta gga aac gct aag tta      864
Ser Pro Ser Ser His Ser Phe Leu Leu Ile Leu Gly Asn Ala Lys Leu
        275                 280                 285 aga cag gcc ttt ctt ttg gtg gca gct aag gta tgg gct aaa cga tga      912
Arg Gln Ala Phe Leu Leu Val Ala Ala Lys Val Trp Ala Lys Arg
    290                 295                 300

<210> SEQ ID NO 40
<211> LENGTH: 303
<212> TYPE: PRT
<213> ORGANISM: Homo sapiens

<400> SEQUENCE: 40

Met Glu Ser Ala Leu Pro Ser Ile Phe Thr Leu Val Ile Ile Ala Glu
1               5                   10                  15
```

```
Phe Ile Ile Gly Asn Leu Ser Asn Gly Phe Ile Val Leu Ile Asn Cys
         20                  25                  30

Ile Asp Trp Val Ser Lys Arg Glu Leu Ser Ser Val Asp Lys Leu Leu
             35                  40                  45

Ile Ile Leu Ala Ile Ser Arg Ile Gly Leu Ile Trp Glu Ile Leu Val
 50                  55                  60

Ser Trp Phe Leu Ala Leu His Tyr Leu Ala Ile Phe Val Ser Gly Thr
 65                  70                  75                  80

Gly Leu Arg Ile Met Ile Phe Ser Trp Ile Val Ser Asn His Phe Asn
                 85                  90                  95

Leu Trp Leu Ala Thr Ile Phe Ser Ile Phe Tyr Leu Leu Lys Ile Ala
                100                 105                 110

Ser Phe Ser Ser Pro Ala Phe Leu Tyr Leu Lys Trp Arg Val Asn Lys
            115                 120                 125

Val Ile Leu Met Ile Leu Leu Gly Thr Leu Val Phe Leu Phe Leu Asn
130                 135                 140

Leu Ile Gln Ile Asn Met His Ile Lys Asp Trp Leu Asp Arg Tyr Glu
145                 150                 155                 160

Arg Asn Thr Thr Trp Asn Phe Ser Met Ser Asp Phe Glu Thr Phe Ser
                165                 170                 175

Val Ser Val Lys Phe Thr Met Thr Met Phe Ser Leu Thr Pro Phe Thr
            180                 185                 190

Val Ala Phe Ile Ser Phe Leu Leu Leu Ile Phe Ser Leu Gln Lys His
        195                 200                 205

Leu Gln Lys Met Gln Leu Asn Tyr Lys Gly His Arg Asp Pro Arg Thr
210                 215                 220

Lys Val His Thr Asn Ala Leu Lys Ile Val Ile Ser Phe Leu Leu Phe
225                 230                 235                 240

Tyr Ala Ser Phe Phe Leu Cys Val Leu Ile Ser Trp Ile Ser Glu Leu
                245                 250                 255

Tyr Gln Asn Thr Val Ile Tyr Met Leu Cys Glu Thr Ile Gly Val Phe
            260                 265                 270

Ser Pro Ser Ser His Ser Phe Leu Leu Ile Leu Gly Asn Ala Lys Leu
        275                 280                 285

Arg Gln Ala Phe Leu Leu Val Ala Ala Lys Val Trp Ala Lys Arg
290                 295                 300

<210> SEQ ID NO 41
<211> LENGTH: 969
<212> TYPE: DNA
<213> ORGANISM: Homo sapiens
<220> FEATURE:
<221> NAME/KEY: CDS
<222> LOCATION: (1)..(969)

<400> SEQUENCE: 41 atg ctc tta cag gca atg ggt ggt gtc ata aag agc ata ttt aca ttc    48
Met Leu Leu Gln Ala Met Gly Gly Val Ile Lys Ser Ile Phe Thr Phe
1               5                   10                  15 gtt tta att gtg gaa ttt ata att gga aat tta gga aat agt ttc ata    96
Val Leu Ile Val Glu Phe Ile Ile Gly Asn Leu Gly Asn Ser Phe Ile
            20                  25                  30 gca ctg gtg aac tgt att gac tgg gtc aag gga aga aag atc tct tcg   144
Ala Leu Val Asn Cys Ile Asp Trp Val Lys Gly Arg Lys Ile Ser Ser
        35                  40                  45 gtt gat cgg atc ctc act gct ttg gca atc tct cga att agc ctg gtt   192
Val Asp Arg Ile Leu Thr Ala Leu Ala Ile Ser Arg Ile Ser Leu Val
 50                  55                  60
```

```
tgg tta ata ttc gga agc tgg tgt gtg tct gtg ttt ttc cca gct tta      240
Trp Leu Ile Phe Gly Ser Trp Cys Val Ser Val Phe Phe Pro Ala Leu
 65              70                  75                  80 ttt gcc act gaa aaa atg ttc aga atg ctt act aat atc tgg aca gtg      288
Phe Ala Thr Glu Lys Met Phe Arg Met Leu Thr Asn Ile Trp Thr Val
                 85                  90                  95 atc aat cat ttt agt gtc tgg tta gct aca ggc ctc ggt act ttt tat      336
Ile Asn His Phe Ser Val Trp Leu Ala Thr Gly Leu Gly Thr Phe Tyr
            100                 105                 110 ttt ctc aag ata gcc aat ttt tct aac tct att ttt ctc tac cta aag      384
Phe Leu Lys Ile Ala Asn Phe Ser Asn Ser Ile Phe Leu Tyr Leu Lys
        115                 120                 125 tgg agg gtt aaa aag gtg gtt ttg gtg ctg ctt ctt gtg act tcg gtc      432
Trp Arg Val Lys Lys Val Val Leu Val Leu Leu Leu Val Thr Ser Val
130                 135                 140 ttc ttg ttt tta aat att gca ctg ata aac atc cat ata aat gcc agt      480
Phe Leu Phe Leu Asn Ile Ala Leu Ile Asn Ile His Ile Asn Ala Ser
145                 150                 155                 160 atc aat gga tac aga aga aac aag act tgc agt tct gat tca agt aac      528
Ile Asn Gly Tyr Arg Arg Asn Lys Thr Cys Ser Ser Asp Ser Ser Asn
                165                 170                 175 ttt aca cga ttt tcc agt ctt att gta tta acc agc act gtg ttc att      576
Phe Thr Arg Phe Ser Ser Leu Ile Val Leu Thr Ser Thr Val Phe Ile
            180                 185                 190 ttc ata ccc ttt act ttg tcc ctg gca atg ttt ctt ctc atc ttc          624
Phe Ile Pro Phe Thr Leu Ser Leu Ala Met Phe Leu Leu Ile Phe
        195                 200                 205 tcc atg tgg aaa cat cgc aag aag atg cag cac act gtc aaa ata tcc      672
Ser Met Trp Lys His Arg Lys Lys Met Gln His Thr Val Lys Ile Ser
210                 215                 220 gga gac gcc agc acc aaa gcc cac aga gga gtt aaa agt gtg atc act      720
Gly Asp Ala Ser Thr Lys Ala His Arg Gly Val Lys Ser Val Ile Thr
225                 230                 235                 240 ttc ttc cta ctc tat gcc att ttc tct ctg tct ttt tca ata tca gtt      768
Phe Phe Leu Leu Tyr Ala Ile Phe Ser Leu Ser Phe Phe Ile Ser Val
                245                 250                 255 tgg acc tct gaa agg ttg gag gaa aat cta att att ctt tcc cag gtg      816
Trp Thr Ser Glu Arg Leu Glu Glu Asn Leu Ile Ile Leu Ser Gln Val
            260                 265                 270 atg gga atg gct tat cct tca tgt cac tca tgt gtt ctg att ctt gga      864
Met Gly Met Ala Tyr Pro Ser Cys His Ser Cys Val Leu Ile Leu Gly
        275                 280                 285 aac aag aag ctg aga cag gcc tct ctg tca gta cta tgg ctg agg          912
Asn Lys Lys Leu Arg Gln Ala Ser Leu Ser Val Leu Trp Leu Arg
290                 295                 300 tac atg ttc aaa gat ggg gag ccc tca ggt cac aaa gaa ttt aga gaa      960
Tyr Met Phe Lys Asp Gly Glu Pro Ser Gly His Lys Glu Phe Arg Glu
305                 310                 315                 320 tca tct tga                                                          969
Ser Ser <210> SEQ ID NO 42
<211> LENGTH: 322
<212> TYPE: PRT
<213> ORGANISM: Homo sapiens

<400> SEQUENCE: 42

Met Leu Leu Gln Ala Met Gly Gly Val Ile Lys Ser Ile Phe Thr Phe
 1               5                  10                  15

Val Leu Ile Val Glu Phe Ile Ile Gly Asn Leu Gly Asn Ser Phe Ile
```

```
                    20                  25                  30
Ala Leu Val Asn Cys Ile Asp Trp Val Lys Gly Arg Lys Ile Ser Ser
                35                  40                  45

Val Asp Arg Ile Leu Thr Ala Leu Ala Ile Ser Arg Ile Ser Leu Val
    50                  55                  60

Trp Leu Ile Phe Gly Ser Trp Cys Val Ser Val Phe Phe Pro Ala Leu
65                  70                  75                  80

Phe Ala Thr Glu Lys Met Phe Arg Met Leu Thr Asn Ile Trp Thr Val
                85                  90                  95

Ile Asn His Phe Ser Val Trp Leu Ala Thr Gly Leu Gly Thr Phe Tyr
            100                 105                 110

Phe Leu Lys Ile Ala Asn Phe Ser Asn Ser Ile Phe Leu Tyr Leu Lys
        115                 120                 125

Trp Arg Val Lys Lys Val Val Leu Val Leu Leu Val Thr Ser Val
    130                 135                 140

Phe Leu Phe Leu Asn Ile Ala Leu Ile Asn Ile His Ile Asn Ala Ser
145                 150                 155                 160

Ile Asn Gly Tyr Arg Arg Asn Lys Thr Cys Ser Ser Asp Ser Ser Asn
                165                 170                 175

Phe Thr Arg Phe Ser Ser Leu Ile Val Leu Thr Ser Thr Val Phe Ile
            180                 185                 190

Phe Ile Pro Phe Thr Leu Ser Leu Ala Met Phe Leu Leu Leu Ile Phe
        195                 200                 205

Ser Met Trp Lys His Arg Lys Lys Met Gln His Thr Val Lys Ile Ser
    210                 215                 220

Gly Asp Ala Ser Thr Lys Ala His Arg Gly Val Lys Ser Val Ile Thr
225                 230                 235                 240

Phe Phe Leu Leu Tyr Ala Ile Phe Ser Leu Ser Phe Ile Ser Val
                245                 250                 255

Trp Thr Ser Glu Arg Leu Glu Glu Asn Leu Ile Ile Leu Ser Gln Val
            260                 265                 270

Met Gly Met Ala Tyr Pro Ser Cys His Ser Cys Val Leu Ile Leu Gly
        275                 280                 285

Asn Lys Lys Leu Arg Gln Ala Ser Leu Ser Val Leu Leu Trp Leu Arg
    290                 295                 300

Tyr Met Phe Lys Asp Gly Glu Pro Ser Gly His Lys Glu Phe Arg Glu
305                 310                 315                 320

Ser Ser

<210> SEQ ID NO 43
<211> LENGTH: 876
<212> TYPE: DNA
<213> ORGANISM: Homo sapiens
<220> FEATURE:
<221> NAME/KEY: CDS
<222> LOCATION: (1)..(876)

<400> SEQUENCE: 43 atg ata ccc atc caa ctc act gtc ttc ttc atg atc atc tat gtg ctt    48
Met Ile Pro Ile Gln Leu Thr Val Phe Phe Met Ile Ile Tyr Val Leu
1               5                   10                  15 gag tcc ttg aca att att gtg cag agc agc cta att gtt gca gtg ctg    96
Glu Ser Leu Thr Ile Ile Val Gln Ser Ser Leu Ile Val Ala Val Leu
                20                  25                  30 ggc aga gaa tgg ctg caa gtc aga agg ctg atg cct gtg gac atg att   144
Gly Arg Glu Trp Leu Gln Val Arg Arg Leu Met Pro Val Asp Met Ile
            35                  40                  45
```

| | |
|---|---|
| ctc atc agc ctg ggc atc tct cgc ttc tgt cta cag tgg gca tca atg<br>Leu Ile Ser Leu Gly Ile Ser Arg Phe Cys Leu Gln Trp Ala Ser Met<br>    50                          55                          60 | 192 |
| ctg aac aat ttt tgc tcc tat ttt aat ttg aat tat gta ctt tgc aac<br>Leu Asn Asn Phe Cys Ser Tyr Phe Asn Leu Asn Tyr Val Leu Cys Asn<br>65                       70                        75                        80 | 240 |
| tta aca atc acc tgg gaa ttt ttt aat atc ctt aca ttc tgg tta aac<br>Leu Thr Ile Thr Trp Glu Phe Phe Asn Ile Leu Thr Phe Trp Leu Asn<br>                                    85                        90                        95 | 288 |
| agc ttg ctt acc gtg ttc tac tgc atc aag gtc tct tct ttc acc cat<br>Ser Leu Leu Thr Val Phe Tyr Cys Ile Lys Val Ser Ser Phe Thr His<br>               100                     105                     110 | 336 |
| cac atc ttt ctc tgg ctg agg tgg aga att ttg agg ttg ttt ccc tgg<br>His Ile Phe Leu Trp Leu Arg Trp Arg Ile Leu Arg Leu Phe Pro Trp<br>        115                     120                     125 | 384 |
| ata tta ctg ggt tct ctg atg att act tgt gta aca atc atc cct tca<br>Ile Leu Leu Gly Ser Leu Met Ile Thr Cys Val Thr Ile Ile Pro Ser<br>130                           135                     140 | 432 |
| gct att ggg aat tac att caa att cag tta ctc acc atg gag cat cta<br>Ala Ile Gly Asn Tyr Ile Gln Ile Gln Leu Leu Thr Met Glu His Leu<br>145                     150                     155                     160 | 480 |
| cca aga aac agc act gta act gac aaa ctt gaa aat ttt cat cag tat<br>Pro Arg Asn Ser Thr Val Thr Asp Lys Leu Glu Asn Phe His Gln Tyr<br>                    165                     170                     175 | 528 |
| cag ttc cag gct cat aca gtt gca ttg gtt att cct ttc atc ctg ttc<br>Gln Phe Gln Ala His Thr Val Ala Leu Val Ile Pro Phe Ile Leu Phe<br>               180                     185                     190 | 576 |
| ctg gcc tcc acc atc ttt ctc atg gca tca ctg acc aag cag ata caa<br>Leu Ala Ser Thr Ile Phe Leu Met Ala Ser Leu Thr Lys Gln Ile Gln<br>        195                     200                     205 | 624 |
| cat cat agc act ggt cac tgc aat cca agc atg aaa gcg cgc ttc act<br>His His Ser Thr Gly His Cys Asn Pro Ser Met Lys Ala Arg Phe Thr<br>210                         215                     220 | 672 |
| gcc ctg agg tcc ctt gcc gtc tta ttt att gtg ttt acc tct tac ttt<br>Ala Leu Arg Ser Leu Ala Val Leu Phe Ile Val Phe Thr Ser Tyr Phe<br>225                     230                     235                     240 | 720 |
| cta acc ata ctc atc acc att ata ggt act cta ttt gat aag aga tgt<br>Leu Thr Ile Leu Ile Thr Ile Ile Gly Thr Leu Phe Asp Lys Arg Cys<br>               245                     250                     255 | 768 |
| tgg tta tgg gtc tgg gaa gct ttt gtc tat gct ttc atc tta atg cat<br>Trp Leu Trp Val Trp Glu Ala Phe Val Tyr Ala Phe Ile Leu Met His<br>               260                     265                     270 | 816 |
| tcc act tca ctg atg ctg agc agc cct acg ttg aaa agg att cta aag<br>Ser Thr Ser Leu Met Leu Ser Ser Pro Thr Leu Lys Arg Ile Leu Lys<br>        275                     280                     285 | 864 |
| gga aag tgc tag<br>Gly Lys Cys<br>    290 | 876 |

<210> SEQ ID NO 44
<211> LENGTH: 291
<212> TYPE: PRT
<213> ORGANISM: Homo sapiens

<400> SEQUENCE: 44

Met Ile Pro Ile Gln Leu Thr Val Phe Phe Met Ile Ile Tyr Val Leu
1                     5                        10                        15

Glu Ser Leu Thr Ile Ile Val Gln Ser Ser Leu Ile Val Ala Val Leu
                20                     25                     30

Gly Arg Glu Trp Leu Gln Val Arg Arg Leu Met Pro Val Asp Met Ile

```
                35                  40                  45
Leu Ile Ser Leu Gly Ile Ser Arg Phe Cys Leu Gln Trp Ala Ser Met
 50                  55                  60

Leu Asn Asn Phe Cys Ser Tyr Phe Asn Leu Asn Tyr Val Leu Cys Asn
 65                  70                  75                  80

Leu Thr Ile Thr Trp Glu Phe Phe Asn Ile Leu Thr Phe Trp Leu Asn
                 85                  90                  95

Ser Leu Leu Thr Val Phe Tyr Cys Ile Lys Val Ser Ser Phe Thr His
            100                 105                 110

His Ile Phe Leu Trp Leu Arg Trp Arg Ile Leu Arg Leu Phe Pro Trp
        115                 120                 125

Ile Leu Leu Gly Ser Leu Met Ile Thr Cys Val Thr Ile Ile Pro Ser
    130                 135                 140

Ala Ile Gly Asn Tyr Ile Gln Ile Gln Leu Leu Thr Met Glu His Leu
145                 150                 155                 160

Pro Arg Asn Ser Thr Val Thr Asp Lys Leu Glu Asn Phe His Gln Tyr
                165                 170                 175

Gln Phe Gln Ala His Thr Val Ala Leu Val Ile Pro Phe Ile Leu Phe
            180                 185                 190

Leu Ala Ser Thr Ile Phe Leu Met Ala Ser Leu Thr Lys Gln Ile Gln
        195                 200                 205

His His Ser Thr Gly His Cys Asn Pro Ser Met Lys Ala Arg Phe Thr
    210                 215                 220

Ala Leu Arg Ser Leu Ala Val Leu Phe Ile Val Phe Thr Ser Tyr Phe
225                 230                 235                 240

Leu Thr Ile Leu Ile Thr Ile Ile Gly Thr Leu Phe Asp Lys Arg Cys
                245                 250                 255

Trp Leu Trp Val Trp Glu Ala Phe Val Tyr Ala Phe Ile Leu Met His
            260                 265                 270

Ser Thr Ser Leu Met Leu Ser Ser Pro Thr Leu Lys Arg Ile Leu Lys
        275                 280                 285

Gly Lys Cys
    290

<210> SEQ ID NO 45
<211> LENGTH: 21
<212> TYPE: DNA
<213> ORGANISM: Artificial Sequence
<220> FEATURE:
<223> OTHER INFORMATION: Synthetic primer

<400> SEQUENCE: 45
atgttgactc taactcgcat c                                          21

<210> SEQ ID NO 46
<211> LENGTH: 22
<212> TYPE: DNA
<213> ORGANISM: Artificial Sequence
<220> FEATURE:
<223> OTHER INFORMATION: Synthetic primer

<400> SEQUENCE: 46
tcagcacagt gtccgggaat ct                                         22

<210> SEQ ID NO 47
<211> LENGTH: 22
<212> TYPE: DNA
<213> ORGANISM: Artificial Sequence
<220> FEATURE:
```

```
<223> OTHER INFORMATION: Synthetic primer

<400> SEQUENCE: 47
atgataactt ttctgcccat ca                                          22

<210> SEQ ID NO 48
<211> LENGTH: 23
<212> TYPE: DNA
<213> ORGANISM: Artificial Sequence
<220> FEATURE:
<223> OTHER INFORMATION: Synthetic primer

<400> SEQUENCE: 48
ctagaagaca cacaatgccc ctc                                         23

<210> SEQ ID NO 49
<211> LENGTH: 21
<212> TYPE: DNA
<213> ORGANISM: Artificial Sequence
<220> FEATURE:
<223> OTHER INFORMATION: Synthetic primer

<400> SEQUENCE: 49
atgataactt ttctgcccat c                                           21

<210> SEQ ID NO 50
<211> LENGTH: 26
<212> TYPE: DNA
<213> ORGANISM: Artificial Sequence
<220> FEATURE:
<223> OTHER INFORMATION: Synthetic primer

<400> SEQUENCE: 50
tcagtacctc atttgccaca aaactg                                      26

<210> SEQ ID NO 51
<211> LENGTH: 18
<212> TYPE: DNA
<213> ORGANISM: Artificial Sequence
<220> FEATURE:
<223> OTHER INFORMATION: Synthetic primer

<400> SEQUENCE: 51
atggccaccg aattggac                                               18

<210> SEQ ID NO 52
<211> LENGTH: 23
<212> TYPE: DNA
<213> ORGANISM: Artificial Sequence
<220> FEATURE:
<223> OTHER INFORMATION: Synthetic primer

<400> SEQUENCE: 52
ctacaaaggt aaagggtttg gtg                                         23

<210> SEQ ID NO 53
<211> LENGTH: 22
<212> TYPE: DNA
<213> ORGANISM: Artificial Sequence
<220> FEATURE:
<223> OTHER INFORMATION: Synthetic primer

<400> SEQUENCE: 53
atggcaacgg tgaacacaga tg                                          22

<210> SEQ ID NO 54
```

-continued

```
<211> LENGTH: 23
<212> TYPE: DNA
<213> ORGANISM: Artificial Sequence
<220> FEATURE:
<223> OTHER INFORMATION: Synthetic primer

<400> SEQUENCE: 54
tcacagagtc tgccctttta ggt                                              23

<210> SEQ ID NO 55
<211> LENGTH: 23
<212> TYPE: DNA
<213> ORGANISM: Artificial Sequence
<220> FEATURE:
<223> OTHER INFORMATION: Synthetic primer

<400> SEQUENCE: 55
atgctaggga gatgttttcc tcc                                              23

<210> SEQ ID NO 56
<211> LENGTH: 23
<212> TYPE: DNA
<213> ORGANISM: Artificial Sequence
<220> FEATURE:
<223> OTHER INFORMATION: Synthetic primer

<400> SEQUENCE: 56
tcacagagtc cactcttttg ggt                                              23

<210> SEQ ID NO 57
<211> LENGTH: 23
<212> TYPE: DNA
<213> ORGANISM: Artificial Sequence
<220> FEATURE:
<223> OTHER INFORMATION: Synthetic primer

<400> SEQUENCE: 57
atgctaggga gatgttttcc tcc                                              23

<210> SEQ ID NO 58
<211> LENGTH: 23
<212> TYPE: DNA
<213> ORGANISM: Artificial Sequence
<220> FEATURE:
<223> OTHER INFORMATION: Synthetic primer

<400> SEQUENCE: 58
tcacagagtc tgccctttta ggt                                              23

<210> SEQ ID NO 59
<211> LENGTH: 21
<212> TYPE: DNA
<213> ORGANISM: Artificial
<220> FEATURE:
<223> OTHER INFORMATION: Synthetic primer

<400> SEQUENCE: 59
atgataactt ttctacccat c                                                21

<210> SEQ ID NO 60
<211> LENGTH: 24
<212> TYPE: DNA
<213> ORGANISM: Artificial Sequence
<220> FEATURE:
<223> OTHER INFORMATION: Synthetic primer

<400> SEQUENCE: 60
```
ctatggagat gaagtcttct ctcc                                24

<210> SEQ ID NO 61
<211> LENGTH: 22
<212> TYPE: DNA
<213> ORGANISM: Artificial Sequence
<220> FEATURE:
<223> OTHER INFORMATION: Synthetic primer

<400> SEQUENCE: 61
atgttaaagg actcagaaca ag                                  22

<210> SEQ ID NO 62
<211> LENGTH: 22
<212> TYPE: DNA
<213> ORGANISM: Artificial Sequence
<220> FEATURE:
<223> OTHER INFORMATION: Synthetic primer

<400> SEQUENCE: 62
tcagcgtgtc atctgccaca aa                                  22

<210> SEQ ID NO 63
<211> LENGTH: 22
<212> TYPE: DNA
<213> ORGANISM: Artificial Sequence
<220> FEATURE:
<223> OTHER INFORMATION: Synthetic primer

<400> SEQUENCE: 63
atgatgagtt ttctacacat tg                                  22

<210> SEQ ID NO 64
<211> LENGTH: 24
<212> TYPE: DNA
<213> ORGANISM: Artificial Sequence
<220> FEATURE:
<223> OTHER INFORMATION: Synthetic primer

<400> SEQUENCE: 64
ctatggagtt gactggttct gtcc                                24

<210> SEQ ID NO 65
<211> LENGTH: 21
<212> TYPE: DNA
<213> ORGANISM: Artificial Sequence
<220> FEATURE:
<223> OTHER INFORMATION: Synthetic primer

<400> SEQUENCE: 65
atgacaactt ttatacccat c                                   21

<210> SEQ ID NO 66
<211> LENGTH: 24
<212> TYPE: DNA
<213> ORGANISM: Artificial Sequence
<220> FEATURE:
<223> OTHER INFORMATION: Synthetic primer

<400> SEQUENCE: 66
ctatggagat gaaggcttct ctcc                                24

<210> SEQ ID NO 67
<211> LENGTH: 24
<212> TYPE: DNA
<213> ORGANISM: Artificial Sequence
<220> FEATURE:

<223> OTHER INFORMATION: Synthetic primer

<400> SEQUENCE: 67
atgctagagt ctcacctcat tatc    24

<210> SEQ ID NO 68
<211> LENGTH: 25
<212> TYPE: DNA
<213> ORGANISM: Artificial Sequence
<220> FEATURE:
<223> OTHER INFORMATION: Synthetic primer

<400> SEQUENCE: 68
tcactgacag cacttactgt ggagg    25

<210> SEQ ID NO 69
<211> LENGTH: 22
<212> TYPE: DNA
<213> ORGANISM: Artificial Sequence
<220> FEATURE:
<223> OTHER INFORMATION: Synthetic primer

<400> SEQUENCE: 69
atgatgggac tcaccgaggg gg    22

<210> SEQ ID NO 70
<211> LENGTH: 23
<212> TYPE: DNA
<213> ORGANISM: Artificial Sequence
<220> FEATURE:
<223> OTHER INFORMATION: Synthetic primer

<400> SEQUENCE: 70
ctaagagaaa atgggtccct tgg    23

<210> SEQ ID NO 71
<211> LENGTH: 21
<212> TYPE: DNA
<213> ORGANISM: Artificial Sequence
<220> FEATURE:
<223> OTHER INFORMATION: Synthetic primer

<400> SEQUENCE: 71
atgcttcggt tattctattt c    21

<210> SEQ ID NO 72
<211> LENGTH: 22
<212> TYPE: DNA
<213> ORGANISM: Artificial Sequence
<220> FEATURE:
<223> OTHER INFORMATION: Synthetic primer

<400> SEQUENCE: 72 ctatttttg aaacaaagaa tc    22

<210> SEQ ID NO 73
<211> LENGTH: 24
<212> TYPE: DNA
<213> ORGANISM: Artificial Sequence
<220> FEATURE:
<223> OTHER INFORMATION: Synthetic primer

<400> SEQUENCE: 73
atgctgagcg ctggcctagg actg    24

<210> SEQ ID NO 74

```
<211> LENGTH: 24
<212> TYPE: DNA
<213> ORGANISM: Artificial Sequence
<220> FEATURE:
<223> OTHER INFORMATION: Synthetic primer

<400> SEQUENCE: 74
tcatgggccc cagcatctcc gagc                                          24

<210> SEQ ID NO 75
<211> LENGTH: 23
<212> TYPE: DNA
<213> ORGANISM: Artificial Sequence
<220> FEATURE:
<223> OTHER INFORMATION: Synthetic primer

<400> SEQUENCE: 75
atggcagata aagtgcagac tac                                           23

<210> SEQ ID NO 76
<211> LENGTH: 23
<212> TYPE: DNA
<213> ORGANISM: Artificial Sequence
<220> FEATURE:
<223> OTHER INFORMATION: Synthetic primer

<400> SEQUENCE: 76
tcagatttgt ttatgttgtt gga                                           23

<210> SEQ ID NO 77
<211> LENGTH: 21
<212> TYPE: DNA
<213> ORGANISM: Artificial Sequence
<220> FEATURE:
<223> OTHER INFORMATION: Synthetic primer

<400> SEQUENCE: 77
atgttcagtc ctgcagataa c                                             21

<210> SEQ ID NO 78
<211> LENGTH: 23
<212> TYPE: DNA
<213> ORGANISM: Artificial Sequence
<220> FEATURE:
<223> OTHER INFORMATION: Synthetic primer

<400> SEQUENCE: 78
tcatatcatg caggcaattt ttc                                           23

<210> SEQ ID NO 79
<211> LENGTH: 20
<212> TYPE: DNA
<213> ORGANISM: Artificial Sequence
<220> FEATURE:
<223> OTHER INFORMATION: Synthetic primer

<400> SEQUENCE: 79
atgccaagtg caatagaggc                                               20

<210> SEQ ID NO 80
<211> LENGTH: 20
<212> TYPE: DNA
<213> ORGANISM: Artificial Sequence
<220> FEATURE:
<223> OTHER INFORMATION: Synthetic primer

<400> SEQUENCE: 80
```

```
ctatggaaca aaaggctttc                                              20

<210> SEQ ID NO 81
<211> LENGTH: 21
<212> TYPE: DNA
<213> ORGANISM: Artificial Sequence
<220> FEATURE:
<223> OTHER INFORMATION: Synthetic primer

<400> SEQUENCE: 81
atgctacgtg tagtggaagg c                                            21

<210> SEQ ID NO 82
<211> LENGTH: 23
<212> TYPE: DNA
<213> ORGANISM: Artificial Sequence
<220> FEATURE:
<223> OTHER INFORMATION: Synthetic primer

<400> SEQUENCE: 82
ctatgtgact ctgagatttt tcc                                          23

<210> SEQ ID NO 83
<211> LENGTH: 20
<212> TYPE: DNA
<213> ORGANISM: Artificial Sequence
<220> FEATURE:
<223> OTHER INFORMATION: Synthetic primer

<400> SEQUENCE: 83
atggaaagtg ccctgccgag                                              20

<210> SEQ ID NO 84
<211> LENGTH: 19
<212> TYPE: DNA
<213> ORGANISM: Artificial Sequence
<220> FEATURE:
<223> OTHER INFORMATION: Synthetic primer

<400> SEQUENCE: 84
tcatcgttta gcccatacc                                               19

<210> SEQ ID NO 85
<211> LENGTH: 20
<212> TYPE: DNA
<213> ORGANISM: Artificial Sequence
<220> FEATURE:
<223> OTHER INFORMATION: Synthetic primer

<400> SEQUENCE: 85
atgctcttac aggcaatggg                                              20

<210> SEQ ID NO 86
<211> LENGTH: 21
<212> TYPE: DNA
<213> ORGANISM: Artificial Sequence
<220> FEATURE:
<223> OTHER INFORMATION: Synthetic primer

<400> SEQUENCE: 86
tcaagatgat tctctaaatt c                                            21

<210> SEQ ID NO 87
<211> LENGTH: 20
<212> TYPE: DNA
<213> ORGANISM: Artificial Sequence
<220> FEATURE:
```

```
<223> OTHER INFORMATION: Synthetic primer

<400> SEQUENCE: 87
atgataccca tccaactcac                                              20

<210> SEQ ID NO 88
<211> LENGTH: 23
<212> TYPE: DNA
<213> ORGANISM: Artificial Sequence
<220> FEATURE:
<223> OTHER INFORMATION: Synthetic primer

<400> SEQUENCE: 88 ctagcactttt ccctttagaa tcc                                         23
```